United States Patent
Ouberai et al.

(10) Patent No.: US 10,709,717 B2
(45) Date of Patent: Jul. 14, 2020

(54) POLYMER COMPOSED OF REPEAT UNITS HAVING A BIOLOGICALLY ACTIVE MOLECULE ATTACHED THERETO VIA A PH-SENSITIVE BOND

(71) Applicant: SPIREA LIMITED, Harrogate (GB)

(72) Inventors: Myriam Marie Ouberai, Cambridge (GB); Mark Welland, Cambridge (GB)

(73) Assignee: SPIREA LIMITED, Harrogate (GB)

( * ) Notice: Subject to any disclaimer, the term of this patent is extended or adjusted under 35 U.S.C. 154(b) by 32 days.

(21) Appl. No.: 15/518,737

(22) PCT Filed: Oct. 13, 2015

(86) PCT No.: PCT/GB2015/053007
§ 371 (c)(1),
(2) Date: Apr. 12, 2017

(87) PCT Pub. No.: WO2016/059391
PCT Pub. Date: Apr. 21, 2016

(65) Prior Publication Data
US 2017/0224828 A1 Aug. 10, 2017

(30) Foreign Application Priority Data

Oct. 13, 2014 (GB) .................................. 1418068.1

(51) Int. Cl.
*A61K 31/13* (2006.01)
*A61K 31/133* (2006.01)
(Continued)

(52) U.S. Cl.
CPC .......... *A61K 31/573* (2013.01); *A61K 9/5031* (2013.01); *A61K 9/5146* (2013.01);
(Continued)

(58) Field of Classification Search
CPC .. A61K 47/593; A61K 9/5031; A61K 9/5146; A61K 31/13; A61K 31/133;
(Continued)

(56) References Cited

U.S. PATENT DOCUMENTS

| 6,613,807 B2 | 9/2003 | Uhrich |
| 2005/0123600 A1 | 6/2005 | Trubetskoy et al. |

(Continued)

FOREIGN PATENT DOCUMENTS

| CN | 103965455 A | 8/2014 |
| WO | 2004/009082 A1 | 1/2004 |

(Continued)

OTHER PUBLICATIONS

Uhrich et al. (Biomacromolecules, pp. 1-15, Published online Aug. 19, 2013) (Year: 2013).*

(Continued)

*Primary Examiner* — Alma Pipic
(74) *Attorney, Agent, or Firm* — Christensen O'Connor Johnson Kindness PLLC

(57) ABSTRACT

There is provided a polymer comprising: (i) a repeat unit derived from a compound of formula (I) (Formula (I)) wherein, $R^1$ and $R^2$ are each independently selected from OH, OR', SH, SR', $NH_2$, NHR' and $NR'_2$; R' is $C_{1-20}$ hydrocarbyl; each n is independently 0 or an integer between 1 and 6; each m is independently 0 or an integer between 1 and 4, and preferably at least one m is 1; and q is an integer between 1 and 8; and; (ii) a biologically active molecule, wherein said biologically active molecule is covalently bonded to said repeat unit; as well as methods for preparing such polymers, particles comprising said polymers and uses of said polymers and particles including use in the treatment of disease.

(Continued)

US 10,709,717 B2
Page 2

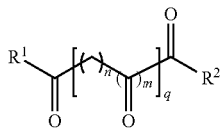

(I)

31 Claims, 18 Drawing Sheets

(51) Int. Cl.

| | |
|---|---|
| A61K 31/138 | (2006.01) |
| A61K 31/4409 | (2006.01) |
| A61K 31/496 | (2006.01) |
| A61K 31/573 | (2006.01) |
| A61K 9/51 | (2006.01) |
| C08G 63/672 | (2006.01) |
| A61K 45/06 | (2006.01) |
| C08G 63/685 | (2006.01) |
| C08G 63/16 | (2006.01) |
| A61K 47/59 | (2017.01) |
| C08G 63/688 | (2006.01) |
| A61K 9/50 | (2006.01) |
| C08G 63/91 | (2006.01) |
| C12P 7/62 | (2006.01) |

(52) U.S. Cl.
CPC ............ *A61K 31/13* (2013.01); *A61K 31/133* (2013.01); *A61K 31/138* (2013.01); *A61K 31/4409* (2013.01); *A61K 31/496* (2013.01); *A61K 45/06* (2013.01); *A61K 47/593* (2017.08); *C08G 63/16* (2013.01); *C08G 63/672* (2013.01); *C08G 63/6856* (2013.01); *C08G 63/6886* (2013.01); *C08G 63/916* (2013.01); *C12P 7/62* (2013.01); *C12Y 301/01003* (2013.01); *Y02A 50/483* (2018.01)

(58) Field of Classification Search
CPC .............. A61K 31/138; A61K 31/4409; A61K 31/496; A61K 45/06; C08G 63/6886; C08G 63/916
See application file for complete search history.

(56) References Cited

U.S. PATENT DOCUMENTS

| | | |
|---|---|---|
| 2012/0027690 A1 | 2/2012 | Lee et al. |
| 2013/0101632 A1 | 4/2013 | Scott et al. |
| 2014/0046018 A1 | 2/2014 | O'Shea et al. |

FOREIGN PATENT DOCUMENTS

| | | |
|---|---|---|
| WO | 2007/119185 A2 | 10/2007 |
| WO | 2009/091103 A1 | 7/2009 |
| WO | 2012/153297 A1 | 11/2012 |

OTHER PUBLICATIONS

Giammona (Chem. Pharm. Bull., pp. 2245-2247, published 1989) (Year: 1989).*
Barrett, D.G., and M.N. Yousaf, "Poly(triol α-ketoglutarate) as Biodegradable, Chemoselective, and Mechanically Tunable Elastomers," Macromolecules 41(17):6347-6352, Sep. 2008.
Barrett, D.G., and M.N. Yousaf, "A Tunable, Chemoselective, and Moldable Biodegradable Polyester for Cell Scaffolds," ChemBioChem 9(1):62-66, Jan. 2008.
Barrett, D.G., and M.N. Yousaf, "Supporting Information for: A Tunable, Chemoselective, and Moldable Biodegradable Polyester for Cell Scaffolds," © 2007 Wiley-VCH Verlag, Weinheim, Germany, <www.wiley-vch.de/contents/jc_2268/2008/z700550_s_pdf> [retrieved as early as Nov. 16, 2007], 4 pages.
Binauld, S., and M.H. Stenzel, "Acid-Degradable Polymers for Drug Delivery: A Decade of Innovation," Chemical Communications 49(21):2082-2102, Mar. 2013.
Dahiyat, B.I., et al., "Degradable Biomaterials With Elastomeric Characteristics and Drug-Carrier Function," Reactive Polymers 25(2-3):101-109, Jun. 1995.
Doğan, F., et al., "Synthesis, Characterization, and Thermal Degradation Kinetics of Poly(decamethylene 2-oxoglutarate)," Journal of Applied Polymer Science 108(4):2328-2336, May 2008.
Guo, X., et al., "pH-Triggered Intracellular Release From Actively Targeting Polymer Micelles," Biomaterials 34(18):4544-4554, Jun. 2013.
He, Y., et al., "Dual-Response Nanocarrier Based on Graft Copolymers With Hydrazone Bond Linkages for Improved Drug Delivery," Colloids and Surfaces B: Biointerfaces 80(2):145-154, Oct. 2010.
Jin, Y., et al., "Oxime Linkage: A Robust Tool for the Design of pH-Sensitive Polymeric Drug Carriers," Biomacromolecules 12(10):3460-3468, Oct. 2011.
Kakkar, D., et al., "Design, Synthesis, and Antimycobacterial Property of PEG-bis(INH) Conjugates," Chemical Biology & Drug Design 80(2):245-253, Aug. 2012.
Lee, I., et al., "Ketal Containing Amphiphilic Block Copolymer Micelles as pH-Sensitive Drug Carriers," International Journal of Pharmaceutics 448(1):259-266, May 2013.

* cited by examiner

POLYMER COMPOSED OF REPEAT UNITS HAVING A BIOLOGICALLY ACTIVE MOLECULE ATTACHED THERETO VIA A PH-SENSITIVE BOND

INTRODUCTION

The present invention relates to a polymer comprising a particular repeat unit and a biologically active molecule such as a small molecule drug wherein the biologically active molecule is covalently bound to the repeat unit. The present invention also relates to particles comprising the polymer and to methods for making both the polymer and the particles. Additionally the present invention relates to pharmaceutical compositions and dosage forms comprising the polymer and/or the particles and to use of the polymer and the particles in medicine.

BACKGROUND

Polymers have been used in pharmaceutical compositions for many years for a variety of different reasons, including controlling the release rate of drug from the dosage form. Conventionally drugs are formulated in admixture with one or more polymers and the drug/polymer mixture is formed into dosage forms, e.g. tablets are formed by compounding. The drug is only released from the dosage form when the polymer is dissolved or degraded and hence the rate of drug release can be controlled, and specifically decreased.

More recently polymers have been used in the preparation of drug-polymer conjugates wherein the drug is covalently bound to the polymer. Two types of drug-polymer conjugate have been prepared, one wherein the drug forms part of the polymer backbone and one wherein the drug is attached to a preformed polymer backbone. U.S. Pat. No. 6,613,807 discloses an example of the former wherein a drug-polymer conjugate comprising a polyanhydride backbone additionally comprises at least one group that will provide a therapeutically active compound upon hydrolysis of the polymer. US2014/0046018 discloses an example of the latter wherein a biodegradable polymer comprises a releasable bioactive moiety as a side group of its repeat unit.

The provision of drug-polymer conjugates is not, however, straightforward and a number of challenges need to be overcome. Covalently attaching biologically active molecules to preformed polymer backbones can be difficult to do because of steric and thermodynamic problems. This can impact on the distribution of biologically active molecule within the polymer and it can be difficult to achieve a high concentration of biologically active molecule in the polymer. As a result it can be impossible to provide compositions with adequately high biologically active molecule loading. It can also be difficult to control the release rate profile of biologically active molecule-polymer conjugates because the release rate depends on the degradation of bonds within the polymer. Assuming, as is typically the case, that all the biologically active molecule in the polymer is attached by the same type of bond, a burst of biologically active molecule release occurs when conditions that hydrolyse that type of bond are encountered and thereafter much lower amounts of biologically active molecule are released.

Another problem encountered in modern medicine is that an increasing number of diseases require combination therapy, i.e. treatment with more than one biologically active molecule within a treatment protocol. This is particularly the case in the treatment of infectious diseases and in cancer treatment. The drugs utilised in combination therapy often have complimentary modes of action and/or have additive or synergistic therapeutic effects. The treatment protocols employing multiple drugs are, however, invariably complicated and intensive. Frequent drug dosing and concomitant administration of several different drugs at a given point in time is commonplace. Such complicated protocols tend to have lower patient compliance and tolerance than more straightforward protocols.

SUMMARY OF INVENTION

Viewed from a first aspect the present invention provides a polymer comprising: (i) a repeat unit derived from a compound of formula (I)

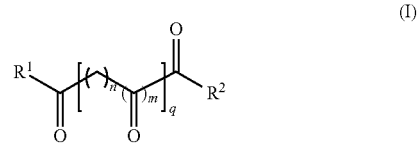

wherein,
$R^1$ and $R^2$ are each independently selected from OH, OR', SH, SR', $NH_2$, NHR' and $NR'_2$;
R' is $C_{1-20}$ hydrocarbyl;
each n is independently 0 or an integer between 1 and 6;
each m is independently 0 or an integer between 1 and 4, and preferably at least one m is 1; and
q is an integer between 1 and 8; and;
(ii) a biologically active molecule;
wherein said biologically active molecule is covalently bonded to said repeat unit.

A preferred polymer of the invention comprises a repeat unit of formula (III):

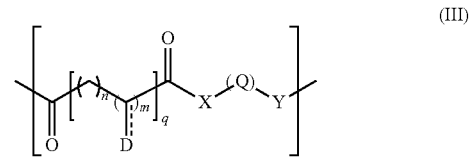

wherein
each n is independently 0 or an integer between 1 and 6;
each m is independently 0 or an integer between 1 and 4, and preferably at least one mist;
each D is a moiety which is said biologically active molecule, or a derivative thereof, when the C to D bond(s) is broken;
each q is an integer between 1 and 8;
X is selected from O, S, NH and NR';
Y is selected from O, S, NH and NR';
Q is selected from $-(CH_2)_p-$, $-(CH_2CH_2O)_sCH_2CH_2-$, $-(CH_2)_rNR'-(CH_2)_r-$ and $-(CH_2CH_2O)_s CH_2CH_2CH_2CH_2-$;
each of p and s is independently an integer between 1 and 16; and
R' is $C_{1-20}$ hydrocarbyl.

Viewed from a further aspect the present invention provides a method for making a polymer as hereinbefore defined comprising:
reacting a compound of formula (I)

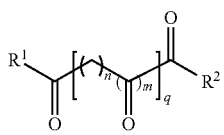

(I)

wherein, $R^1$ and $R^2$ are each independently selected from OH, OR', SH, SR', $NH_2$, NHR' and $NR'_2$;

R' is $C_{1-20}$ hydrocarbyl;

each n is independently 0 or an integer between 1 and 6;

each m is independently 0 or an integer between 1 and 4, and preferably at least one m is 1; and q is an integer between 1 and 8;

with a biologically active molecule.

Viewed from a further aspect the present invention provides a particle comprising a polymer as hereinbefore defined.

Viewed from a further aspect the present invention provides a method for making a particle as hereinbefore defined, wherein said method is selected from nanoprecipitation, emulsion-diffusion, double emulsification, emulsion-coacervation, polymer-coating and layer-by-layer method.

Viewed from a further aspect the present invention provides a particle comprising a polymer comprising repeat units of formula (I) and optionally formula (II) and an agent selected from a biologically active molecule, a molecular probe and a diagnostic agent which is non-covalently bound to said polymer.

Viewed from a further aspect the present invention provides a method for making a particle comprising a polymer comprising repeat units of formula (I) and optionally formula (II) and an agent selected from a biologically active molecule, a molecular probe and a diagnostic agent which is non-covalently bound to said polymer, wherein said method is selected from nanoprecipitation, emulsion-diffusion, double emulsification, emulsion-coacervation, polymer-coating and layer-by-layer method.

Viewed from a further aspect the present invention provides a pharmaceutical composition comprising a polymer as hereinbefore defined or a particle as hereinbefore defined.

Viewed from a further aspect the present invention provides a dosage form comprising a polymer as hereinbefore defined or a particle as hereinbefore defined.

Viewed from a further aspect the present invention provides a polymer as hereinbefore defined or a particle as hereinbefore defined for use in medicine, e.g. for use in the treatment of a disease selected from inflammatory diseases (e.g. inflammatory bowel disease, rheumatoid arthritis and artherosclerosis), metabolic disorders (e.g. diabetes, insulin resistance, obesity), cancer, bacterial infections (e.g. Tuberculosis, pneumonia, endocarditis, septicaemia, salmonellosis, typhoid fever, cystic fibrosis, chronic obstructive pulmonary diseases), viral infections, cardiovascular diseases, neurodegenerative diseases, neurological disorders, behavioral and mental disorders, blood diseases, chromosome disorders, congenital and genetic diseases, connective tissue diseases, digestive diseases, ear, nose, and throat diseases, endocrine diseases, environmental diseases, eye diseases, female reproductive diseases, fungal infections, heart diseases, hereditary cancer syndromes, immune system diseases, kidney and urinary diseases, lung diseases, male reproductive diseases, mouth diseases, musculoskeletal diseases, myelodysplastic syndromes, nervous system diseases, newborn screening, nutritional diseases, parasitic diseases, rare Cancers and skin diseases.

Viewed from a further aspect the present invention provides the use of a polymer as hereinbefore defined or a particle as hereinbefore defined in the manufacture of a medicament for the treatment of a disease selected from inflammatory diseases (e.g. inflammatory bowel disease, rheumatoid arthritis and artherosclerosis), metabolic disorders (e.g. diabetes, insulin resistance, obesity), cancer, bacterial infections (e.g. Tuberculosis, pneumonia, endocarditis, septicaemia, salmonellosis, typhoid fever, cystic fibrosis, chronic obstructive pulmonary diseases), viral infections, cardiovascular diseases, neurodegenerative diseases, neurological disorders, behavioral and mental disorders, blood diseases, chromosome disorders, congenital and genetic diseases, connective tissue diseases, digestive diseases, ear, nose, and throat diseases, endocrine diseases, environmental diseases, eye diseases, female reproductive diseases, fungal infections, heart diseases, hereditary cancer syndromes, immune system diseases, kidney and urinary diseases, lung diseases, male reproductive diseases, mouth diseases, musculoskeletal diseases, myelodysplastic syndromes, nervous system diseases, newborn screening, nutritional diseases, parasitic diseases, rare Cancers and skin diseases.

Viewed from a further aspect the present invention provides a method of treating a patient in need thereof, comprising administering to said patient a therapeutically effective amount of a polymer as hereinbefore defined or a particle as hereinbefore defined.

Viewed from a further aspect the present invention provides a polymer as hereinbefore defined or a particle as hereinbefore defined, wherein release of said biologically active molecule is dependent upon the nature of the bond between said biologically active molecule to which it is covalently bound.

Definitions

As used herein the term "polymer" refers to a compound comprising repeating units. Polymers usually have a polydispersity of greater than 1. Polymers generally comprise a backbone, side chains and termini. The backbone is the linear chain to which all side chains are pendant. The side chains are the groups that are pendant to the backbone or branch off the backbone. The termini are the ends of the backbone.

As used herein, the term "biologically active molecule" refers to any molecule that produces a local or systemic effect when administered to an animal, and preferably a human; preferably the local or systemic effect is a therapeutic activity, Preferred examples of biologically active molecules include the group consisting of small molecule drugs, peptides, proteins, peptide mimetics, antibodies, antigens, DNA, mRNA, small interfering RNA, small hairpin RNA, microRNA, PNA, foldamers, carbohydrates, carbohydrate derivatives, non-Lipinski molecules, synthetic peptides and synthetic oligonucleotides, and most preferred small molecule drugs.

As used herein the term "small molecule drug" refers to a chemical compound which has known biological effect on an animal, such as a human. Typically drugs are chemical compounds which are used to treat, prevent or diagnose a disease. Preferred small molecule drugs are biologically active in that they produce a local or systemic effect in animals, preferably mammals, more preferably humans. In certain preferred embodiments, the small molecule drug is referred to as a "drug molecule" or "drug". In certain embodiments, the drug molecule has $M_w$ less than or equal to about 5 kDa. In other embodiments, the drug molecule has $M_w$ less than or equal to about 1.5 kDa. A more complete, although not exhaustive, listing of classes and specific drugs suitable for use in the present invention may be found in "Pharmaceutical Substances: Syntheses, Patents, Applications" by Axel Kleemann and Jurgen Engel, Thieme Medical Publishing, 1999 and the "Merck Index: An Encyclopedia of Chemicals, Drugs, and Biologicals", edited by Susan Budavari et al., CRC Press, 1996, both of which are incorporated herein by reference.

As used herein, the term "peptides" refers to biologically occurring short chains of amino acid monomers linked by peptide (amide) bonds. The covalent chemical bonds are formed when the carboxyl group of one amino acid reacts with the amino group of another. The shortest peptides are dipeptides, consisting of 2 amino acids joined by a single peptide bond, followed by tripeptides, tetrapeptides, etc. A polypeptide is a long, continuous, and unbranched peptide chain. Hence, peptides fall under the broad chemical classes of biological oligomers and polymers, alongside nucleic acids, oligosaccharides and polysaccharides, etc.

As used herein the term "proteins" is distinguished from peptides n the basis of size, and as an arbitrary benchmark can be understood to contain approximately 50 or more amino acids.[1] Proteins consist of one or more polypeptides arranged in a biologically functional way, often bound to ligands such as coenzymes and cofactors, or to another protein or other macromolecule (DNA, RNA, etc.), or to complex macromolecular assemblies.

As used herein, the term "peptide mimetics" refers to small protein-like chains designed to mimic a peptide. They typically arise either from modification of an existing peptide, or by designing similar systems that mimic peptides, such as peptoids and β-peptides. Irrespective of the approach, the altered chemical structure is designed to advantageously adjust the molecular properties such as, stability or biological activity.

This can have a role in the development of drug-like compounds from existing peptides. These modifications involve changes to the peptide that will not occur naturally (such as altered backbones and the incorporation of non-natural amino acids).

As used herein, the term "antibodies" (also known as immunoglobulins (Ig)), are large, Y-shape proteins produced by plasma cells that are used by the immune system to identify and neutralize pathogens such as bacteria and viruses. The antibody recognizes a unique molecule of the harmful agent, called an antigen, via the variable region. Each tip of the "Y" of an antibody contains a paratope (analogous to a lock) that is specific for one particular epitope (similarly analogous to a key) on an antigen, allowing these two structures to bind together with precision. In addition to antibodies naturally produced by the body's own immune system, the term "antibodies" also encompasses antibodies that are artificially produced outside of the body to produce beneficial properties, e.g. monoclonal antibodies for use in the treatment of tumours.

As used herein, the term "antigen" is, as noted above, any harmful agent that causes the immune system of an animal body to produce an immune response, e.g. chemicals, bacteria, viruses or pollen.

As used herein the term "mRNA" refers to messenger RNA, a family of RNA molecules that convey genetic information from DNA to the ribosome, where they specify the amino acid sequence of the protein products of gene expression. Following transcription of primary transcript mRNA (known as pre-mRNA) by RNA polymerase, processed, mature mRNA is translated into a polymer of amino acids: a protein. As in DNA, mRNA genetic information is in the sequence of nucleotides, which are arranged into codons consisting of three bases each. Each codon encodes for a specific amino acid, except the stop codons, which terminate protein synthesis. This process of translation of codons into amino acids requires two other types of RNA: Transfer RNA (tRNA), that mediates recognition of the codon and provides the corresponding amino acid, and ribosomal RNA (rRNA), that is the central component of the ribosome's protein-manufacturing machinery.

As used herein, the term "small interfering RNA" refers to a class of double-stranded RNA molecules, 20-25 base pairs in length. siRNA plays many roles, but it is most notable in the RNA interference (RNAi) pathway, where it interferes with the expression of specific genes with complementary nucleotide sequences. siRNA functions by causing mRNA to be broken down after transcription, resulting in no translation. siRNA also acts in RNAi-related pathways, e.g. as an antiviral mechanism or in shaping the chromatin structure of a genome.

As used herein, the term "small hairpin RNA" refers to an artificial RNA molecule with a tight hairpin turn that can be used to silence target gene expression via RNA interference (RNAi). Expression of shRNA in cells is typically accomplished by delivery of plasmids or through viral or bacterial vectors. shRNA is an advantageous mediator of RNAi in that it has a relatively low rate of degradation and turnover.

As used herein, the term "micro RNA" refers to a small non-coding RNA molecule (containing about 22 nucleotides) found in plants, animals, and some viruses, which functions in RNA silencing and post-transcriptional regulation of gene expression.

As used herein the term "PNA" refers to Peptide nucleic acid, an artificially synthesized polymer similar to DNA or RNA invented by Peter E. Nielsen (Univ. Copenhagen), Michael Egholm (Univ. Copenhagen), Rolf H. Berg (Rise National Lab), and Ole Buchardt (Univ. Copenhagen) in 1991. PNA's backbone is composed of repeating N-(2-aminoethyl)-glycine units linked by peptide bonds. The various purine and pyrimidine bases are linked to the backbone by a methylene bridge (—CH 2-) and a carbonyl group (—(C=O)—).

As used herein, the term "DNA" refers to deoxyribonucleic acid and derivatives thereof, the molecule that carries most of the genetic instructions used in the development, functioning and reproduction of all known living organisms and many viruses. Most DNA molecules consist of two biopolymer strands coiled around each other to form a double helix. The two DNA strands are known as polynucleotides since they are composed of simpler units called nucleotides. Each nucleotide is composed of a nitrogen-containing nucleobase—either cytosine (C), guanine (G), adenine (A), or thymine (T)—as well as a monosaccharide sugar called deoxyribose and a phosphate group. The nucleotides are joined to one another in a chain by covalent bonds between the sugar of one nucleotide and the phosphate of the next, resulting in an alternating sugar-phosphate backbone. According to base pairing rules (A with T, and C with G), hydrogen bonds bind the nitrogenous bases of the two separate polynucleotide strands to make double-stranded DNA.

As used herein, the term "foldamer" refers to a discrete chain molecule or oligomer that folds into a conformationally ordered state in solution. They are artificial molecules that mimic the ability of proteins, nucleic acids, and polysaccharides to fold into well-defined conformations, such as helices and β-sheets. The structure of a foldamer is stabilized by noncovalent interactions between nonadjacent monomers.

As used herein, the term "carbohydrate" refers to biological molecule consisting of carbon (C), hydrogen (H) and oxygen (O) atoms, usually with a hydrogen:oxygen atom ratio of 2:1 (as in water); in other words, with the empirical formula $C_m(H_2O)_n$ (where m could be different from n). Some exceptions exist; for example, deoxyribose, a sugar component of DNA, has the empirical formula $C_5H_{10}O_4$. Carbohydrates are technically hydrates of carbon; structurally it is more accurate to view them as polyhydroxy aldehydes and ketones. The term is most common in biochemistry, where it is a synonym of saccharide, a group that includes sugars, starch, and cellulose. The saccharides are divided into four chemical groups: monosaccharides, disaccharides, oligosaccharides, and polysaccharides.

As used herein, the term "non-Lipinski molecules" refers to molecules that do not conform to Lipinski's rule of five also known as the Pfizer's rule of five or simply the Rule of five (RO5) is a rule of thumb to evaluate druglikeness or determine if a chemical compound with a certain pharmacological or biological activity has properties that would make it a likely orally active drug in humans. The rule was formulated by Christopher A. Lipinski in 1997, based on the observation that most orally administered drugs are relatively small and moderately lipophilic molecules. The rule describes molecular properties important for a drug's pharmacokinetics in the human body, including their absorption, distribution, metabolism, and excretion ("ADME"). However, the rule does not predict if a compound is pharmacologically active.

As used herein the term "particle" refers to a discrete form. Examples of particles include solid particles, micelles, polymersomes, nanospheres, microspheres, nanocapsules and microcapsules.

As used herein the term "acid-labile" refers to a bond which breaks in acidic conditions, e.g. a pH of <7.

As used herein the term "direct bond" means that there are no intervening atoms. Thus, for example, a direct bond between a repeat unit and a drug means that a functional group of the drug is attached to an atom of the repeat unit, i.e. without the use of a linking group in between.

As used herein the term "$C_{1-20}$ hydrocarbyl" covers any group comprising carbon and hydrogen. Optionally a hydrocarbyl group further comprises one or more heteroatoms, e.g. O, N or S. The heteroatom may, for example, interrupt the carbon chain and/or be present as a substituent on the group. Preferred hydrocarbyl groups consist of carbon and hydrogen. Examples of hydrocarbyl groups include alkyl, cycloalkyl, aryl and arylalkyl.

As used herein the term "alkyl" refers to saturated, straight chained, branched or cyclic groups. Alkyl groups may be substituted or unsubstituted.

As used herein the term "cycloalkyl" refers to a saturated or partially saturated mono- or bicyclic alkyl ring system containing 3 to 10 carbon atoms. Cycloalkyl groups may be substituted or unsubstituted.

As used herein the term "aryl" refers to a group comprising at least one aromatic ring. The term aryl encompasses heteroaryl as well as fused ring systems wherein one or more aromatic ring is fused to a cycloalkyl ring. Aryl groups may be substituted or unsubstituted.

As used herein the term "arylalkyl" or "aralkyl" refers to an alkyl group as hereinbefore defined that is substituted with an aryl group as hereinbefore defined.

Optional substituents that may be present on alkyl, cycloalkyl, aryl and arylalkyl groups include $C_{1-16}$ alkyl or $C_{1-16}$ cycloalkyl wherein one or more non-adjacent C atoms may be replaced with O, S, N, C=O and —COO—, substituted or unsubstituted $C_{5-14}$ aryl, substituted or unsubstituted $C_{5-14}$ heteroaryl, $C_{1-16}$ alkoxy, $C_{1-16}$ alkylthio, halo, e.g. fluorine and chlorine, cyano and arylalkyl.

As used herein the term "keto group" refers to a carbonyl group, wherein the carbon atom of the carbonyl is also bonded to two carbon atoms.

As used herein the term "hydrazine" refers to a group of the formula —NH—NH$_2$.

As used herein, the term "hydrazide" refers to a group of formule R'(CO)—NH—NH$_2$ wherein R' can, for example be H or hydrocarbyl.

As used herein the term "hydrazone" refers to a group of the formula =N—NH—.

As used herein the term "amine" refers to a group of the formula —NH$_2$, NHR or NR$_2$, wherein R is a hydrocarbyl group.

As used herein the term "imine" refers to a group of the formula =N—.

As used herein the term "hydroxyl" refers to a group of the formula —OH.

As used herein the term "ketal" refers to a group of the formula —C(OR)$_2$— wherein each R is hydrocarbyl or the two R groups together form a hydrocarbyl ring; As used herein the term "thiol" refers to a group of the formula —SH.

As used herein the term "thioketal" refers to a group of the formula —C(SR)$_2$— wherein each R is hydrocarbyl or the two R groups together form a hydrocarbyl ring.

As used herein the term "oxime" refers to a group of the formula =N—O—.

DESCRIPTION OF INVENTION

The present invention relates to a polymer comprising a repeat unit and a biologically active molecule such as a small molecule drug, wherein the biologically active molecule is covalently bound to the repeat unit. Advantageously this means that the biologically active molecule is not released until the covalent bond between the polymer and the biologically active molecule is broken, e.g. hydrolysed. The location of release of the biologically active molecule and the rate of release of the biologically active molecule can therefore be controlled by tailoring the nature of the bond between the polymer and the biologically active molecule.

The polymer of the present invention comprises:
(i) a repeat unit derived from a compound of formula (I)

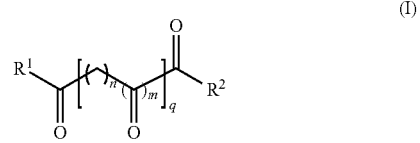

(I)

wherein,
$R^1$ and $R^2$ are each independently selected from OH, OR', SH, SR', NH$_2$, NHR' and NR'$_2$;
R' is $C_{1-20}$ hydrocarbyl;
each n is independently 0 or an integer between 1 and 6;
each m is independently 0 or an integer between 1 and 4, and preferably at least one m is 1; and
q is an integer between 1 and 8.

Preferred polymers of the invention further comprise a repeat unit derived from a compound of formula (II):

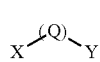
(II)

wherein
X is selected from OH, OR', SH, SR' NH$_2$, NHR' and NR'$_2$;
Y is selected from OH, OR', SH, SR', NH$_2$, NHR' and NR'$_2$
Q is selected from —(CH$_2$)$_p$—, —(CH$_2$CH$_2$O)$_s$CH$_2$CH$_2$—, —(CH$_2$)$_r$NR'—(CH$_2$)$_r$— and —(CH$_2$CH$_2$O)$_s$CH$_2$CH$_2$CH$_2$—; each of p, r and s is independently an integer between 1 and 16; and
R' is selected from C$_{1-20}$ hydrocarbyl.

In the polymers of the present invention q may be 1, 2, 3, 4, 5, 6, 7 or 8. Preferably, however, q is 1, 2 or 3, still more preferably 1 or 2 and particularly preferably 1. When q is an integer greater than 1, each n and m present in the compound of formula (I) may be the same or different.

Preferred polymers of the invention are derived from a compound of formula (I) wherein q is 1. Preferably therefore the polymers of the present invention are derived from a compound of formula (Ia):

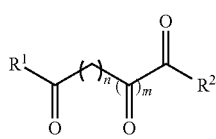
(Ia)

wherein R$^1$, R$^2$, R', n and m are as defined above in relation to formula (I).

The polymers of the present invention are derived from a compound of formula (I) or (Ia) wherein each m is 0, 1, 2, 3 or 4. Preferably at least one m is 1. This ensures that at least one keto group is present in the compound of formula (I) and (Ia). Preferably each m is 1 or 2 and still more preferably each m is 1. When m is 1, the keto groups are spaced apart by at least one carbon atom and it is believed that this avoids steric clashes between drugs once they are attached to the polymer.

The polymers of the present invention are derived from a compound of formula (I) or (Ia) wherein each n is 0, 1, 2, 3, 4, 5 or 6. Preferably each n is 1, 2 or 3, and still more preferably 1 or 2 and yet more preferably 2. The n groups spaces apart the keto groups and advantageously enables a relatively high amount of drug to be covalently bound to the polymer.

The polymers of the present invention are preferably derived from a compound of formula (I) or (Ia) wherein R$^1$ is OH or OR' wherein R' is as defined above in relation to formula (I). Still more preferably R$^1$ is OR'. Further preferred polymers of the present invention are derived from a compound of formula (I) or (Ia) wherein R$^2$ is OH or OR', wherein R' is as defined above in relation to formula (I). Still more preferably R$^2$ is OR'. R$^1$ and R$^2$ may be the same or different, but are preferably the same. Yet more preferably R$^1$ and R$^2$ are OR'.

When R$^1$ and/or R$^2$ comprise a R' group, R' is preferably a C$_{1-20}$ alkyl, more preferably a C$_{1-12}$ alkyl, yet more preferably a C$_{1-8}$ alkyl and especially preferably a C$_{1-6}$ alkyl. Representative examples of suitable alkyl groups include methyl, ethyl, propyl, butyl, pentyl and hexyl. Methyl is a particularly preferred alkyl group.

The polymers of the present invention are preferably derived from a compound of formula (II) wherein X is OH or OR' wherein R' is as defined above in relation to formula (II). Still more preferably X is OH. Further preferred polymers of the present invention are derived from a compound of formula (II) wherein Y is OH or OR', wherein R' is as defined above in relation to formula (II). Still more preferably Y is OH. X and Y may be the same or different, but are preferably the same. Yet more preferably X and Y are both OH.

The polymers of the present invention are preferably derived from a compound of formula (II) wherein Q is —(CH$_2$)$_p$—. The polymers of the present invention are preferably derived from a compound of formula (II) wherein p is an integer between 2 and 14, more preferably 4 and 12 and yet more preferably 6 and 10.

When Q is —(CH$_2$CH$_2$O)$_s$CH$_2$CH$_2$— or —(CH$_2$CH$_2$CH$_2$O)$_s$CH$_2$CH$_2$CH$_2$—, s is preferably an integer from 2 and 14, more preferably from 4 to 12 and yet more preferably from 6 to 10. In this case the compound of formula (II) is a polyethyleneglycol (PEG) or a polypropylene glycol.

When Q is —(CH$_2$)$_r$NR'—(CH$_2$)$_r$—, each r is preferably an integer of from 2 to 12 and each r can be the same or different. More preferably, r is from 2 to 8 and yet more preferably from 2 to 6.

Particularly preferably the polymers of the present invention are derived from dimethyl-2-oxo-glutarate or dimethyl-3-oxo-glutarate. Yet more preferably the polymers of the present invention are also derived from 1,8-octanediol, triethylene glycol or N-methyldiethanolamine.

One group of preferred polymers of the present invention comprise a repeat unit of formula (III):

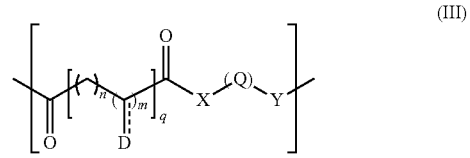
(III)

wherein
each n is independently 0 or an integer between 1 and 6;
each m is independently 0 or an integer between 1 and 4, and preferably at least one m is 1;
each D is a moiety which is said biologically active molecule, or a derivative thereof, when the C to D bond(s) is broken;
--- is a bond which may be present or absent;
each q is an integer between 1 and 8;
X is selected from O, S, NH and NR';
Y is selected from O, S, NH and NR';
Q is selected from —(CH$_2$)$_p$—, —(CH$_2$CH$_2$O)$_s$CH$_2$CH$_2$—, —(CH$_2$)$_r$NR'—(CH$_2$)$_r$ and —(CH$_2$CH$_2$O)$_s$CH$_2$CH$_2$CH$_2$CH$_2$—;
each of p, r and s is independently an integer between 1 and 16; and
each R' is selected from C$_{1-20}$ hydrocarbyl.

In compounds of formula (III) the dashed bond may be present or absent.

When it is absent there is a single bond between C and D. When it is present there may be a double bond between C and D or two single bonds between C and D.

Preferred values for each of n, m, q, X, Y, R', Q, p and s are as set out above in relation to each of formulae (I), (Ia) and (II). Preferably the dashed bond is present. Preferably it is a part of a double bond. Preferred polymers of the invention therefore comprise a repeat unit of formula (III-i) wherein q is 1:

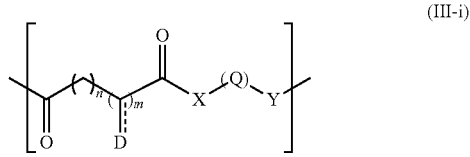

(III-i)

wherein n, m, D, X, Y, R', Q, p and s are as defined above in relation to formula (III).

In polymers of formula (III) and (III-i) D is formed by the biologically active molecule (e.g. a drug). Thus D is the moiety derived from the biologically active molecule (e.g. a drug) once it forms a covalent bond to the repeat unit. When the bond between the repeat unit and D is broken, i.e the C-D bond in formulae (III) and (III-i), D becomes the biologically active molecule or an active form, e.g. derivative, of the biologically active molecule.

In preferred polymers comprising a repeat unit of formula (III) or (III-i), the bond(s) between the repeat unit and D is acid-labile. Preferably the bonds are hydrolysed in the acidic and/or hydrolytic environment of cell compartments such as lysosome, endosome, phagosome, phagolysosome and autophagosome found in various cells such as macrophages. Preferably the bond(s) between the repeat unit and D is hydrolysed in a pH of <6 and still more preferably in a pH of <5. The hydrolysis of the bond releases the biologically active molecule (e.g. a drug), D.

In preferred polymers comprising a repeat unit of formula (III) or (III-i), the bond(s) between the repeat unit and D is direct. More preferably the bond between the repeat unit and D is a double bond.

Preferably there are no linking atoms or functional groups between the repeat unit and the biologically active molecule (e.g. a drug), D. Preferably the biologically active molecule (e.g. a drug) comprises a functional group that is able to form a covalent bond with a keto group present in the repeat unit of formula (III) or (III-i). More preferably the (e.g. a drug) comprises at least one hydrazine group, at least one hydrazide group, at least one amine group, at least one aminooxy group, at least one, preferably two, hydroxyl groups or at least one, preferably two, thiol groups.

In particularly preferred polymers of the invention the drug comprises at least one hydrazide group and the bond between the repeat unit and D is a hydrazone. Preferably therefore the polymer comprises a repeat unit of formula (IIIa)

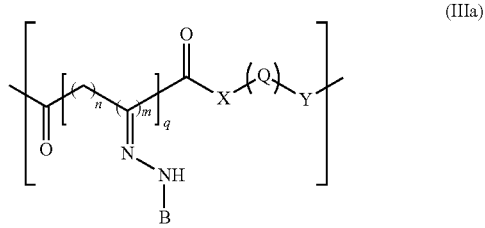

(IIIa)

wherein n, m, q, X, Y, R', Q, p and s are as defined above in relation to formula (III) and B is the remainder of D, i.e. the remainder of the biologically active molecule (e.g. a drug) that is attached to the hydrazide. Preferred values for each of n, m, q, X, Y, R', Q, p and s are as set out above in relation to each of formulae (I), (Ia) and (II). When the biologically active molecule is released by hydrolysis of the C=N bond in vivo, the biologically active molecule is B—NHNH$_2$. Advantageously the hydrazone bond hydrolyses at a pH of <6.

In preferred polymers comprising a repeat unit of formula (IIIa) the biologically active molecule is drug is selected from isoniazid, carbidopa, endralazine, dihydralazine, hydralazine, Hydracarbazine, Pheniprazine, Pildralazine, Octamoxin, a synthetic peptide, a synthetic oligonucleotide, a carbohydrate, a peptide mimetic, an antibody and hydrazine. Particularly preferably the drug is isoniazid.

In other particularly preferred polymers of the invention the biologically active molecule comprises at least one amine group and the bond between the repeat unit and D is an imine. Preferably therefore the polymer comprises a repeat unit of formula (IIIb):

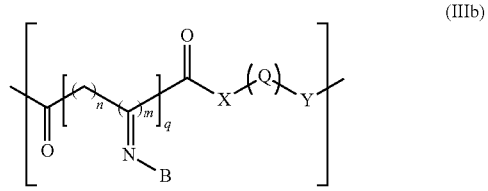

(IIIb)

wherein n, m, q, X, Y, R', Q, p and s are as defined above in relation to formula (III) and B is the remainder of D, i.e. the remainder of the biologically active molecule that is attached to the imine. Preferred values for each of n, m, q, X, Y, R', Q, p and s are as set out above in relation to each of formulae (I), (Ia) and (II). When the biologically active molecule is released by hydrolysis of the C=N bond in vivo, the drug is B—NH$_2$.

In preferred polymers comprising a repeat unit of formula (IIIb) the biologically active molecule is selected from a Alteplase, Adalimumab, Bivalirudin, Chloroprocaine, Daptomycin, Doxazosin, Efavirenz, Hydroflumethiazide, Indapamide, Insulin Detemir, Lisinopril, peptide mimetics, Prazosin, Saxagliptin, small interfering RNA, Sulfamethylthiazole, Sulfametrole, Sulfisomidine, Tripamide, 2-p-Sulfanilylanilinoethanol, 3-Amino-4-hydroxybutyric Acid, 3-Aminopyridine-2-carboxaldehyde thiosemicarbazone (3-AP)/3-Aminopyridine-4-methyl-2-carboxaldehyde thiosemicarbazone (3-AMP/Triapine/OCX-191/OCX-0191), 4, 4'-Sulfinyldianiline, 4'-(Methylsulfamoyl)sulfanilanilide, 4'-Sulfanilylsulfanilamide, 4-Amino-3-hydroxybutyric Acid, 4-Sulfanilamidosalicylic acid, 5-Hydroxytryptophan, 6-Diazo-5-oxo-L-norleucine (DON), 9-Aminoacrindine, 9-Aminocamptothecin, Abacavir, Abatacept, Acediasulfone, Acetosulfone sodium, Acyclovir, Adefovir, Alfuzosin, Amantadine, Amfenac, Amidinomycin, Amikacin, Aminolevulinic Acid, Amlodipine, Amoxicillin, Amphetamine, Amphomycin, Amphotericin B, Ampicillin, Amprenavir, Ancitabine, antibodies, antigens, Arbekacin, Aspoxicillin, Azacitidine, Azaserine, Bacampicillin, Bacitracin, BenexateHCl, Benserazide, Benzocaine, Benzylsulfamide, Bevacizumab, Bleomycins, Brodioprim, Bropirimine, Bunazosin, Butirosin, Capreomycin, carbohydrates, Carboplatin, Carubicin, Carumonam, Caspofungin, Cefaclor, Cefadroxil, Cefatrizine, Cefcapene, Cefclidin, Cefdinir, Cefditoren, Cefepime, Cefetamet, Cefinenoxime, Cefixime, Cefminox, Cefodizime, Ceforanide, Cefoselis, Cefotaxime, Cefotiam, Cefozopran, Cefpirome, Cefpodoxime, Cefprozil, Cefroxadine, Ceftazidime, Cefteram, Ceftibuten, Ceftizoxime, Ceftriaxone, Cefuzonam, Celecoxib, Cephalexin, Cephaloglycin, Cephalosporin C, Cephradine, Certolizumab, Cetoxime, Cetraxate, Cetuximab, Chlorproguanil, Cidofovir, Cilastatin, Cladribine, Clinafloxacin, Clopamide, Colesevelam, Colistin, Cyclacillin, Cycloguanil, Cyclopenthiazide, Cycloserine, Cytarabine, Dapsone, Darbepoetin Alfa, Darunavir, Daunorubicin, Decitabine, Denosumab, Dextroamphetamine, Dezocine, Dibekacin, Dideoxyadenosine, Disoproxil, DNA, Dornase Alfa, Doxorubicin, Doxycycline, Ebrotidine, Edatrexate, Eflornithine, Emtricitabine, Entecavir, Enviomycin, Epicillin, Epinastine, Epirubicin, Epoetin Alfa, Etanercept, Ethambutol, Exenatide, Famciclo Imiquimodvir, Famotidine, Filgrastim, Fingolimod, Flucytosine, Fluvoxamine, foldamers, Folic acid, Forimicins, Gabapentin, gama-Aminobutyric acid, Gemcitabine, Gemifloxacin, Gentamicin, Glatiramer Acetate, Golimumab, Histamine, Human Papilloma Quadrivalent, Hydrochlorothiazide, Idarubicin, Immune Globulin, Infliximab, Insulin Aspart, Insulin Glargine, Insulin Lispro, Interferon beta-1a, Interferon beta-1b, Ipilimubab, Irsogladine, Isepamicin, Kanamycin(s), Lamivudine, Lamotrigine, Lanreotide, L-DOPA, Lenalidomide, Lenampicillin, Levodopa, Levothyroxine, Liraglutide, Lisdexamfetamine, Loracarbef, Lymecycline, Mafenide, Mantadine, Meclocycline, Melphalan, Memantine, Mesalamine, Mesalazine, Metformin, Methacycline, Methotrexate, Methyl Aminolevulinate, Methyldopa, Miboplatin, Micronomicin, microRNA, Mikamycin, Milnacipran, Minocycline, Mitoguazone, Morphazinamide, mRNA, N4-beta-D-Glucosylsulfanilamide, Natalizumab, Natamycin, Negamycin, Neomycin, Netilmicin, Nimustine, Nolatrexed, Nomifensine, Non-Lipinski molecules, Noprysulfamide, N-Sulfanilyl-3, 4-xylamide, Nystatin, Ocreotide Acetate, Omalizumab, Oseltamivir, Oxaliplatin, Palivizumab, p-Aminosalicylic acid, p-Aminosalicylic acid hydrazide, Paromomycin, Parsalmide, Pazufloxacin, Pegfilgrastim, Peginterferon alfa-2a, Pemetrexed, Penciclovir, Peplomycin, Peptide, Protein, Pexiganan, Phenyl aminosalicylate, Picloxydine, Pirarubicin, Piritrexim, Pivampicillin, Pivcefalexin, pivoxil, PNA, Polymyxin, Pralatrexate, Pregabalin, Pregabelin, Primaquine, Procaine, Proparacaine, Propoxycaine, Proxetil, p-Sulfanilylbenzylamine, Puromycin, pyrimethamine, Quinocide, Ramoplanin, Ranibizumab, Regadenoson, Remacemide, Resiquimod, Ribostamycin, Rimantadine, Ristocetin, Rituximab, Rotraxate, S-Adenosylmethionine, Salacetamide, Sampatrilat, Sevelamer, Sisomicin, Sitafloxacin, Sitagliptin, small hairpin RNA, S-Methylmethionine, Somatropin, Sparfloxacin, Streptonigrin, Succisulfone, Suclofenide, Sulfabenzamide, Sulfacetamide, Sulfachlorpyridazine, Sulfachrysoidine, Sulfacytine, Sulfadiazine, Sulfadicramide, Sulfadimethoxine, Sulfadoxine, Sulfaethidole, Sulfaguanidine, Sulfaguanole, Sulfalene, Sulfamerazine, Sulfameter, Sulfamethazine, Sulfamethizole, Sulfamethoxazole, ulfamethoxypyridazine, Sulfamidochrysoidine, Sulfamoxole, Sulfanilamide, Sulfanilic acid, Sulfanilylurea, Sulfaperine, Sulfaphenazole, Sulfaproxyline, Sulfapyrazine, Sulfasomizole, Sulfasymazine, Sulfathiazole, Sulfathiourea, Sulfatolamide, Sulfisoxazole, Sulfonamide, Sulframethomidine, Sultamicillin, Sulthiame, synthetic oligonucleotides, synthetic peptide, Tafenoquine, Talampanel, Talampicillin, Teicoplanin, Tenofovir, Terazosin, Teriparatide, Tetroxoprim, Thiamiprine, Thioguanine, Tigemonam, Tinoridine, Tirapazamine, Tobramycin, Topiramate, Tosufloxacin, Tranylcypromine, Trastuzumab, Trimazosin, Trimethoprim, Trimetrexate, Tritoqualine, Trovafloxacin, Troxacitabine, Tuberactinomycin, Tubercidin, Tyrocidine, Ustekinumab, Valacyclovir, Valdecoxib, Valganciclovir, Vancomycin, Vidarabine, Vigabatrin, Vindesine, Viomycin, Zalcitabine and Zonisamide.

In other particularly preferred polymers of the invention the biologically active molecule such as a small molecule drug comprises at least two hydroxyl groups and the bonds between the repeat unit and D form a ketal. Other particularly preferred polymers of the invention comprise two biologically active molecules, each comprising at least one hydroxyl group, and the bonds between the repeat unit and D form a ketal. Preferably therefore the polymer comprises a repeat unit of formula (IIIci) or (IIIcii):

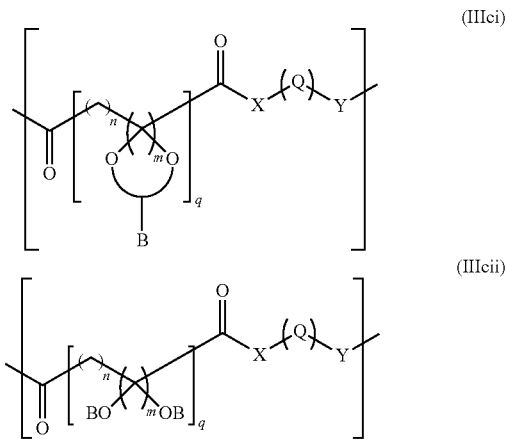

wherein n, m, q, X, Y, R', Q, p and s are as defined above in relation to formula (III) and B is the remainder of D, i.e. the remainder of the biologically active molecule that is attached to the OH functional group(s). Preferred values for each of n, m, q, X, Y, R', Q, p and s are as set out above in relation to each of formulae (I), (Ia) and (II).

In preferred polymers comprising a repeat unit of formula (IIIc) the biologically active molecule is selected from 2,4,6-Tribromo-m-cresol, 21-Acetoxypregnenolone, 2-p-Sulfanilylanilinoethanol, 3-Amino-4-hydroxybutyric Acid, 4-Amino-3-hydroxybutyric Acid, 4-Hexylresorcinol, 4-Sulfanilamidosalicylic acid, 5-(methylamino)-2-deoxyuridine (MADU), 5-Bromosalicylhydroxamic acid, 5-Hydroxytryptophan, 9-Aminocamptothecin, Abacavir, Abatacept, Abiraterone, Acebutolol, Acetaminophen, Acetaminosalol, Aclacinomycins, Acyclovir, Adalimumab, Ajmaline, Alclometasone, alfa-Bisabolol, all erythromycin ester derivatives, Alprenolol, Alteplase, Aluminum bis(acetylsalicylate), Amikacin, Aminochlorthenoxazin, Aminopropylon, amodiaquine, Amosulalol, Amoxicillin, Amprenavir, Ancitabine, Anidulafungin, Anileridine, Anthramycin, antibodies, antigens, Apalcillin, Apicycline, Arbekacin, Arotinolol, Artemisinin alcohol, Arzoxifene, Aspoxicillin, Atazanavir, Atenolol, Atrolactamide, Azacitidine, Azidamfenicol, Azithromycin, Bambermycins, Batimastat, Bebeerines, Beclomethasone Dipropionate, Befloxatone, Benserazide, Benzoylpas, Benzylmorphine, Betamethasone, Betaxolol, Bevacizumab, Biapenem, Bimatoprost, Bisoprolol, Bleomycins, Bosentan, Bromosalicylchloranilide, Broxuridine, Bucetin, Bucindolol, Budesonide, Bufeniode, Bufexamac, Bunitrolol, Bupranolol, Buprenorphine, Bupropion, Buramate, Buserelin, Butirosin, Butofilolol, Butorphanol, Cadralazine, Calusterone, Capecitabine, Capreomycin, Capsaicine, Carazolol, Carbidopa, carbohydrates, Carbomycin, Carteolol, Carubicin, Carvedilol, Caspofungin, CC-1065, Cefadroxil, Cefamandole, Cefatrizine, Cefbuperazone, Cefonicid, Cefoperazone, Cefoselis, Cefpiramide, Cefprozil, Celiprolol, Cephapirin sodium, Certolizumab, Cetuximab, Chloramphenicol, Chlorobutanol, Chloroxylenol, Chlorozotocin, Chlorphenesin, Chlorquinadol, Chlortetracycline Dalfopristin, Chromomycins, Cicletanine, Ciclopirox, Ciclosporine, Cidofovir, Cinchonidine, Cinchonine, Ciramadol, Cladribine, Clarithromycin, clavulanic acid, Clindamycin, Clobetasone, Clofoctol, Clomocycline, Cloxyquin, Codeine, Colesevelam, Colistin, Cyclosporin, Cytarabine, Darbepoetin Alfa, Darunavir, Dasatinib, Daunorubicin, Decitabine, Deflazacort, Delmostatin, Demeclocycline, Denosumab, Deoxydihydrostreptomycin, Desomorphine, Desonide, Desoximetasone, Desvenlafaxine, Dexamethasone, Dezocine, Diathymosulfone, Dibekacin, Didanosine, Dideoxyadenosine, Diethylstilbestrol, Diflorasone, Diflucortolone, Diflunisal, Gentisic acid, Difluprednate, Dihydroartemisinin, Dihydrocodeine, Dihydromorphine, Dihydrostreptomycin, Dihydroxyaluminum acetylsalicylate, Dilevalol, Dimepheptanol, Dirithromycin, Ditazol, DNA, Docetaxel, Dornase Alfa, Doxifluridine, Doxorubicin, Doxycycline, Droloxifene, Dromostanolone, Ecteinascidins, Edoxudine, Emtricitabine, Enocitabine, Enoxaparin, Enoxolone, Enprostil, Entacapone, Entecavir, Enviomycin, Epanolol, Epinephrine, Epirubicin, Epitiostanol, Epoetin Alfa, Eptazocine, Ertapenem, Erythromycin, Estramustine, Etanercept, Etanidazole, Ethinyl Estradiol, Ethoxazene, Ethylmorphine, Etofenamate, Etonogestrel, Etoposide, Eugenol, Everolimus, Exenatide, Ezetimibe, Fendosal, Fenoldopam Fenpentadiol, Fenretinide, Fepradinol, Fexofenadine, Filgrastim, Filipin, Flavopiridol, Flipirtine, Floctafenine, Flomoxef, Floxuridine, Fluazacort, Fluconazole, Fludrocortisone, Flumethasone, Fluocinolone, Fluocinonide, Fluocortin Butyl, Fluocortolone, Fluprednidene Acetate, Fluticasone Propionate, foldamers, Forimicins, Formestane, Formoterol, Foscarnet sodium, Fosfestrol, Fropenem, Fulvestrant, Fungichromin, Furonazide, Fusidic acid, Galantamine, Ganciclovir, Gemcitabine, Gentamicin, Glafenine, Glucametacin, Glucosulfone sodium, Glyconiazide, Golimumab. Balsalazide, Goserelin, Gramicidin(s), Guamecycline, Halcinonide, Halobetasol Propionate, Halofantrine, Halometasone, Halopredone Acetate, Human Papilloma Quadrivalent, Hydrocortisone, Hydromorphone, Hydroxypethidine, Hypericin, Ibuproxam, Idarubicin, Idoxuridine, Imipenem, Immune Globulin, Indenolol, Indinavir, Infliximab, Insulin Aspart, Insulin Detemir, Insulin Glargine, Insulin Lispro, Interferon beta-1a, Interferon beta-1b, Ipilimubab, Ipratropium, Irinotecan, Isepamicin, Isoxicam, Kanamycin(s), Kethoxal, Ketobemidone, Labetalol, Lamivudine, Latanoprost, L-DOPA, Leuprolide, Levcromakalim, Levodopa, Levonorgestrel, Levorphanol, Levothyroxine, Lincomycin, Liraglutide, Lopinavir, Lornoxicam, Losartan, Loteprednol Etabonate, Lumefantrine, Lymecycline, Mannomustine, Marimastat, Mazipredone, Meclocycline, Mefloquine, Melengestrol, Meloxicam, Memetasone, Menogaril, Mepindolol, Meptazinol, Merbromin, Meropenem, Mesalamine, Mesalazine, Metazocine, Methacycline, Methyldopa, Methylprednisolone, Metipranolol, Metopon, Metoprolol, Metronidazole, Micronomicin, microRNA, Mikamycin, Miltefosine, Minocycline, Misoprostol, Mitobronitol, Mitolactol, Mitoxantrone, Mometasone Furoate, Montelukast, Mopidamol, Moprolol, Morphine, Moxalactam, mRNA, N4-beta-D-Glucosylsulfanilamide, Nadifloxacin, Nadolol, Naftopidil, Nalbuphine, Natalizumab, Nebivolol, Negamycin, Nelfinavir, Neomycin, Netilmicin, N-Hydroxyethylpromethazine Chloride, Nifurpirinol, Nifurtoinol, Nitracrine, Nitroxoline, Nogalamycin, non-Lipinski molecules, Nordihydroguaiaretic Acid, Norlevorphanol, Normorphine, Novobiocin, Oleandomycin, Olivomycins, Olmesartan, Olsalazine, Omalizumab, Opipramol, Ornoprostil, Oryzanol A. Ganaxolone, Oxaceprol, Oxametacine, Oxycodone Pentazocine, Oxycodone, Oxymorphone, Oxyphenbutazone, Oxytetracycline, Paclitaxel and other known paclitaxel analogs, Paclitaxel, Paliperidone Palmitate, Paliperidone, Palivizumab, p-Aminosalicylic acid hydrazide, p-Aminosalicylic acid, Panipenem, Paromomycin, Pecilocin, Pegfilgrastim, Peginterferon alfa-2a, Penbutolol, Penciclovir, Pentostatin, Peplomycin, peptide mimetics, peptide, Perisoxal, Phenactropinium chloride, Phenazocine, Phenazopyridine, Phenocoll, Phenoperidine, Phentolamine, Phenyl aminosalicylate, Phenylramidol, Phenylsalicylate, Pildralazine, Pimecrolimus, Pindolol, Pipacycline, Pirarubicin, Piroxicam, p-Lactophenetide, Plaunotol, Plicamycin, PNA, Podophyllotoxin, Polymyxin, Posaconazole, Prednisolone, Prednisone, Primycin, Pristinamycin, Propranolol, protein, Protoveratrines, Puromycin, Pyrisuccideanol, Quetiapine, Ezetimibe, Quinine, Quinupristin, Raloxifene, Raltegravir, Ramoplanin, Ranibizumab, Ranimustine, Ranolazine, Ravuconazole, Rescimetol, Resiquimod, Retinoic acid (including all trans-retinioc acid), Ribavirin, Ribostamycin, Rifabutin, Rifalazil, Rifamide, Rifampicin, Rifamycin SV, Rifapentine, Rifaximin, Rimexolone, Rioprostil, Risedronic Acid, Ristocetin, Ritipenem, Ritonavir, Rituximab, Rolitetracycline, Roquinimex, Rosaprostol, Roxarsone, Roxindole, Roxithromycin, Rubijervine, Rubitecan, S-Adenosylmethionine, Salazosulfadimidine, Salicin, Tramadol, Salicylamide, Salicylanilide, Salinazid, Salmeterol, Salsalate, Sampatrilat, Sancycline, Saquinavir, Saxagliptin, Seocalcitol, Sevelamer, Siccanin, Simvastatin, Sirolimus, Sisomicin, small hairpin RNA, small interfering RNA, Somatropin, Sorivudine, Spectinomycin, Stavudine, Streptolydigin, Streptomycin, Streptonicozid, Streptozocin, Sulfasalazine, Sulfinalol, synthetic oligonucleotides, synthetic peptide, Tacrolimus, Tacrolimus. Talinolol, Teicoplanin, Telithromycin. Temoporfin, Teniposide, Tenoxicam, Tenuazonic Acid, Terfenadine, Teriparatide, Terofenamate, Tertatolol, Testosterone, Thiamphenicol, Thiostrepton, Tiazofurin, Timolol, Tiotropium, Tipranavir, Tobramycin, Tolcapone, Toloxatone, Tolterodine, Topotecan, Trans-Resveratrol [(E)-3,4',5-trihydroxystilbene), Trastuzumab, Travoprost, Triamcinolone, Trifluridine, Trimazosin, Trimoprostil, Trospectomycin, Troxacitabine, Tuberactinomycin, Tyrocidine, Ustekinumab, Valdecoxib, Valganciclovir, Valrubicin, Vancomycin, Venlafaxine, Vidarabine, Viminol, Vinblastine, Vincristine, Vindesine, Viomycin, Virginiamycin, Voriconazole, Xanthocillin, Xibomol, Ximoprofen, Yingzhaosu A, Zalcitabine, Zanamivir, Zidovudine, Zoledronic Acid, Zolendronic Acid, Zorubicin and Zosuquidar.

In other particularly preferred polymers of the invention the biologically active molecule such as a small molecule drug comprises at least two thiol groups and the bonds between the repeat unit and D form a thioketal. Other particularly preferred polymers comprise two biologically active molecules, each comprising at least one thiol group, and the bonds between the repeat unit and D form a thioketal. Preferably therefore the polymer comprises a repeat unit of formula (IIIdi) or (IIIdii):

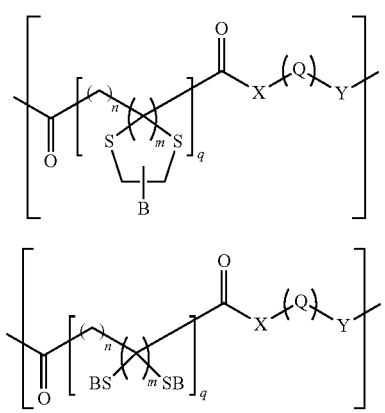

(IIIdi)

(IIIdii)

wherein n, m, q, X, Y, R', Q, p and s are as defined above in relation to formula (III). Preferred values for each of n, m, q, X, Y, R', Q, p and s are as set out above in relation to each of formulae (I), (Ia) and (II). B is the remainder of D, i.e. the remainder of the biologically active molecule that is attached to the dithiol group.

In preferred polymers comprising a repeat unit of formula (IIId) the biologically active molecule is selected from peptide, protein, carbohydrate, peptide mimetic, antibody, antigen, synthetic oligonucleotide, Adalimumab, Etanercept, Pegfilgrastim, Rituximab, Bevacizumab, Insulin Glargine, Epoetin Alfa, Trastuzumab, Interferon beta-1a, Ranibizumab, Insulin Detemir, Insulin Aspart, Insulin Lispro, Filgrastim, Darbepoetin Alfa, Interferon beta-1b, Abatacept, Liraglutide, Palivizumab, Cetuximab, Ustekinumab, Denosumab, Human Papilloma Quadrivalent, Peginterferon alfa-2a, Ipilimubab, Immune Globulin, Dornase Alfa, Certolizumab, Natalizumab, Somatropin, Alteplase and Golimumab.

In other particularly preferred polymers of the invention the biologically active molecule comprises at least one aminooxy group and the bond between the repeat unit and D form an oxime. Preferably therefore the polymer comprises a repeat unit of formula (IIIe):

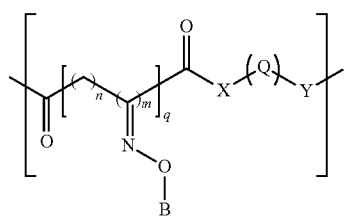

(IIIe)

wherein n, m, q, X, Y, R', Q, p and s are as defined above in relation to formula (III). Preferred values for each of n, m, q, X, Y, R', Q, p and s are as set out above in relation to each of formulae (I), (Ia) and (II). B is the remainder of D, i.e. the remainder of the biologically active molecule that is attached to the oxime group.

Especially preferred polymers of the present invention comprise a repeat unit of formula (IIIa).

Another preferred group of polymers of the present invention comprise a unit of formula (IVa) or (IVb):

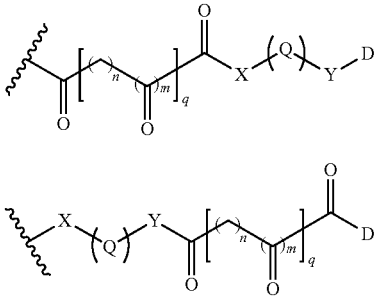

IVa

IVb wherein
each n is independently 0 or an integer between 1 and 6;
each m is independently 0 or an integer between 1 and 4, and preferably at least one m is 1;
each q is an integer between 1 and 8;
X is selected from O, S, NH and NR';
Y is selected from O, S, NH and NR';
Q is selected from $-(CH_2)_p-$, $-(CH_2CH_2O)_sCH_2CH_2-$, $-(CH_2)_rNR'-(CH_2)_r-$ and $-(CH_2CH_2O)_sCH_2CH_2CH_2CH_2-$;
each of p, r and s is independently an integer between 1 and 16;
R' is $C_{1-20}$ hydrocarbyl; and
D is a moiety which is said biologically active molecule, or a derivative thereof, when the Y to D bond is broken.

Preferred values for each of n, m, q, X, Y, R', Q, p and s are as set out above in relation to each of formulae (I), (Ia) and (II). Preferred polymers of the invention therefore comprise a unit of formula (IVa-i) or (IVb-i) wherein q is 1:

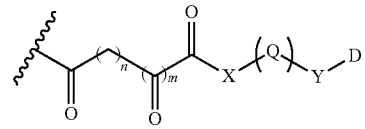

IVai

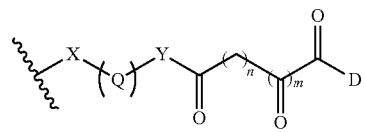

IVbi wherein n, m, D, X, Y, R', Q, p and s are as defined above in relation to formula (IV).

In polymers of formula (IV) D is formed by the biologically active molecule such as a small molecule drug. Thus D is the moiety derived from the biologically active molecule once it forms a covalent bond to the unit. When the bond between the unit and D is broken, i.e the Y-D bond in formulae (IV), D becomes the biologically active molecule or an active form, e.g. derivative, of the biologically active molecule.

In preferred polymers comprising a unit of formula (IV), the bond between the unit and D is acid-labile. Preferably the bonds are hydrolysed in the acidic and/or hydrolytic environment of cell compartments such as lysosome, endosome, phagosome, phagolysosome and autophagosome found in various cells such as macrophages. Preferably the bond(s) between the unit and D is hydrolysed in a pH of <6 and still more preferably in a pH of <5. The hydrolysis of the bond releases the biologically active molecule such as a small molecule drug, D.

In preferred polymers comprising a unit of formula (IV), the bond between the unit and D is direct. Preferably there are no linking atoms or functional groups between the unit and the biologically active molecule, D. Preferably the biologically active molecule comprises a functional group that is able to form a covalent bond with the X, Y and/or keto moiety present in the unit of formula (IV). More preferably the biologically active molecule comprises a functional group selected from a carboxylic acid group, a carboxylic ester group, a carboxylate group, a carboxyl thioester group, an acyl phosphate group, a carboxylic acid anhydride group, a hydroxyl group, an acyl halide group, an amine group and a thiol group. Suitable biologically active molecule comprising hydroxyl and amine groups are those set out hereinbefore. Suitable biologically active molecules comprising carboxylic acid or carboxylic ester groups include 3-Amino-4-hydroxybutyric Acid, 4-Amino-3-hydroxybutyric Acid, 4-Sulfanilamidosalicylic acid, 5-Bromosalicylic acid acetate, 5-Hydroxytryptophan, 6-Diazo-5-oxo-L-norleucine (DON), Abacavir, Abatacept, Abiraterone, Aceclofenac, Acediasulfone, Acemetacin, Acetamidocaproic Acid, Acetaminophen, Acetoxolone, Acetylsalicylsalicylic acid, Acrivastine, Actarit, Adalimumab, Alacepril, Alclofenac, Alminoprofen, Alteplase, Amdinocillin, Amfenac, Amineptine, Aminolevulinic Acid, Amlodipine, Amoxicillin, Amphetamine, Amphomycin, Amphotericin B, Ampicillin, antibodies, Antidiabetic, antigens, Apalcillin, Apicycline, Arteflene, Artesunate, Aspirin, Aspoxicillin, Atazanavir, Atomoxetine, Atorvastatin, Azacitidine, Azaserine, Azidocillin, Azlocillin, Aztreonam, Bacitracin, Balofloxacin, Balsalazide, Bambermycins, Beclomethasone Dipropionate, Benazepril, Bendamustine, Bendazac, Benoxaprofen, Benzoylpas, Bepotastine, Bermoprofen, Betamipron, Bevacizumab, Biapenem, Bivalirudin, Bucloxic Acid, Budesonide, Bumadizone, Butibufen, Butyric acid, Cadralazine, Candesartan, Captopril, Carbenicillin, Carbenoxolone, Carbidopa, carbohydrate, Carindacillin, Carmoxirole, Carprofen, Carumonam, Cefaclor, Cefadroxil, Cefamandole, Cefatrizine, Cefazedone, Cefazolin, Cefbuperazone, Cefcapene pivoxil, Cefclidin, Cefdinir, Cefditoren, Cefepime, Cefetamet, Cefinenoxime, Cefinetazole, Cefixime, Cefminox, Cefodizime, Cefonicid, Cefoperazone, Ceforanide, Cefoselis, Cefotaxime, Cefotetan, Cefotiam, Cefoxitin, Cefozopran, Cefpimizole, Cefpiramide, Cefpirome, Cefpodoxime, Cefprozil, Cefroxadine, Cefsulodin, Ceftazidime, Cefteram, Ceftezole, Ceftibuten, Ceftizoxime, Ceftriaxone, Cefuroxime, Cefuzonam, Cephacetrile sodium, Cephalexin, Cephaloglycin, Cephaloridine, Cephalosporin C, Cephalothin, Cephapirin sodium, Cephradine, Certolizumab, Cetirizine, Cetraxate, Cetuximab, Ciclosporine, Cilastatin, Cilazapril, Cinacalcet, Cinchophen, Cinmetacin, Cinoxacin, Ciproflaxacin, Ciprofloxacin, clavulanic acid, Clidanac, Clinafloxacin, Clometacin, Clometocillin, Clonixin, Clopidogrel, Clopirac, Cloxacillin, Colesevelam, Cyclacillin, Dabigatran, Daptomycin, Darbepoetin Alfa, Darunavir, Dasatinib, Decitabine, Delapril, Denosumab, Desvenlafaxine, Dexmethylphenidate, Dextroamphetamine, Diacerein, Diclofenac, Dicloxacillin, Difloxacin, Diflunisal, Dipyrocetyl, DNA, Docetaxel, Dornase Alfa, Duloxetine, Ecabet, Ecteinascidins, Edatrexate, Edeserpidine, Efaproxiral, Eflornithine, Emtricitabine, Enalapril, Enalaprilat, Enfenamic Acid, Enoxacin, Enoxaparin, Enoxolone, Entecavir, Epicillin, Epinephrine, Epoetin Alfa, Eprosartan, Erlotinib, Ertapenem, Etanercept, Ethinyl Estradiol, Etodolac, Etonogestrel, Everolimus, Exenatide, Ezetimibe, Felbinac, Fenbenicillin, Fenbufen, Fenclozic Acid, Fendosal, Fenofibrate, Fenoprofen, Fentiazac, Fexofenadine, Filgrastim, Fingolimod, Fleroxacin, Flomoxef, Floxacillin, Flufenamic Acid, Flumequine, Flunoxaprofen, Flurbiprofen, Fluticasone propionate, foldamers, Folic acid, Formoterol, Foscarnet sodium, Fosfomycin, Fosfosal, Fosinopril, Fropenem, Fusidic acid, Gabapentin, gama-Aminobutyric acid, Garenoxacin, Gatifloxacin, Gemcitabine, Gemifloxacin, Gentisic acid, Glatiramer Acetate, Golimumab, Grepafloxacin, Hetacillin, Human Papilloma Quadrivalent, Hydnocarpic acid, Hydrochlorothiazide, Ibufenac, Ibuprofen, Imidapril, Imipenem, Immune Globulin, Indomethacin, Indoprofen, Infliximab, Insulin Aspart, Insulin Detemir, Insulin Glargine, Insulin Lispro, Interferon beta-1a, Interferon beta-1b, Ipilimubab, Ipratropium, Isofezolac, Isotretinoin, Isoxepac, Ketoprofen, Ketorolac, Lamivudine, L-DOPA, Lenalidomide, Levocabastine, Levodopa, Levonorgestrel, Levothyroxine, Liraglutide, Lisdexamfetamine, Lisinopril, Lomefloxacin, Lonazolac, Loracarbef, Loxoprofen, Lymecycline, Meclofenamic Acid, Mefenamic Acid, Melphalan, Memantine, Merbromin, Meropenem, Mesalamine, Mesalazine, Metampicillin, Metformin, Methicillin, Methotrexate, Methotrexate, Methyl Aminolevulinate, Methyldopa, Methylphenidate, Metiazinic Acid, Metoprolol, Meturedepa, Mezlocillin, microRNA, Miloxacin, Minocycline, Moexipril, Mofezolac, Montelukast, Moveltipril, Moxalactam, Moxifloxacin, mRNA, Nadifloxacin, Nafcillin, Nalidixic acid, Naproxen, Natalizumab, Natamycin, Nateglinide, Nebivolol, Negamycin, Niacin, Niflumic Acid, non-Lipinski molecules, Noprysulfamide, Norethindrone Acetate, Norfloxacin, Norgestimate, Nystatin, Ocreotide Acetate, Ofloxacin, Olanzapine, Olmesartan, Olsalazine, Omalizumab, Omapatrilat, Omega 3-Acid Ethyl Esters, Opiniazide, Oseltamivir, Oseltamivir, Oxaceprol, Oxacillin, Oxaprozin, Oxolinic acid, Oxycodone, Oxymorphone, Paclitaxel, Paliperidone, Paliperidone Palmitate, Palivizumab, p-Aminosalicylic acid, Panipenem, Pazufloxacin, Pefloxacin, Pegfilgrastim, Peginterferon alfa-2a, Pemetrexed, Pemetrexed, Penicillin(s), penicillinic acid sulfone, Penimepicycline, peptide, peptide mimetics, Perindopril, Pexiganan, Phenamet, Phenethicillin, Phthalylsulfacetamide, Phthalylsulfathiazole, Pipemidic acid, Piperacillin, Piperacillin, Pirazolac, Piritramide, Piromidic acid, Pirprofen, PNA, Pralatrexate, Pranoprofen, Prasugrel, Pregabalin, Pregabelin, Propicillin, Propionic acid, protein, Protizinic Acid, Prulifloxacin, Quetiapine, Quinacillin, Quinapril, Ralitrexed, Raloxifene, Raltegravir, Raltitrexed, Ramipril, Ranibizumab, Ranolazine, Rebamipide, Regadenoson, Rescinnamine, Reserpiline, Reserpine, Rifampicin, Rifamycin SV, Rifapentine, Rifaximin, Rifaximin, Risedronic Acid, Ritipenem, Ritonavir, Rituximab, Rosaprostol, Rosoxacin, Rosuvastatin, Rotraxate, Rufloxacin, S-Adenosylmethionine, Salazosulfadimidine, Salbutamol, Salicylamide O-acetic acid, Salicysulfuric acid, Salmeterol, Salsalate, Sampatrilat, Saralasin, Saxagliptin, Sevelamer, Simvastatin, Sitafloxacin, Sitagliptin, small hairpin RNA, small interfering RNA, S-Methylmethionine, Sofalcone, Somatropin, Sparfloxacin, Spirapril, Streptonigrin, Succinylsulfathiazole, Succisulfone, Sulbenicillin, Sulfachrysoidine, Sulfasalazine, Sulindac, Suprofen, Suxibuzone, synthetic oligonucleotides, synthetic peptide, Syrosingopine, Tacrolimus, Tazobactam, Teicoplanin, Telmisartan, Temocapril, Temocillin, Tenofovir Disoproxil, Teriparatide, Testosterone, Tiagabine, Tianeptine, Tiaprofenic Acid, Ticarcillin, Tigemonam, Tinoridine, Tiotropium, Todralazine, Tolfenamic Acid, Tolmetin, Tolterodine, Tosufloxacin, Trandolapril, Trastuzumab, Travoprost, Tropesin. Bermoprofen, Trovafloxacin, Undecylenic acid (10-undecenoic acid), Uredepa ([Bis(1-aziridinyl)phosphinyl]carbamic acid ethyl ester, Ustekinumab, Valganciclovir, Valproic Acid, Valsartan, Vancomycin, Varenicline, Vigabatrin, Vinblastine, Vincristine, Ximoprofen, Zaltoprofen, Zanamivir, Zoledronic Acid, Zolendronic Acid and Zomepirac. Particularly preferably the biologically active molecule is the small molecule drug rifampicin or ciprofloxacin.

In formulae (III) and (IV) each D may be the same or different within the polymer. Preferably, however, it is the same.

Another preferred group of polymers of the present invention comprise a unit of formula (Va) or (Vb):

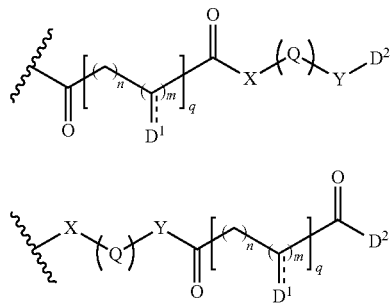

wherein
each n is independently 0 or an integer between 1 and 6;
each m is independently 0 or an integer between 1 and 4, and preferably at least one m is 1;
each $D^1$ is a moiety which is a biologically active molecule, or a derivative thereof, when the C to $D^1$ bond is broken;
$D^2$ is a moiety which is a biologically active molecule, or a derivative thereof, when the Y to $D^2$ bond is broken or a targeting agent;
----- is a bond that may be present or absent;
each q is an integer between 1 and 8;
X is selected from O, S, NH and NR';
Y is selected from O, S, NH and NR';
Q is selected from —$(CH_2)_p$—, —$(CH_2CH_2O)_sCH_2CH_2$—, —$(CH_2)_rNR'$—$(CH_2)_r$— and —$(CH_2CH_2CH_2O)_s$ $CH_2CH_2CH_2$—; each of p, r and s is independently an integer between 1 and 16R' is $C_{1-20}$ hydrocarbyl; and $D^1$ and $D^2$ may be the same or different but are preferably different. Advantageously this enables two different biologically active molecules to be delivered by the same polymer or a biologically active molecule and a targeting agent to be delivered. Suitable targeting agents include biomolecules such as peptides, proteins, peptide mimetics, antibodies, antigens, DNA, mRNA, small interfering RNA, small hairpin RNA, microRNA, PNA, foldamers, carbohydrates, carbohydrate derivatives, non-Lipinski molecules, synthetic peptides and synthetic oligonucleotides.

Preferred values for each of n, m, q, X, Y, R', Q, p and s are as set out above in relation to each of formulae (I), (Ia) and (II). The dashed bond is preferably present. Preferred values for $D^1$ are as set out above for D in relation to formulae (III). Preferred values for $D^2$ are as set out above for D in relation to formulae (IV).

Preferred polymers of the invention comprise a unit of formula (Va-i) or (Vb-i) wherein q is 1:

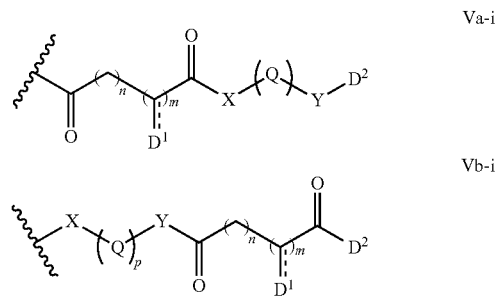

wherein n, m, $D^1$, X, Y, R', Q, p, s and $D^2$ are as defined above in relation to formula (Va) and (Vb).

In preferred polymers of formula (V) $D^1$ and $D^2$ are each formed by the biologically active molecule. Thus $D^1$ and $D^2$ are the moieties derived from the biologically active molecule (s) once it forms a covalent bond to the unit. When the bond between the unit and $D^1$ is broken, i.e the C-$D^1$ bond in formula (V), D becomes the biologically active molecule or an active form, e.g. derivative, of the biologically active molecule. When the bond between the unit and $D^2$ is broken, i.e. the Y-$D^2$ bond in formula (V), D becomes the biologically active molecule or an active form, e.g. derivative, of the biologically active molecule.

In preferred polymers comprising a unit of formula (V), the bond(s) between the unit and each of $D^1$ and $D^2$ is acid-labile. Preferably the bonds are hydrolysed in the acidic and/or hydrolytic environment of cell compartments such as lysosome, endosome, phagosome, phagolysosome and autophagosome found in various cells such as macrophages. Preferably the bond(s) between the unit and each of $D^1$ and $D^2$ is hydrolysed in a pH of <6 and still more preferably in a pH of <5. The hydrolysis of the bond releases the biologically active molecule(s), D.

In preferred polymers comprising a unit of formula (V), the bond(s) between the unit and each of $D^1$ and $D^2$ is direct. More preferably the bond between the unit and $D^1$ is a double bond.

Preferably there are no linking atoms or functional groups between the unit and the drug, $D^1$ or $D^2$. $D^1$ and $D^2$ may be the same or different but are preferably different. As stated above, this enables two different biologically active molecules to be delivered by the same polymer.

Preferably the biologically active molecule $D^1$ comprises a functional group that is able to form a covalent bond with a keto group. More preferably the drug comprises at least one hydrazine group, at least one hydrazide group, at least one amine group, at least one aminooxy group, at least two hydroxyl groups or at least two thiol groups.

In particularly preferred polymers of the invention the biologically active molecule comprises at least one hydrazide group and the bond between the unit and D is a hydrazone. Preferably therefore the polymer comprises a unit of formula (Va-ii) or (Vb-ii):

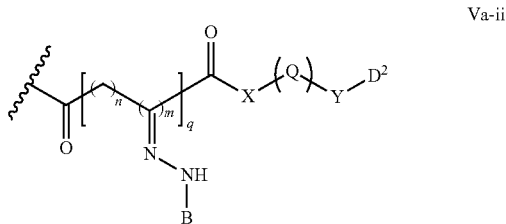

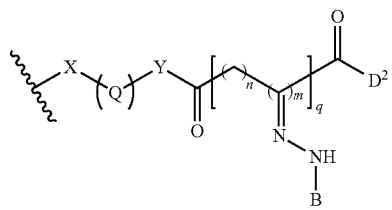
Vb-ii wherein n, m, q, X, Y, R', Q, p, s and D² are as defined above in relation to formula (V) and B is the remainder of D¹, i.e. the remainder of the biologically active molecule that is attached to the hydrazine. Preferred values for each of n, m, q, X, Y, R', Q, p and s are as set out above in relation to each of formulae (I), (Ia) and (II). When the biologically active molecule is released by hydrolysis of the C=N bond in vivo, the biologically active molecule is B—NHNH₂.

In preferred polymers comprising a unit of formula (Va-ii) or (Vb-ii) the drug is selected from the list of drugs set out above in relation to formulae (IIIa). Particularly preferably the biologically active molecule is isoniazid.

In other particularly preferred polymers of the invention the biologically active molecule comprises at least one amine group and the bond between the unit and D is an imine. Preferably therefore the polymer comprises a unit of formula (Va-iii) or (Vb-iii):

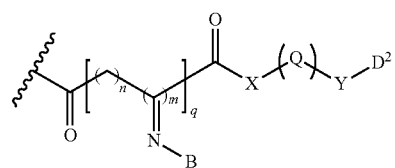
(Va-iii)

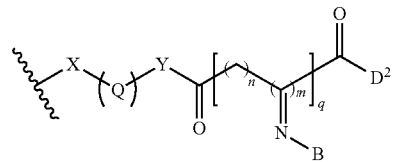
(Vb-iii)

wherein n, m, q, X, Y, R', Q, p, s and D² are as defined above in relation to formula (V) and B is the remainder of D¹, i.e. the remainder of the drug molecule that is attached to the imine. Preferred values for each of n, m, q, X, Y, R', Q, p and s are as set out above in relation to each of formulae (I), (Ia) and (II). When the biologically active molecule is released by hydrolysis of the C=N bond in vivo, the drug is B—NH₂.

In preferred polymers comprising a unit of formula (Va-iii) and (Vb-iii) the biologically active molecule is selected from the list of biologically active molecule set out above in relation to formula (IIIb).

In other particularly preferred polymers of the invention the biologically active molecule comprises at least two hydroxyl groups and the bonds between the unit and D form a ketal. In other particularly preferred polymers there are two biologically active molecules, each comprising a hydroxyl group and the bonds between the unit and D form a ketal. Preferably therefore the polymer comprises a unit of formula (Vaa-iv), (Vab-iv), (Vba-iv) or (Vbb-iv):

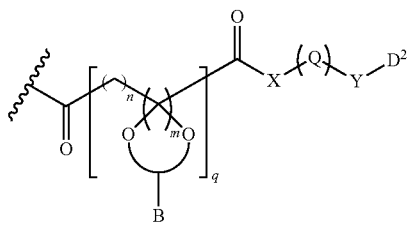
Vaa-iv

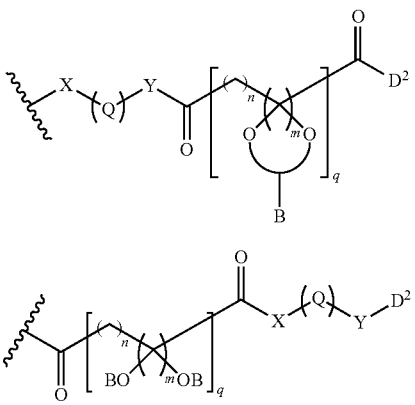
Vab-iv

Vba-iv

Vbb-iv wherein n, m, q, X, Y, R', Q, p, s and D² are as defined above in relation to formula (V) and B is the remainder of D¹, i.e. the remainder of the biologically active molecule that is attached to the diol functional group. Preferred values for each of n, m, q, X, Y, R', Q, p and s are as set out above in relation to each of formulae (I), (Ia) and (II).

In preferred polymers comprising a unit of formulae (Vaa-iv), (Vab-iv), (Vba-iv) or (Vbb-iv) the biologically active molecule is selected from biologically active molecules set out above in relation to formulae (IIIci) and (IIIcii).

In other particularly preferred polymers of the invention the biologically active molecule comprises at least two thiol groups and the bonds between the unit and D form a thioketal. In other particularly preferred polymers there are two biologically active molecules, each comprising a thiol group and the bonds between the unit and D form a thio ketal. Preferably therefore the polymer comprises a unit of formula (Vaa-v), (Vab-v), (Vba-v) or (Vbb-v):

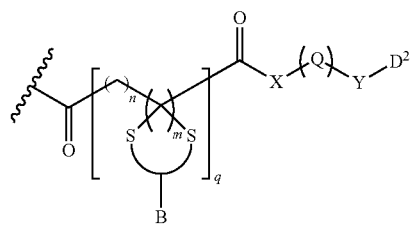
Vaa-v

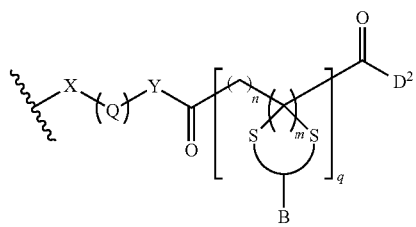
Vab-v

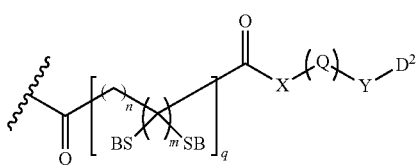
Vba-v

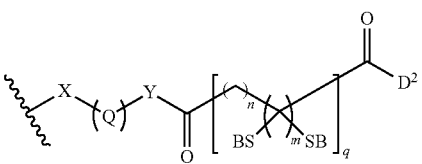
Vbb-v wherein n, m, q, X, Y, R', Q, p, s and $D^2$ are as defined above in relation to formula (III) and B is the remainder of $D^1$, i.e. the remainder of the biologically active molecule that is attached to the dithiol group. Preferred values for each of n, m, q, X, Y, R', Q, p and s are as set out above in relation to each of formulae (I), (Ia) and (II).

In preferred polymers comprising a unit of formula (Vaa-v), (Vab-v), (Vba-v) or (Vbb-v) the biologically active molecule is selected from biologically active molecules as set out above in relation to formulae (IIIdi) and (IIIdii).

In particularly preferred polymers of the invention the biologically active molecule comprises at least one aminooxy group and the bond between the unit and D is an oxime. Preferably therefore the polymer comprises a unit of formula (Ve-i) or (Ve-ii):

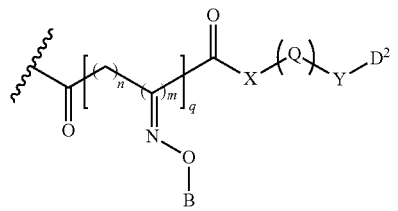
Ve-i

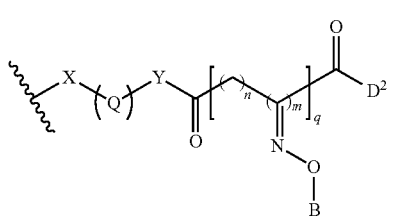
Ve-ii wherein n, m, q, X, Y, R', Q, p, s and $D^2$ are as defined above in relation to formula (V) and B is the remainder of $D^1$, i.e. the remainder of the drug molecule that is attached to the oxime. Preferred values for each of n, m, q, X, Y, R', Q, p and s are as set out above in relation to each of formulae (I), (Ia) and (II). When the drug is released by hydrolysis of the C=N bond in vivo, the drug is B—O—$NH_2$.

In preferred polymers of formulae (V), the biologically active molecule from which $D^2$ derives comprises a functional group that is able to form a covalent bond with the X, Y and/or keto moiety present in the repeat unit. More preferably the biologically active molecule from which $D^2$ derives comprises a functional group selected from carboxylic acid, carboxylic ester, hydroxyl, amine or thiol. Still more preferably the biologically active molecule is selected from the list of biologically active molecules set out above in relation to formula (IV).

The preferred polymers of the present invention may further comprise a repeat unit derived from a biologically active molecule. The advantage of including such a repeat unit is that it enables another different biologically active molecule to be incorporated into the polymer.

Another preferred group of polymers of the present invention comprises a repeat unit of formula (VI):

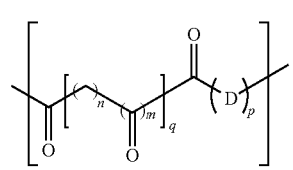
(VI)

wherein
each n is independently 0 or an integer between 1 and 6;
each m is independently 0 or an integer between 1 and 4, and preferably at least one m is 1;
each q is an integer between 1 and 8;
p is an integer between 1 and 16; and
D is a moiety which is a biologically active molecule, or a derivative thereof, when the polymer backbone is degraded.

Preferred polymers of formula (VI) further comprise a repeat unit derived from a compound of formula (II):

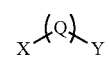

wherein
X is selected from OH, OR', SH, SR', $NH_2$, NHR' and $NR'_2$;
Y is selected from OH, OR', SH, SR', $NH_2$, NHR' and $NR'_2$
Q is selected from —$(CH_2)_p$—, —$(CH_2CH_2O)_s CH_2CH_2$—, —$(CH_2)_r NR'$—$(CH_2)_r$— and —$(CH_2CH_2O)_s CH_2CH_2CH_2CH_2$—;
each of p, r and s is independently an integer between 1 and 16; and
R' is $C_{1-20}$ hydrocarbyl.

Further preferred polymers of formula (VI) comprise a repeat unit of formula (VIa):

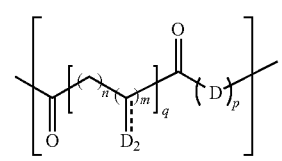
(VIa)

wherein n, m, q, p and D are as defined above in relation to formula (VI) and $D_2$ is as defined for D in relation to formula (III).

Further preferred polymers of formula (VI) and (VIa) may comprise a further biologically active molecule present in a terminal position on the polymer. Preferred polymers of the invention comprise a repeat unit of formula (VI) or (Via) and a unit of formula (IVa) or (IVb).

Preferred values for each of n, m, q, X, Y, R', Q, p and s are as set out above in relation to each of formulae (I), (Ia) and (II). Preferred values for $D^2$ are as set out for D above in relation to formulae (III).

In preferred polymers of formula (VI) and (VIa), D derives from a biologically active molecule which comprises at least two hydroxyl groups, at least two thiol groups, at least two amine groups, at least one hydroxyl group and at least one amine group, at least one hydroxyl group and at least one thiol group or at least one amine group and at least one thiol group. Thus D is the moiety derived from the biologically active molecule once it forms covalent bonds in the backbone of the polymer. When the bonds between adjacent repeat units and D are broken, D becomes the biologically active molecule or an active form, e.g. derivative, of the biologically active molecule.

In preferred polymers comprising a repeat unit of formula (VI) and (VI), the bonds between D and the rest of the polymer are acid-labile. Preferably the bonds are hydrolysed in the acidic and/or hydrolytic environment of cell compartments such as lysosome, endosome, phagosome, phagolysosome and autophagosome found in various cells such as macrophages. Preferably the bond(s) between D and the rest of the polymer are hydrolysed in a pH of <6 and still more preferably in a pH of <5. The hydrolysis of the bond releases the biologically active molecule, D or an active form, e.g. derivative, of the biologically active molecule.

In some preferred polymers comprising a repeat unit of formula (VI) and (VIa), D derives from a biologically active molecule which comprises at least two hydroxyl groups. Preferably D derives from a biologically active molecule which is a diol. Particularly preferably D derives from a biologically active molecule selected from 4-Hexylresorcinol, 5-(methylamino)-2-deoxyuridine (MADU), Alimumab, Amikacin, Amphotericin B, Anidulafungin, Anthramycin, Apicycline, Atorvastatin, Azacitidine, Azidamfenicol, Bambermycins, Beclomethasone Dipropionate, Bimatoprost, Bimatoprost, Bleomycins, Budesonide, Bufeniode, Buprenorphine, Buserelin, Butirosin, Capecitabine, carbohydrates, Carbidopa, Carubicin, Caspofungin, Chloramphenicol, Chlorozotocin, Chlortetracycline, Cladribine, Clindamycin Clomocycline, Colesevelam, Colistin, Cytarabine, Daunorubicin, Decitabine, Demeclocycline, Deoxydihydrostreptomycin, Dexamethasone, Dibekacin, Dihydrostreptomycin, Dilevalol, Dipyridamole, Dirithromycin, DNA, Docetaxel, Doxorubicin, Doxycycline, Ecteinascidins, Enoxaparin, Entecavir, Enviomycin, Epinephrine, Epirubicin, ethambutol, Fenoldopam, Fingolimod, Floctafenine, Fluticasone Propionate, Foscarnet sodium, Gemcitabine, Gentamicin, Glafenine, Glyconiazide, Guamecycline, Idarubicin, Idoxuridine, Indinavir, interfering RNA, Isepamicin, Kanamycin(s), Labetalol, Levodopa, Lincomycin, Lucensomycin, Mannomustine, Meclocycline, Methacycline, Methyldopa, Micafungin, Micronomicin, microRNA, Mikamycin, Minocycline, Mitoxantrone, Mometasone, mRNA, N4-beta-D-Glucosylsulfanilamide, Nadolol, Naloxone, Natamycin, Nebivolol, Nebivolol, Nelfinavir, Neomycin, Netilmicin, Normorphine, Novobiocin, Nystatin, Ocreotide Acetate, oligonucleotide, Oxprenolol, Oxytetracycline, Paromomycin, Penciclovir, Pentostatin, Peplomycin, peptide, Pipacycline, Pirarubicin, Polymyxin, Prednisolone, Primycin, protein, Puromycin, Ramoplanin, Ranimustine, Regadenoson, Ribavirin, Ribostamycin, Rifabutin, Rifalazil, Rifamide, Rifampicin, Rifamycin SV, Rifapentine, Rifaximin, Rifaximin, Ristocetin, Rolitetracycline, Rosuvastatin, S-Adenosylmethionine, Salbutamol, Salmeterol, Azacitidinead, Salsalate Ganciclovir, Sancycline, Sisomicin, small hairpin RNA, Spectinomycin, Streptolydigin, Streptomycin, Streptonicozid, Streptozocin, Sulfinalol, Teicoplanin, Thiamphenicol, Thiostrepton, Tiazofurin, Tobramycin, Travoprost, Trospectomycin, Tuberactinomycin, Tubercidin, Vancomycin, Vidarabine, Viomycin, Zanamivir and Zorubicin.

In some preferred polymers comprising a repeat unit of formula (VI), D derives from a biologically active molecule which comprises at least two amine groups. Preferably D derives from a biologically active molecule comprising from a biologically active molecule which is a diamine. Particularly preferably D derives from a biologically active molecule selected from Abatacept, Adalimumab, Alteplase, Amikacin, antibodies, antigens, Bevacizumab, Bleomycins, carbohydrates, Carboplatin, Certolizumab, Cetuximab, Colesevelam, Colistin, Darbepoetin Alfa, Denosumab, DNA, Dornase Alfa, Efavirenz Insulin Glargine, Epoetin Alfa, Etanercept, Exenatide, Filgrastim, foldamers, Glatiramer Acetate, Golimumab, Human Papilloma Quadrivalent, Immune Globulin, Infliximab, Insulin Aspart, Insulin Detemir, Insulin Lispro, Interferon beta-1a, Interferon beta-1b, Ipilimubab, Lanreotide, Lisdexamfetamine, Metformin, Methotrexate, microRNA, mRNA, Natalizumab, non-Lipinski molecules, Ocreotide Acetate, Omalizumab, Palivizumab, Pegfilgrastim, Peginterferon alfa-2a, peptide mimetics, peptide, PNA, Polymyxin, Pralatrexate, protein, Ranibizumab, Rituximab, Sevelamer, small hairpin RNA, small interfering RNA, Somatropin, synthetic oligonucleotides, synthetic peptide, Teriparatide, Trastuzumab, Ustekinumab and Valganciclovir.

In some preferred polymers comprising a repeat unit of formula (VI), D derives from a biologically active molecule which comprises one hydroxyl group and one amine group. Particularly preferably D derives from a biologically active molecule selected from 2-p-Sulfanilylanilinoethanol, 3-Amino-4-hydroxybutyric Acid, 4-Amino-3-hydroxybutyric Acid, 4-Sulfanilamidosalicylic acid, 5-Hydroxytryptophan, 9-Aminocamptothecin, Abacavir, Acyclovir, Amikacin, Amoxicillin, Amphotericin B, Amprenavir, Arbekacin, Atazanavir, Azacitidine, Bleomycins, Butirosin, Capreomycin, Carubicin, Caspofungin, Cefadroxil, Cefatrizine, Cefoselis, Cefprozil, Cidofovir, Cladribine, Colesevelam, Colistin, Cytarabine, Daunorubicin, Decitabine, Dibekacin, Didanosine, Dideoxyadenosine, Doxorubicin, Doxycycline, Emtricitabine, Entecavir, Enviomycin, Epirubicin, Fingolimod, Forimicins, Formoterol, Gentamicin, Idarubicin, Indinavir, Isepamicin, Kanamycin(s), Lamivudine, Levodopa, Lymecycline, Meclocycline, Mesalamine, Methacycline, Micronomicin, Methyldopa, Metoprolol, Mikamycin, Minocycline, N4-beta-D-Glucosylsulfanilamide, Natamycin, Nebivolol, Negamycin, Neomycin, Netilmicin, Nystatin, Ocreotide Acetate, p-Aminosalicylic acid, Paromomycin, Penciclovir, Peplomycin, Phenyl aminosalicylate, Pirarubicin, Polymyxin, Puromycin, Ramoplanin, Resiquimod, Ribostamycin, Ristocetin, S-Adenosylmethionine, Sampatrilat, Saxagliptin, Sisomicin, Teicoplanin, Tobramycin, Trimazosin, Troxacitabine, Tuberactinomycin, Tubercidin, Tyrocidine, Valganciclovir, Vancomycin, Vidarabine, Viomycin, Zalcitabine and Zorubicin.

Preferred polymers of the present invention further comprise a targeting agent. Preferably the targeting agent is covalently bound to the polymer. Suitable targeting agents include biomolecules such as peptide, protein, peptide mimetics, antibodies, antigens, DNA, mRNA, small interfering RNA, small hairpin RNA, microRNA, PNA, foldamers, carbohydrates, carbohydrate derivatives, non-Lipinski molecules, synthetic peptide and synthetic oligonucleotides.

Preferred polymers of the present invention have a weight average molecular weight of 500 to 500 000 Da, more preferably 1000 to 200 000 Da, still more preferably 1500 to 25 000 Da and yet more preferably about 10 000 Da. Preferred polymers of the present invention have a number average molecular weight of 500 to 500 000 Da, more preferably 1000 to 200 000 Da, still more preferably 1500 to 25 000 Da and yet more preferably 2000 to 20 000 Da. Preferred polymers of the present invention have a polydispersity of 1 to 2.5, more preferably 1.1 to 2.4, still more preferably 1.25 to 2.4 and yet more preferably 1.3 to 2.3.

The biologically active molecule present in the polymers of the present invention preferably has a molecular weight of 32 to 100 000 Da. The biologically active molecule may be a small molecule drug which may be a small organic molecule, i.e. non-polymeric, or polymeric. Preferably the polymer of the present invention comprises 0.5 to 90% wt, more preferably 1 to 70% wt, still more preferably 10 to 60% wt and yet more preferably 15 to 50% wt biologically active molecule, based on the weight of the dry polymer. A key advantage of the polymers of the present invention is that relatively high amounts of biologically active molecule can be incorporated into the polymer. This, in turn, means that high biologically active molecule loadings may be achieved.

The polymer of the present invention may comprise a single biologically active molecule or may comprise a mixture of biologically active molecules. Preferably the polymer comprises a mixture of biologically active molecules. Still more preferably the polymer comprises 2, 3 or 4 different biologically active molecules, e.g. 2 different biologically active molecules.

Preferred biologically active molecules present in the polymers of the present invention are drugs selected from anti-infective, antibiotics, antibacterial, antimicrobial, anti-inflammatory, analgesic, antihypertensive, antifungal, antitubercular, antiviral, anticancer, antiplatelet, antimalarial, anticonvulsant, cardio protective, antihelmintic, antiprotozoal, anti-trypanosomal, antischistosomiasis, antineoplastic, antiglaucoma, tranquilizers, hypnotics, anticonvulsants, antiparkinson, antidepressant, antihistaminic, antidiabetic or antiallurgics. Particularly preferably the drug is an anti-infective and especially antibacterial.

In particularly preferred polymers of the invention, the biologically active molecule is selected from any biologically active molecule listed hereinbefore. Particularly preferably the biologically active molecule is selected from isoniazid, ethambutol, prednisone, ciprofloxacin, memantine, rifampicin and insulin.

The present invention also relates to a method of making a polymer as hereinbefore defined. The method involves reacting a compound of formula (I)

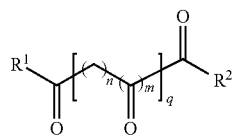

wherein,
$R^1$ and $R^2$ are each independently selected from OH, OR', SH, SR', $NH_2$, NHR' and $NR'_2$;
R' is $C_{1-20}$ hydrocarbyl;
each n is independently 0 or an integer between 1 and 6;
each m is independently 0 or an integer between 1 and 4, and preferably at least one m is 1; and
q is an integer between 1 and 8;
with a biologically active molecule.

A further preferred method of the invention comprises reacting a compound of formula (II):

wherein
X is selected from OH, OR', SH, SR', $NH_2$, NHR' and $NR'_2$;
Y is selected from OH, OR', SH, SR', $NH_2$, NHR' and $NR'_2$
Q is selected from —$(CH_2)_p$—, —$(CH_2CH_2O)_sCH_2CH_2$—, —$(CH_2)_rNR'$—$(CH_2)_r$— and —$(CH_2CH_2O)_s$ $CH_2CH_2CH_2$—; each of p, r and s is independently an integer between 1 and 16; and
R' is $C_{1-20}$ hydrocarbyl;
with said compound of formula (I) and said drug.

In preferred methods of the invention, $R^1$, $R^2$, R', n, m, q, X, Y, Q, p and s are as hereinbefore defined, and preferably as defined in relation to formula (I), (Ia) or (II). In further preferred methods of the invention, the biologically active molecule is as hereinbefore defined or a protected version of a biologically active molecule as hereinbefore defined. Conventional protecting group strategies, as are well known in the art, may be employed during the polymerisation reaction. In preferred methods of the invention the repeat unit formed is as hereinbefore defined and preferably as defined in formula (III), (IV), (V) or (VI).

Preferred methods of the invention are carried out enzymatically or by polycondensation, free radical chain growth polymerisation or ring-opening polymerisation. Preferably the methods of the invention are carried out enzymatically.

The present invention also relates to conjugates of the polymer as hereinbefore defined and a biomolecule and/or targeting agent. Thus the polymer as hereinbefore described may be covalently linked to one or more biomolecules or targeting agents. Suitable biomolecules and targeting agents include peptides, proteins, antibodies, antigens, peptide mimetics, DNA, RNA, oligonucleotides, mRNA, small interfering RNA, small hairpin RNA, microRNA, PNA, foldamers, carbohydrates, carbohydrate derivatives and non-Lipinski compounds.

The present invention also relates to a particle comprising a polymer or mixture of polymers as hereinbefore defined. Preferably the particle is a microparticle or a nanoparticle and more preferably a nanoparticle. Preferably the particle has an average diameter of 1 nm to 10 microns, more preferably 10 to 1000 nm, still more preferably 50 to 800 nm, yet more preferably 20 to 500 nm and yet more preferably 50 to 300 nm. Further preferred particles are solid particles. The average diameter of particles is preferably measured by dynamic light scattering and imaging techniques such as atomic force microscopy, scanning electron microscopy and transmission electron microscopy.

Particularly preferred particles of the present invention further comprise an agent selected from the group consisting of a biologically active molecule, a molecular probe and a diagnostic agent which is non-covalently bound to the polymer. Preferably the agent which is non-covalently bound drug is encapsulated in structures formed by the polymer. The structures may be, for example, micelles, liposomes, polymersomes, nanospheres, microspheres, nanocapsules and microcapsules.

The agent which is non-covalently bound to the polymer may be a biologically active molecule which is the same as one of the covalently bound biologically active molecules or may be different. In still further preferred particles of the present invention the non-covalently bound agent may be a biologically active molecule which is different to the drug(s) covalently bound to the polymer. Preferably the non-covalently bound biologically active molecule is complimentary to the biologically active molecule(s) covalently bound to the polymer. Thus the non-covalently bound biologically active molecule may, for example, have a different mode of action to the covalently bound biologically active molecule(s). Alternatively, or additionally, the non-covalently bound biologically active molecule has an additive, and more preferably, synergistic effect with the covalently bound biologically active molecule(s). This is clearly advantageous for combination therapy. Alternatively, the agent may be a molecular probe or diagnostic agent which, when delivered with the covalently bound biologically active molecule(s) can be used to determine action or effectiveness of said biologically active molecule(s) in the biological system to which it is delivered or to diagnose the nature of a condition in said biological system.

In particularly preferred particles of the present invention, the non-covalently bound agent is selected from any of the biologically active molecule(s) listed hereinbefore, i.e. any of the possible biologically active molecule(s) that may be covalently attached to the polymer, b-lactam, glycopeptides (e.g. vancomycin), macrolides, aminoglycosides (e.g. gentamicin, amikacin), tetracyclines, oxazolidinones, Crestor, Advair Diskus™, Cymbalta, Humira™, Enbrel, Remicade™, Copaxone™ Neulasta™, Singulair™, Rituxan, Atripla, Januvia, Avastin, Lantus, Truvada, Lantus SoloSTAR™, Epogen, Lyrica, Lipitor, Herceptin, Namenda, Avonex, Lucentis, Vyvanse, SEROquel™, Zetia, Methylphenidate ER, Atorvastatin, Symbicort, Atorvastatin, Symbicort, Rebif, NovoLog, SEROquel XR™, Alimta, Levemir, Combivent, ProAir™ HFA, Procrit, Nasonex, Novolog Flexpen, Humalog, Flovent HFA, Neupogen, Neupogen, Vytorin, Budesonide, Janumet, Aranesp, Adderall XR™, Restasis, Gilenya, Prezista, Betaseron, Orencia, Victoza 3-Pak, Synagis, Benicar, Synthroid, Xeloda, Ventolin HFA™, Xolair, Sensipar, Erbitux, Humalog KwikPen™ Stelara, Xgeva™, Sandostatin LAR, Mirena, Focalin XR, Cubicin, Zometa, Pegasys Con. Pack™, Strattera, Revlimid, Asacol, Bystolic, Loestrin 24 Fe™, Yervoy, Lexiscan, Epzicom, Amphetamine Salts, Gamunex-C, NuvaRing™, Norvir, EpiPen 2-Pak, Forteo, Zytiga, Welchol, Metoprolol, Onglyza, Xifaxan, Byetta, Aggrenox, Opana Er, Privigen, Lumigan, Travatan Z, Pulmozyme, Cimzia, Actonel, Prograf™, Ortho Tri Cycl. Lo 28™ NovoLog FlexPen™, Ranexa™, Qvar™, Afinitor, Invega, Tysabri, Sprycel, Valcyte, Exforge, Nutropin AQ, Advair HFA, Chantix, Reclast, Vidaza, Abraxane, Gammagard Liquid, Tamiflu™, Complera, Ciprodex and Activase. Alternatively, the non-covalently bound agent can be a diagnostic agent such as dyes, radiolabelled agents and X-ray contrast agents; or a molecular probe such as a radioactive DNA and RNA sequence probes.

In particularly preferred particles of this aspect of the present invention, the covalently and non-covalently bonded combination of biologically active molecules is used in the treatment of a disease selected from bacterial infection, leprosy, cancer, malaria, Hepatitis C, HIV/AIDS, Cardiovascular disease, Mental disorders, Hormone therapy, Artherosclerosis, Antifungal Agents, Neurodegenerative disease and tuberculosis.

In particularly preferred particles of this aspect of the invention the non-covalently bound biologically active molecule is selected from rifampicin and pyrazinamide and the covalently bound drug is selected from isonaizid, ethambutol and/or rifampicin. This combination is particularly suitable for the treatment of tuberculosis.

Preferably the particles of the invention consist essentially (e.g. consist of) polymer as hereinbefore defined and optionally non-covalently bound biologically active molecule. Preferably at least 90% wt, still more preferably at least 95% wt and still more preferably at least 99% wt of the particles comprise polymer as hereinbefore defined and optionally non-covalently bound polymer.

Particularly preferred particles of the invention further comprise a targeting agent. Preferably the targeting agent is covalently bound to the surface of the particles. Suitable targeting agents include biomolecules such as peptide, protein, peptide mimetics, antibodies, antigens, DNA, mRNA, small interfering RNA, small hairpin RNA, microRNA, PNA, foldamers, carbohydrates, carbohydrate derivatives, non-Lipinski molecules, synthetic peptides and synthetic oligonucleotides.

There are many advantages of forming the polymer comprising biologically active molecule into a particle. The particles may incorporate multiple different biologically active molecule with a high biologically active molecule loading capacity for targeted delivery of the combined biologically active molecule to the site of action (infected tissue, diseased tissue etc). The polymers incorporate the biologically active molecule in the chemical structure of the polymer chain itself, meaning the polymer actually becomes the active ingredient upon degradation. Preferably this is done using only biodegradable constituent materials and biocompatible degradation products.

The formulation of the polymers as particles also produces a more controlled release profile than existing biologically active molecule encapsulation formulations, for which significant burst release effect usually occurs. The particles, formed by the polymer comprising biologically active molecule(s), enable a temporally controlled release of the biologically active molecule. The particles can release biologically active molecules at tunable rates resulting from the gradual degradation of the polymer in response to external stimuli. A slow degradation and high loading allows the sustained release of the biologically active molecules over a long period of time, hence reducing dose frequency. Reducing frequency of dose has the strong potential to improve patient compliance. Additionally the co-delivery of multiple biologically active molecules within the same delivery formulation and their controlled release enables each biologically active molecule to be administered at the correct ratio and promotes synergistic effects which prevent the development of drug resistance.

Another feature of the particles is that they enable an environment specific controlled release of the biologically active molecules in defined conditions found at the site of action. This targeted release inverts the discrepancy between systemic and effective doses, meaning greater efficacy with less of the side-effects resulting from high systemic dosing. Preferably the particles deliver the polymer comprising biologically active molecule in vivo in tact. For example, the particles are of optimum size for cell uptake and as a result they are taken up by, for example, macrophages. This means that the polymer comprising biologically active molecule as hereinbefore defined is not released until the particle is inside a cell where it encounters an acidic and/or hydrolytic environment. In effect therefore the biologically active molecule is delivered to the exact location where it is required.

Optionally the particles of the present invention are coated. The coating may be, for example, a controlled release rate coating. Alternatively, or additionally, the surface of particles, or any coating present therein, may be modified to target a particular area of the body. Targeting agents that may be bound to the coating include, for example, peptides, proteins, antibodies, antigens, peptide mimetics, DNA, RNA, oligonucleotides, mRNA, small interfering RNA, small hairpin RNA, microRNA, PNA, foldamers, carbohydrates, carbohydrate derivatives, and non-Lipinski compounds.

The particles of the present invention are prepared by a method selected from precipitation, e.g. nanoprecipitation, emulsion-diffusion method, double emulsification method, emulsion-coacervation method, polymer-coating method and layer-by-layer method. Preferably the particles of the present invention are prepared by nanoprecipitation.

In a preferred method of nanoprecipitation, a polymer as hereinbefore defined is dissolved in a solvent to form a polymer solution and is added to anti-solvent.

Preferably the solvent is selected from acetonitrile, dimethylsulfoxide, acetone, ethanol, methanol, isopropanol, n-propanol, n-butanol, methyl acetate, ethyl acetate, ethyl formate, dimethyformamide, dichloromethane, chloroform, tetrahydrofuran and N-methyl-2-pyrrolidone. Preferably the concentration of polymer in the solution is 0.00001 to 1 M, more preferably 0.0001 to 0.2 M and still more preferably 0.01 to 0.001 M. Preferably the anti-solvent is selected from water, acetone, ethanol, methanol, isopropanol, n-propanol, n-butanol, methyl acetate, ethyl acetate, ethyl formate and tetrahydrofuran. Preferably the solution of polymer is added dropwise to the anti-solvent. The addition to the anti-solvent causes the polymer to form particles. The particles are preferably isolated by filtration, dialysis, microfluidics, and ultracentrifugation and gel permeation chromatography.

In a particularly preferred method of the present invention, a further biologically active molecule is present during the preparation, e.g. nanoprecipitation, process. Thus preferably a further biologically active molecule is dissolved in the solvent along with the polymer. Preferably the further biologically active molecule is selected from the list of possible non-covalently bound biologically active molecule set out above. Preferably the concentration of further biologically active molecule in the solution is 0.000001 to 1 M, more preferably 0.00001 to 0.1 M and still more preferably 0.01 to 0.0001 M. When nanoprecipitation is carried out with a further biologically active molecule present in the solution, the biologically active molecule present in the solution is preferably encapsulated by structures formed by the polymer.

The present invention also relates to a particle comprising a polymer comprising repeat units of formulae (I) and optionally (II) as hereinbefore defined and an agent selected from the group consisting of a biologically active molecule, a molecular probe and a diagnostic agent, wherein said agent is non-covalently bound to said polymer.

In preferred methods of this aspect of the invention, $R^1$, $R^2$, R', n, m, q, X, Y, Q, p and s are as hereinbefore defined, and preferably as defined in relation to formula (I), (Ia) or (II). In further preferred methods of the invention, the biologically active molecule, the molecular probe and the diagnostic agent are as hereinbefore defined.

Preferably, the non-covalently bound agent is encapsulated in a structure formed by said polymer.

The present invention also relates to a method for making a particle comprising a polymer comprising repeat units of formulae (I) and optionally (II) as hereinbefore defined and an agent selected from the group consisting of a biologically active molecule, a molecular probe and a diagnostic agent, wherein said agent is non-covalently bound to said polymer, wherein said method is selected from precipitation, e.g. nanoprecipitation, emulsion-diffusion method, double emulsification method, emulsion-coacervation method, polymer-coating method and layer-by-layer method. Preferably the particles of the present invention are prepared by nanoprecipitation.

The polymers and particles of the present invention may be incorporated into pharmaceutical compositions. Thus pharmaceutical compositions comprising a polymer and/or a particle as hereinfore defined forms another aspect of the present invention. Pharmaceutical compositions may be prepared in any conventional manner. A pharmaceutical composition may comprise one or more different polymers and/or particles as hereinbefore described. Pharmaceutical compositions may comprise one or more physiologically acceptable carriers or excipients. Suitable carriers and excipients are well known in the art.

Pharmaceutical compositions of the invention may be administered systemically (e.g. orally or parenterally), pulmonary or locally (e.g. by injection). Dosage forms of the present invention therefore include plain or coated tablets, depots, capsules, aerosols, suspensions and solutions, optionally containing pharmaceutical carriers or excipients.

The pharmaceutical compositions and dosage forms may additionally include common pharmaceutical excipients such as lubricating agents, thickening agents, wetting agents, emulsifying agents, suspending agents, preserving agents, fillers, binders, preservatives and adsorption enhancers, e.g. surface penetrating agents. Solubilizing and/or stabilizing agents may also be used, e.g. cyclodextrins (CD). The skilled man will be able to select suitable excipients based on their purpose. Common excipients that may be used in the pharmaceutical products herein described are listed in various handbooks (e.g. D. E. Bugay and W. P. Findlay (Eds) Pharmaceutical excipients (Marcel Dekker, New York, 999), E-M Hoepfner, A. Reng and P. C. Schmidt (Eds) Fiedler Encyclopedia of Excipients for Pharmaceuticals, Cosmetics and Related Areas (Edition Cantor, Munich, 2002) and H. P. Fielder (Ed) Lexikon der Hilfsstoffe fur Pharmazie, Kosmetik und angrenzende Gebiete (Edition Cantor Aulendorf, 1989)).

The pharmaceutical compositions and dosage forms of the invention may be formulated so as to provide quick, sustained or delayed release of the polymer and/or particles after administration to the patient by employing procedures well known in the art. The concentration of the polymers and particles herein described in the pharmaceutical compositions depends upon numerous factors including the nature of the polymer, the drug loading on the polymer, the composition, the mode of administration, the condition to be treated or diagnosed, and the subject to which it is administered and may be varied or adjusted according to choice.

The polymers, particles and pharmaceutical compositions hereinbefore described are for use in medicine. Preferably the polymers, particles and pharmaceutical compositions hereinbefore described are for use in the treatment of a disease selected from inflammatory diseases (e.g. inflammatory bowel disease, rheumatoid arthritis and artherosclerosis), metabolic disorders (e.g. diabetes, insulin resistance, obesity), cancer, bacterial infections (e.g. Tuberculosis, pneumonia, endocarditis, septicaemia, salmonellosis, typhoid fever, cystic fibrosis, chronic obstructive pulmonary diseases), viral infections, cardiovascular diseases, neurodegenerative diseases, neurological disorders, behavioral and mental disorders, blood diseases, chromosome disorders, congenital and genetic diseases, connective tissue diseases, digestive diseases, ear, nose, and throat diseases, endocrine diseases, environmental diseases, eye diseases, female reproductive diseases, fungal infections, heart diseases, hereditary cancer syndromes, immune system diseases, kidney and urinary diseases, lung diseases, male reproductive diseases, mouth diseases, musculoskeletal diseases, myelodysplastic syndromes, nervous system diseases, newborn screening, nutritional diseases, parasitic diseases, rare Cancers, and skin diseases. Particularly preferably the disease is a bacterial infections and especially tuberculosis.

The present invention also provides a polymer as hereinbefore described or a particle as hereinbefore described, wherein release of said biologically active molecule from said polymer is pH sensitive and is dependent upon the nature of the bond between said biologically active molecule and the repeat unit of the polymer to which it is covalently bound.

BRIEF DESCRIPTION OF FIGURES

These and other aspects of the invention will now be further described, by way of example only, with reference to the accompanying figures in which.

EXAMPLES

Materials

Figure 1:
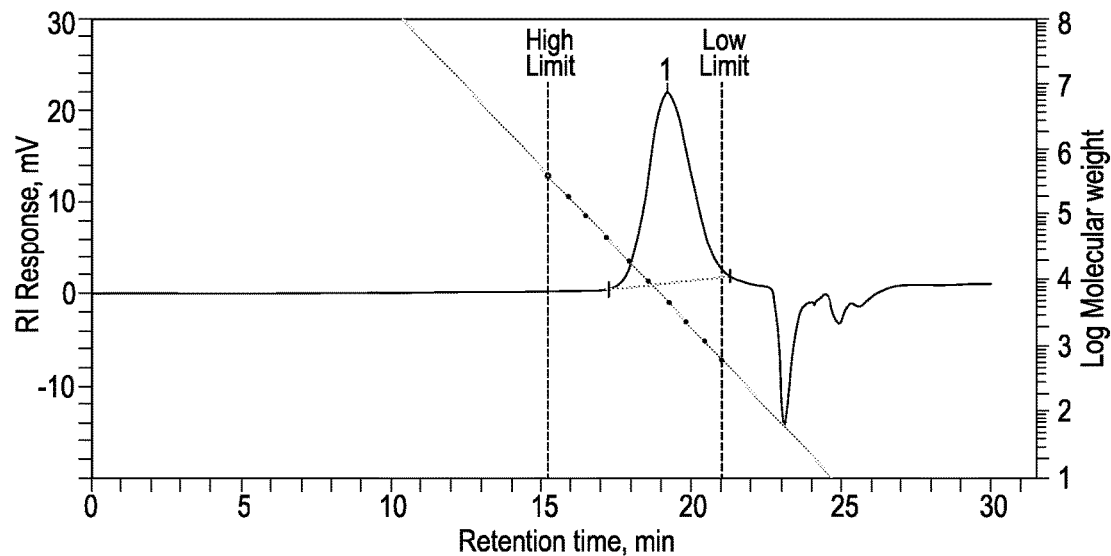
FIG. 1 is a graph showing Gel Permeation Chromatography (GPC) analysis of blank polymer E55 after a 22 h polymerization time.

All starting materials employed are commercially available. 1,8-octanediol, dimethyl-2-oxoglutarate, dimethyl-3-oxoglutarate, triethylene glycol, N-methyldiethanolamine, N,N,N',N'-tetramethyl-O-(1H-benzotriazol-1-yl)uronium hexafluorophosphate (HBTU), Novozym™ 435, isoniazid (INH), rifampicin (RIF), ciprofloxacin, memantine, prednisone, insulin, ethambutol (EMB) were obtained from Sigma Aldrich.

Other commercially available chemicals were also employed. Chloroform, diphenyl ether, hexane, diisopropylethylamine (DIPEA), dichloromethane (DCM), magnesium sulfate, sodium hydroxide, toluene, o-benzylhydroxylamine, acetonitrile (MeCN), High Performance Liquid Chromatography (HPLC) water, Nile Red™ fluorescent dye, dimethyl sulfoxide (DMSO), p-tolunesulfonic acid (PTSA), ethanol, mica substrate, phosphate buffer, citrate buffer, acetate buffer, trifluoroacetic acid (TFA), diethyl ether, sodium-1-heptanesulfonate, modified Eagle's Minimum Essential Media (Opti-MEM) cell culture medium, Dulbecco's Modified Eagle Medium (DMEM), Fetal Calf Serum (FCS), penicillin (PEN), fluorescein isothiocyanate (FITC), propidium iodide (PI) were obtained from Sigma Aldrich, Fisher scientific, Life technologies, Lonza and Agar Scientific.

Analysis Methods

Gel Permeation Chromatography (GPC) analysis was performed to determine polymer molecular weight, polydispersity and degree of polymerization using a GPC system PL-GPC-50 (Polymer laboratories, Agilent Technology). Analytical grade chloroform was used as eluent at a flow rate of 0.3 mL min$^{-1}$. The run time for one analysis was 30 min. The injection loop was purged with 3 mL chloroform prior to each injection. A 10 point mass calibration was done with polystyrene standards (EasyCal PS-2, Polymer Laboratories, Agilent). Samples of the bulk phase of polymerization were diluted in 1 mL chloroform and directly injected into the GPC.

Further characterization of polymers was performed using Nuclear Magnetic Resonance (NMR) on 400 and 500 MHz NMR spectrometers. Note that complete assignment of peaks in $^1$H NMR spectra requires further NMR analysis.

Dynamic Light Scattering (DLS) analysis was performed using a Zetasizer Nano series (Malvern Instruments, UK). DLS size and zeta potential analysis was performed at 25° C. at 173° backscatter angle in low volume sizing cuvettes (1.5 mL semi-micro, PMMA; Brand, UK) or in DTS1060c clear disposable zeta cells (Malvern, UK). Water or PBS was set as dispersants for all measurements, and PLGA was used as a model for the unknown RI of the sample. One analysis comprised 10 measurements consisting of 10 sub-runs per measurement with 10 s analysis per run. For the determination of zeta potential, 10 measurements with 20 sub-runs were used. Results were calculated internally from Smoluchowski's model.

Atomic Force Microscopy (AFM) was performed using a PicoPlus AFM™ with a PicoSPM II controller from Molecular Imaging, Agilent. A drop of nanoparticle suspension was deposited on a cover slip with a mica surface. After drying, the samples were analyzed in intermittent Contact Mode AFM.

Fluorescent Imaging was performed using a Zeiss LSM 780 Confocal Laser Scanning Microscope.

High Performance Liquid Chromatography (HPLC) was performed using a HPLC system (Waters) consisting of a 1525 Binary HPLC Pump, a 2487 Dual A Absorbance Detector, and an Ascentis® Express Peptide ES-C18 column with a length of 50 mm. The eluent was 99.9% water and 0.1% Trifluoroacetic acid for INH quantification. A nine-point standard curve was made by serial dilution of INH in water, various buffers and 0.5 M NaOH (linear regression y=36.005 x+0.1685, $R^2$=99.4%.) A gradient of eluent A (99.9% water and 0.1% Trifluoroacetic acid) and eluent B (90% acetonitrile, 9.9% water and 0.1% and Trifluoroacetic acid) was used for the analysis of insulin, blank polymer 1 and insulin-containing polymer.

Ion-Pair High Performance Liquid Chromatography (HPLC) was performed using a HPLC system (Waters) consisting of a 1525 Binary HPLC Pump, a 2487 Dual A Absorbance Detector, and an Ascentis® Express Peptide ES-C18 column with a length of 50 mm. HPLC analysis was performed with a mobile phase containing cupric ions, which are known to form UV-absorbing complexes with EMB. The mobile phase consisted of 4 g Sodium-1-heptanesulfonate and 0.16 g copper sulfate dissolved in 750 mL deionized (DI) water and 250 mL Tetrahydrofuran. The apparent pH was adjusted to pH 4.5 with 1 M NaOH before each analysis. A seven-point standard curve was made by preparing solutions of EMB in the mobile phase (linear regression: y=57.93 x–0.036, $R^2$=99.9%.)

Ultraviolet (UV) Spectrometry was performed using a UV-Vis spectrometer (Varian Cary® 300 UV-Vis Spectrometer, Agilent Technologies, UK). An UV spectrum of a 25 µg mL$^{-1}$ RIF solution in acetonitrile was recorded, and the absorption of five standard concentrations of RIF were measured at the wavelength of 475 nm. A linear correlation function of RIF concentration and absorbance was derived.

Flow cytometry was performed using conventional apparatus.

Bioassay against *Mycobacterium bovis* BCG-lux (Bacille Calmette Guerin) grown in human monocyte-derived macrophages was performed as follows: Macrophage cell culture: Human peripheral blood monocyte-derived macrophages. Venal blood from healthy blood donors mixed 10:1 (v:v) with PBS containing 4% citrate. 15 mL Lympholyte-Human (Cedarlane, Canada) peripheral blood mononuclear cell (PBMC) separation medium was filled into 50 mL Falcon tubes. The fluid was overlayered without mixing with 25 mL blood/citrate per tube. The blood was fractionated by centrifugation for 22 min at 1900 rpm without braking in a Beckman & Coulter Alegra X-15R centrifuge. PBMCs accumulated in the layer between blood serum (top) and Lympholyte medium (bottom), with red blood cells and thrombocytes in the pellet. The PBMC layers of all Falcon tubes were pipetted to a fresh Falcon tube. Cells were washed twice by suspending in 50 mL Roswell Park Memorial Institute Medium 1640 (RPMI 1640) and pelleting at 1450 rpm for 10 min.

A 5 µL aliquot of the cell pellet was mixed with 5 µL Trypan Blue, and the cell concentration was measured in a Countess™ Automated Cell Counter (Life Technologies, California, USA).

CD14$^+$ cells were selected and concentrated by a magnetic assisted cell sorting (MACS®) technique. The pellet was resuspended in 80 µL PBS 0.4% citrate per 10$^7$ cells. 20

μL ferromagnetic MACS MicroBeads covered with CD14 specific monoclonal antibodies were added per $10^7$ cells. The mixture was incubated at 4° C. for 30 min to allow antibody-antigen binding. The resulting PBMC-bead adducts were washed in 50 mL PBS 4% citrate and collected by centrifugation at 1300 rpm for 10 min. The pellet was resuspended in 0.5 mL PBS 0.4% citrate per $10^8$ cells. LS columns with 8 mL reservoir volume (Miltenyi Biotech) were mounted in a MidiMACS™ separator and rinsed with 3 mL PBS 0.4% citrate. 500 μL PBMC-bead adduct suspension was pipetted to each column. Unbound cells were washed away by thrice rinsing with 3 mL PBS 0.4% citrate. The column was then removed from the magnetic source, and bound cells were eluated by two-fold rinsing with 5 mL PBS 0.4% citrate. Elution was supported by firm application of a plunger that was supplied with the columns. CD14+ cells were concentrated by centrifugation at 1300 rpm for 10 min. The pellet was resuspended in Dublecco's Modified Eagle Medium (DMEM medium, Lonza, Switzerland) containing 20 vol.-% fetal calf serum (FCS). The cell concentration of an aliquot was determined as described above, and the cell suspension was diluted to a concentration of $10^6$ cells $mL^{-1}$ with DMEM FCS.

200 μg macrophage colony stimulating factor (PeproTech Inc., New Jersey, USA, in aqueous 100 μg $mL^{-1}$ stock) was added per mL cell culture. $2*10^5$ cells were seeded in 24 well culture plates (Greiner BioOne, Austria) and incubated for 5 days at 37° C. in a 5% $CO_2$ incubator for differentiation to macrophages.

BCG-lux cell culture: A cryo conservation vial with BCG lux cells in glycerol was defrosted at room temperature. The inoculum was poured into a 250 mL single-use Erlenmeyer flask equipped with 100 mL growth medium, and incubated at 37° C. and 220 rpm for 48 h. The growth medium contained 4.7 g $L^{-1}$ 7H9 broth (Middlebrook, UK), 10 vol. % ADC supplement (Becton Dickinson and Co.), 50 mg $L^{-1}$ Hygromycin B (Roche, UK), 2 vol. % glycerol and 2 vol. % Tween 80 in ultrapure water.

BCG lux cells were harvested by centrifugation at 2000 rpm for 10 min. The pellet was redispersed in 20 mL DMEM medium with 10% FCS and 60 mg $mL^{-1}$ penicillin (Roche, UK) (DMEM FCS PEN medium). The concentration of luminescent cells was measured in triplicate in a Glomax™ 96 microplate luminometer (Promega, UK). 200 μL cell suspension were pipetted into 3 wells of an opaque 96 well luminometer plate (Greiner BioOne, Austria). The luminometer measured the relative light units (RLU) emitted from luminescent bacteria upon automated injection of 25 μL 1% aqueous decanol solution to each vial. The method was calibrated for the equivalence of 1 RLU per 1 BCG-lux bacteria.

For infection of human macrophages, the BCG-lux concentration was diluted to 250000 RLU $mL^{-1}$.

Macrophage infection: The growth medium was pipetted from the confluent macrophage culture, and non-adherent cells were removed by two-fold washing with 0.5 mL sterile PBS. Macrophages were incubated with 200 μL BCG lux dispersion per well (50000 bacteria) for 1 h at 37° C. and 5% $CO_2$. The fluid was removed, and the cells were washed twice with sterile PBS. To eliminate extracellular BCG lux, the cells were incubated for 10 min with DMEM FCS PEN medium containing 60 mg $mL^{-1}$ streptomycin. The streptomycin medium was removed, and the cells were washed twice with sterile PBS.

Determination of nanoparticle efficacy: The infected cells were incubated for 1, 3 or 5 days with 200 or 300 μL of nanoparticle dispersion in DMEM FCS PEN medium. As a positive control, pure drug was used. The free drug concentration was equivalent to the quantified drug release from nanoparticles. In some experiments, free drugs were additionally tested at the minimum inhibitory concentrations (MIC) given in literature. Pure medium was used as a negative control. All conditions were applied in 6 wells.

After incubation, the medium was removed, and the cells were washed twice with sterile PBS. The macrophages were lysed in 250 μL sterile distilled water for 10 min. During the lysis time, the wells were scraped with a sterile cell scraper. A new cell scraper was used for every condition. 200 μL cell lysate was transferred to a luminometer plate, and the luminescence RLU was measured as described above.

Significant reduction of BCG-lux RLU in comparison to untreated cells was tested with unpaired Student t-test at independent variance ($\alpha=0.05$, $n=6$).

Preparative Example for the Synthesis of a Blank Polymer 1

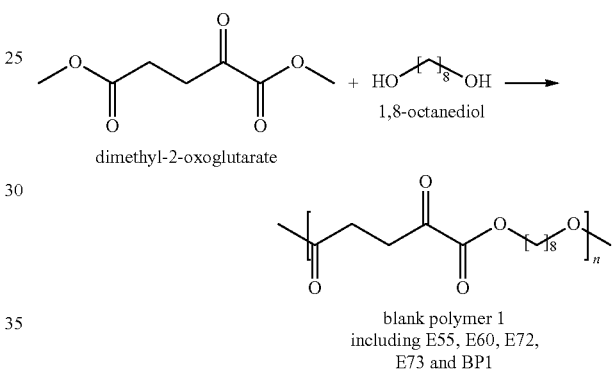

dimethyl-2-oxoglutarate 1,8-octanediol blank polymer 1 including E55, E60, E72, E73 and BP1

Blank polymers 1 including E55, E60, E72, E73 were synthesized as following. 1,8-Octanediol and dimethyl-2-oxo-glutarate were combined in a round-bottomed flask, which was heated to 75° C. on a hot plate equipped with an oil bath. *Candida Antarctica* Lipase B (CALB) as immobilized enzyme (Novozym™ 435, N435. N435 contains 10% w/w CALB and 90% w/w acrylic resin) beads were added and the bulk was stirred magnetically at 200 rpm for 1.5 h. A chemo-resistant diaphragm vacuum pump then was connected to the reaction vessel and run continuously. Diphenyl ether (1 mL) was then added to reduce viscosity and the temperature was increased to 90° C. Gel Permeation Chromatography (GPC) analysis of molecular weight was performed until sufficient size and monodispersity was achieved.

The GPC analysis for blank polymer 1 E55 after a 22 h polymerization time is shown in FIG. 1. The product was purified by two-fold precipitation in hexane. The dashed lines indicate the high and low limits of molecular weight calibration. The square data points represent calibration data.

The reaction was quenched by addition of chloroform (3 mL). The enzyme beads were filtered off and the reaction vessel and filtering unit were washed with additional chloroform (3 mL). The filtrates were precipitated with hexane (50 mL) and washed by centrifugation. The pellets were dried under nitrogen for 15 min and left in a vacuum desiccator overnight. Table 1 indicates the polymer size and dispersity for each of the blank polymers synthesised. The yield of polymerization $Y_P$ was estimated from the dry mass of polymer and the theoretic mass of an ideal (monodisperse) polymer.

Figure 2:
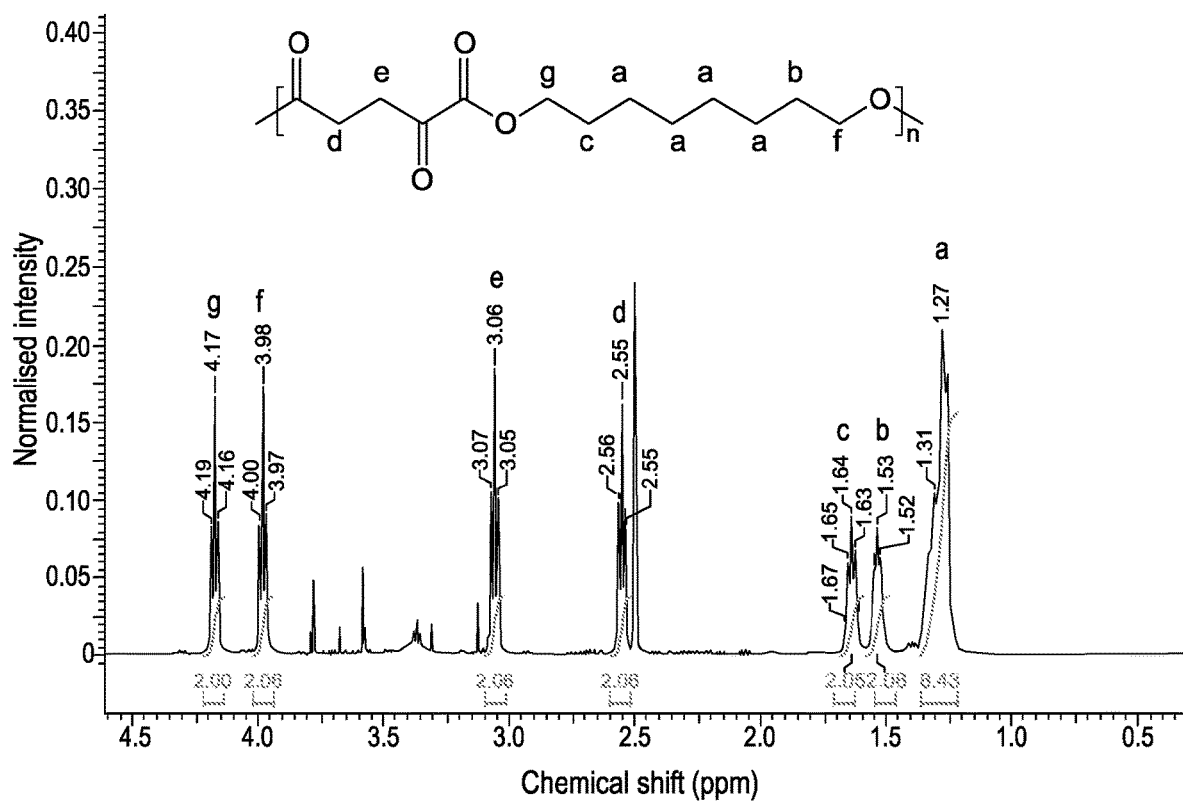
FIG. 2 is a $^1$H-NMR spectrum of blank polymer 1 in DMSO-d6.

The $^1$H-NMR spectrum of blank polymer 1 in DMSO-d6 is shown in FIG. 2.

Polymer Size and Dispersity

TABLE 1

| Blank polymer 1 | time, h | $M_p$, Da | $M_n$, Da | PD | $Y_p$, % | $P_n$ |
|---|---|---|---|---|---|---|
| E55 | 22 | 5973 | 4014 | 1.68 | 64 | 15.6 |
| E60 | 24 | 3302 | 2567 | 1.55 | 58 | 9.9 |
| E72 | 24 | 26654 | 16462 | 2.23 | 89 | 64.2 |
| E73 | 6 | 10675 | 7654 | 2.10 | 80 | 29.8 |

[$M_p$: molecular weight at peak maximum; $M_n$: number-mean molecular weight; PD: polydispersity; $Y_p$: yield of polymerisation; $P_n$: number-mean degree of polymerization].

Preparative Example for the Preparation of Nanoparticles of a Blank Polymer 1

The nanoparticles were prepared by nanoprecipitation. The polymer was dissolved in acetonitrile (20 mg/mL) at room temperature. The polymer solution was slowly dropped into a 20-fold volume of HPLC grade water, which was being stirred continuously. The nanoparticles were washed with HPLC grade water and collected by centrifugation. The resulting pellets were dispersed in water and stored at 4° C.

The particle size and zeta potential of the polymer nanoparticles were measured by DLS as shown in Table 2. A first aliquot of the final dispersion was diluted to 1:20 in 10 mM citrate buffer at pH 5 to mimic phagolysosomal pH. A second aliquot was diluted to 1:20 in 10 mM phosphate buffer at pH 7.4 to simulate physiological extracellular pH conditions.

DLS Characterization of Polymeric Nanoparticles

TABLE 2

| Blank polymer 1 | Z-average ± PDI width d, nm | $d_{Number}$, nm | PDI | zeta potential, mV |
|---|---|---|---|---|
| E55 BLANK | | | | |
| pH 5 | 169 ± 36 | 145 ± 4 | 0.05 ± 0.02 | −54 ± 4 |
| pH 7.4 | 169 ± 52 | 137 ± 4 | 0.10 ± 0.02 | −66 ± 3 |
| E60 BLANK | | | | |
| pH 5 | 175 ± 65 | 135 ± 5 | 0.14 ± 0.03 | −70 ± 6 |
| pH 7.4 | 176 ± 66 | 135 ± 9 | 0.14 ± 0.03 | −65 ± 4 |
| E72 BLANK | | | | |
| pH 5 | 150 ± 45 | 118 ± 6 | 0.09 ± 0.03 | −40 ± 3 |
| pH 7.4 | 146 ± 29 | 123 ± 3 | 0.04 ± 0.02 | −71 ± 2 |

Z-average: cumulants mean; $d_{Number}$: number-mean size; values ± standard deviation of DLS measurement runs; PDI: polydispersity index.

Figure 3:
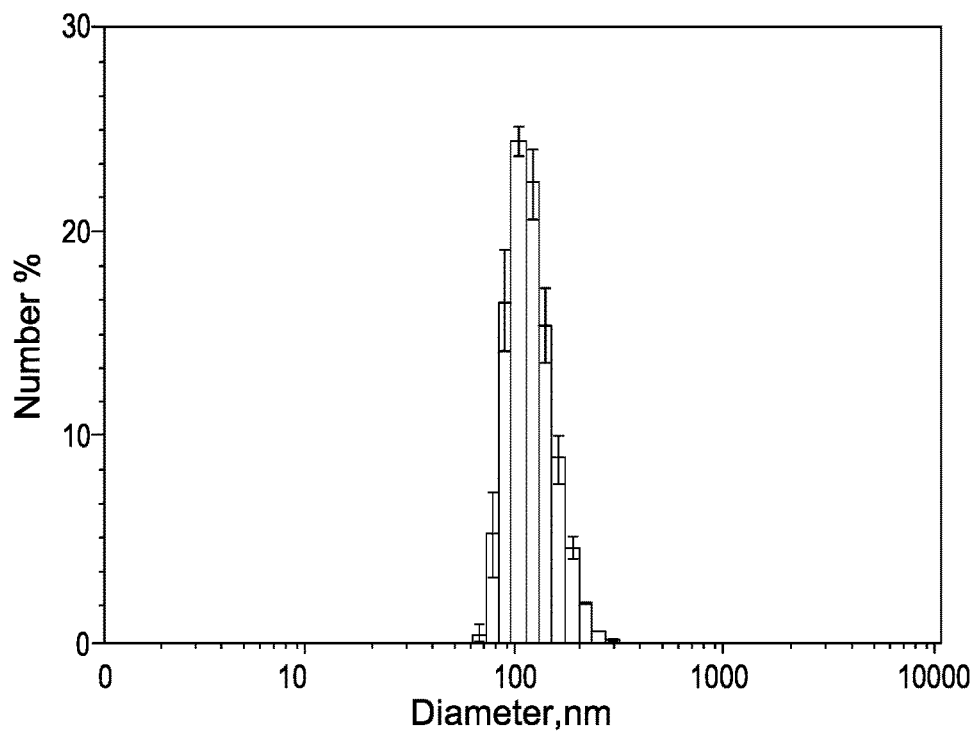
FIG. 3 is a bar graph showing the number-mean size distribution of E60 nanoparticles at pH 7.4.

FIG. 3 shows a number-mean size distribution of E60 nanoparticles at pH 7.4. DLS was used to measure the size of the nanoparticles at scattering angle of 173° in 10 mM phosphate buffer pH 7.4. 10 measurements were performed, each having 10 sub-runs. The error bars represent ±standard deviation of the runs.

Figure 4:
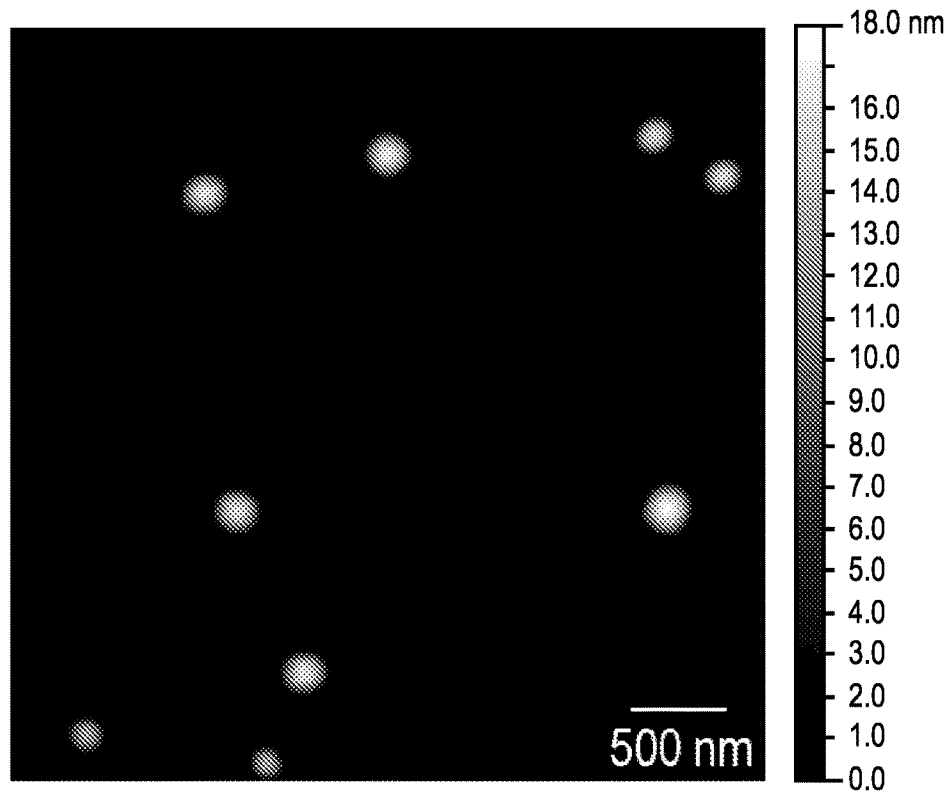
FIG. 4 is an Atomic Force Microscopy (AFM) image of E60 nanoparticles.

Nanoparticle morphology was determined by AFM. FIG. 4 shows nanoparticles of E60 with heights of ~15 nm and widths of ~300 nm. Deformation of the nanoparticles on the mica substrate was observed, which was attributed to the drying of the nanoparticles for imaging.

To assess the uptake of nanoparticles by macrophages, the fluorescent dye Nile Red™ was encapsulated in nanoparticles of blank polymer E60. Encapsulation was achieved by nanoprecipitation as previously described with 0.05 mg mL$^{-1}$ Nile Red™ in the acetonitrile phase.

Figure 5:
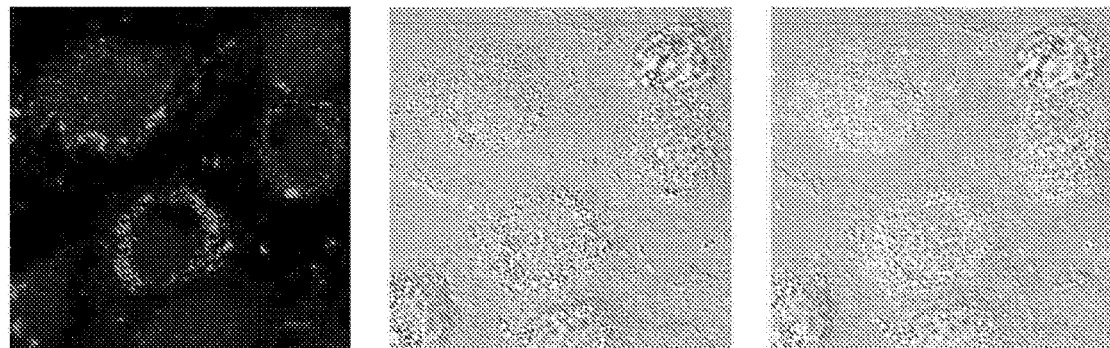
FIG. 5 is a fluorescent image of human monocyte-derived macrophages incubated for 1 h with a 0.5 mg mL$^{-1}$ E60 nanoparticle suspension (encapsulating the dye Nile Red™) in Opti-MEM cell culture medium. The left-hand image shows fluorescence at 50% cell height; the central image shows a light microscopy image; and the right-hand image shows an overlay of the two images. Bars: 10 µm.

FIG. 5 shows human monocyte-derived macrophages incubated for 1 h with a 0.5 mg mL$^{-1}$ nanoparticle suspension in Opti-MEM cell culture medium. Nanoparticles encapsulated the dye Nile Red™ for fluorescent staining. The left-hand image of FIG. 5 shows fluorescence at 50% cell height; the central image shows a light microscopy image; and the right-hand image shows an overlay of the two images.

Preparative Example for the Synthesis of a Blank Polymer 2 Made from Dimethyl-3-Oxoglutarate and 1,8-Octanediol

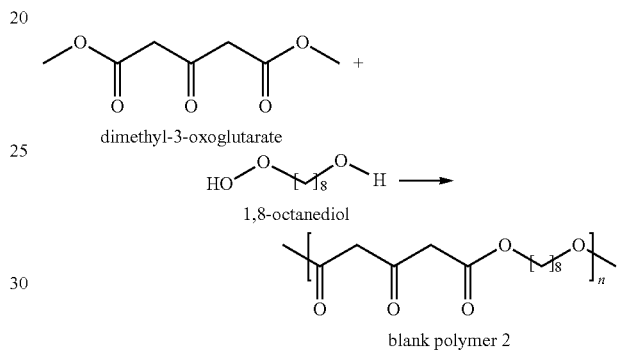

blank polymer 2

Blank polymer 2 was prepared by reacting dimethyl-3-oxoglutarate and 1,8-octanediol using the same polymerisation process as that described for the preparation of blank polymer 1 above.

Figure 6:
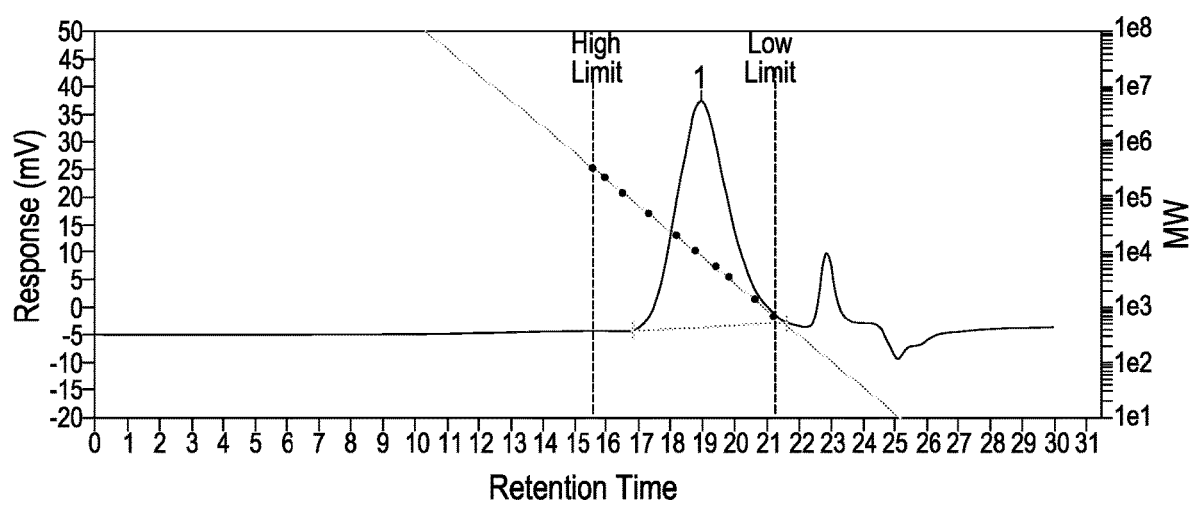
FIG. 6 is a graph showing Gel Permeation Chromatography (GPC) analysis of blank polymer 2 after a 2 h polymerization time.
Figure 7:
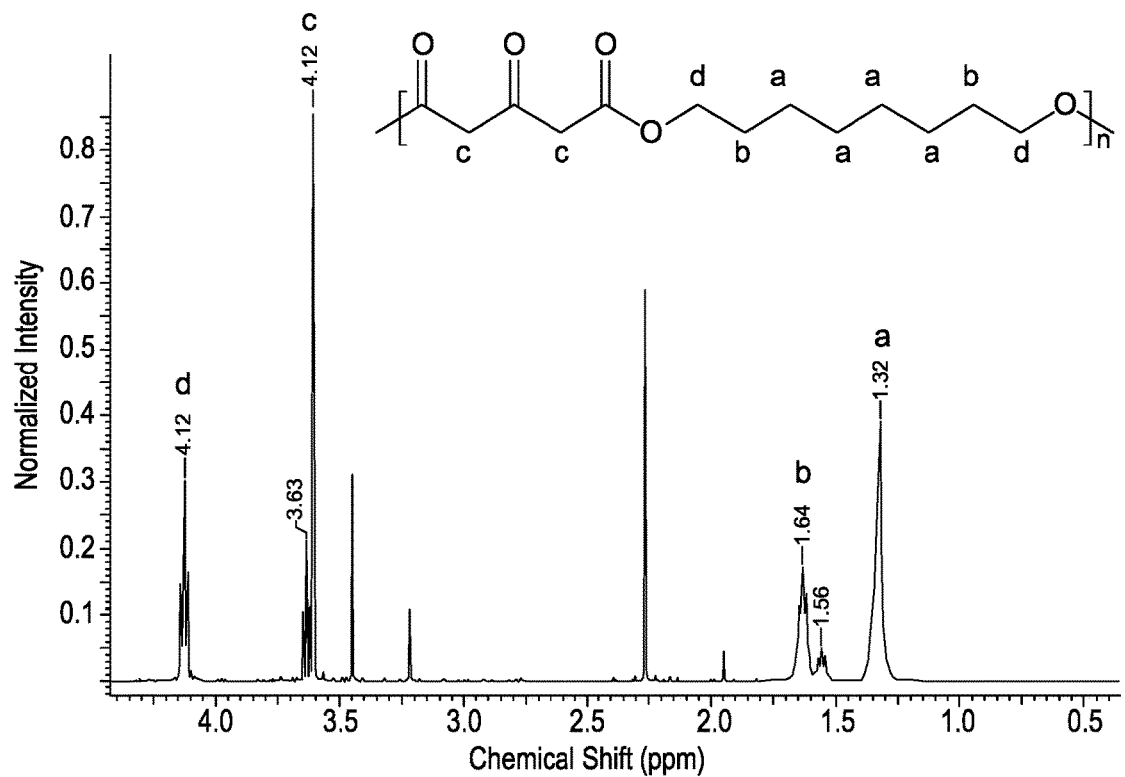
FIG. 7 is a $^1$H-NMR spectrum of blank polymer 2 in CDCl$_3$.

The GPC analysis for blank polymer 2 after a 2 h polymerization time is shown in FIG. 6. The dashed lines indicate the high and low limits of molecular weight calibration. The square data points represent calibration data. Table 3 indicates the polymer size and dispersity for the blank polymer 2 synthesised by reaction of dimethyl-3-oxoglutarate and 1,8-octanediol. The $^1$H-NMR spectrum of blank polymer 2 in CDCl$_3$ is shown in FIG. 7.

Polymer Size and Dispersity of Blank Polymer 2

TABLE 3

| time, h | $M_p$, Da | $M_n$, Da | PD | $Y_p$, % | $P_n$ |
|---|---|---|---|---|---|
| 2 | 8585 | 5234 | 2.02 | 65 | 20 |

[$M_p$: molecular weight at peak maximum; $M_n$: number-mean molecular weight; PD: polydispersity; $Y_p$: yield of polymerisation; $P_n$: number-mean degree of polymerization].

Preparative Example for the Preparation of Nanoparticles of a Blank Polymer 2 Prepared from Dimethyl-3-Oxoglutarate and 1,8-Octanediol Nanoparticles were prepared from blank polymer 2 prepared above in the same manner as the nanoparticles prepared from blank polymer 1 above.

The particle size and zeta potential of the polymer nanoparticles were measured by DLS as shown in Table 4. A first aliquot of the final dispersion was diluted in water. A second aliquot was centrifugated and resuspended in 10 mM citrate buffer at pH 5 to mimic phagolysosomal pH. A third aliquot was centrifugated and resuspended in 10 mM phosphate buffer at pH 7.4 to simulate physiological extracellular pH conditions.

DLS Characterization of Polymeric Nanoparticles

TABLE 4

| Blank polymer 2 | Z-average ± PDI width d, nm | $d_{Number}$, nm | PDI | zeta potential ± zeta deviation, mV |
|---|---|---|---|---|
| water | 236 ± 118 | 180 | 0.248 | −32 ± 10 |
| pH 5 | 281 ± 142 | 187 | 0.252 | −18 ± 28 |
| pH 7.4 | 287 ± 20 | 194 | 0.174 | −25 ± 56 |

Z-average: cumulants mean; $d_{Number}$: number-mean size; PDI: polydispersity index.

Preparative Example for the Synthesis of a Blank Polymer 3 Made from Dimethyl-2-Oxoglutarate and Triethylene Glycol

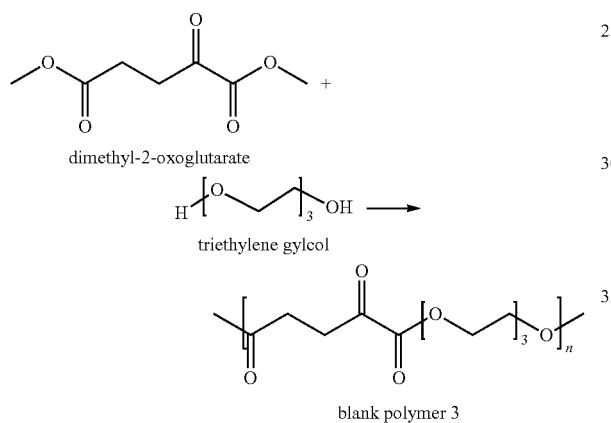

Blank polymer 3 was prepared by reacting dimethyl-2-oxoglutarate and triethylene glycol using the same polymerisation process as that described for the preparation of blank polymer 1 above.

Figure 8:
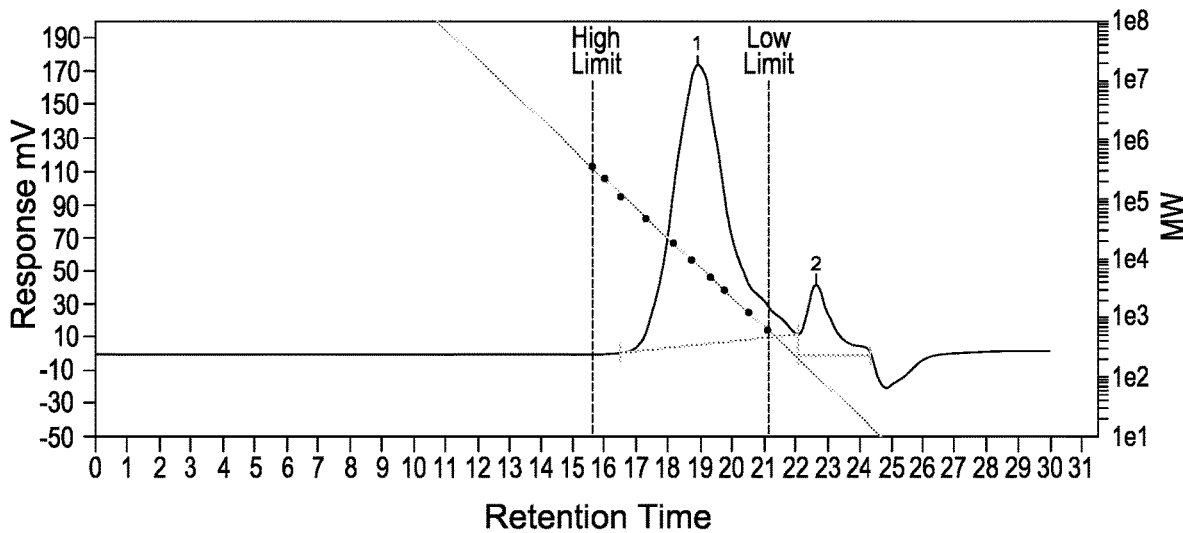
FIG. 8 is a graph showing Gel Permeation Chromatography (GPC) analysis of blank polymer 3 after a 36 h polymerization time.

The GPC analysis for blank polymer 3 prepared from reaction of dimethyl-2-oxoglutarate and triethylene glycol after a 36 h polymerization time is shown in FIG. 8. The dashed lines indicate the high and low limits of molecular weight calibration. The square data points represent calibration data.

Table 5 indicates the polymer size and dispersity for the blank polymer 3 synthesised.

Polymer Size and Dispersity of Blank Polymer 3

TABLE 5

| Blank polymer 3 | time, h | $M_n$, Da | PD | $Y_p$, % | $P_n$ |
|---|---|---|---|---|---|
| | 3 | 1500 | 1.3 | 52 | 5 |
| | 22 | 3500 | 1.8 | 77 | 12 |
| | 36 | 5500 | 3.7 | 57 | 19 |

[$M_p$: molecular weight at peak maximum; $M_n$: number-mean molecular weight; PD: polydispersity; $Y_p$: yield of polymerisation; $P_n$: number-mean degree of polymerization].

Preparative Example for the Preparation of Nanoparticles of a Blank Polymer 3 Made from Dimethyl-2-Oxoglutarate and Triethylene Glycol Nanoparticles were prepared from blank polymer 3 prepared above in the same manner as the nanoparticles prepared from blank polymer 1 above.

The particle size and zeta potential of the polymer nanoparticles were measured by DLS as shown in Table 6. An aliquot of the final dispersion was diluted in water.

DLS Characterization of Polymeric Nanoparticles

TABLE 6

| Blank polymer 3 | Z-average ± PDI width d, nm | $d_{Number}$, nm | PDI | zeta potential ± zeta deviation, mV |
|---|---|---|---|---|
| water | 630 ± 462 | 304 | 0.527 | −19 ± 12 |

Z-average: cumulants mean; $d_{Number}$: number-mean size; PDI: polydispersity index.

Preparative Example for the Synthesis of a Blank Polymer 4 Made from Dimethyl-2-Oxoglutarate and N-Methyldiethanolamine

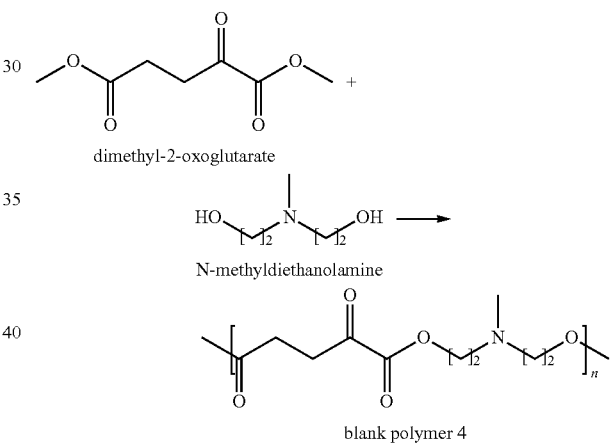

Blank polymer 4 was prepared by reacting dimethyl-2-oxoglutarate and N-methyldiethanolamine using the same polymerisation process as that described for the preparation of blank polymer 1 above.

Figure 9:
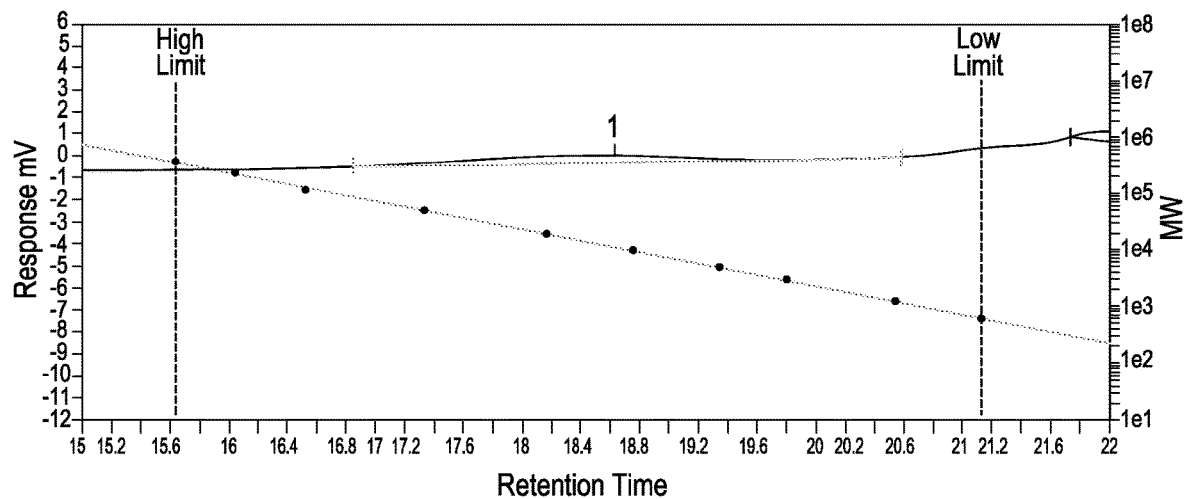
FIG. 9 is a graph showing Gel Permeation Chromatography (GPC) analysis of blank polymer 4 after a 4 h polymerization time.

The GPC analysis for blank polymer 4 after a 4 h polymerization time is shown in FIG. 9. The dashed lines indicate the high and low limits of molecular weight calibration. The square data points represent calibration data.

Table 7 indicates the polymer size and dispersity for the blank polymer 4 synthesised.

Polymer Size and Dispersity of Blank Polymer 4

TABLE 7

| Blank polymer 4 | time, h | $M_n$, Da | PD | $Y_p$, % | $P_n$ |
|---|---|---|---|---|---|
| | 4 | 11242 | 1.75 | 34 | 46 |

[$M_p$: molecular weight at peak maximum; $M_n$: number-mean molecular weight; PD: polydispersity; $Y_p$: yield of polymerisation; $P_n$: number-mean degree of polymerization].

Example 1: Synthesis of Isoniazid-Containing Polymer Nanoparticles from Blank Polymer 1

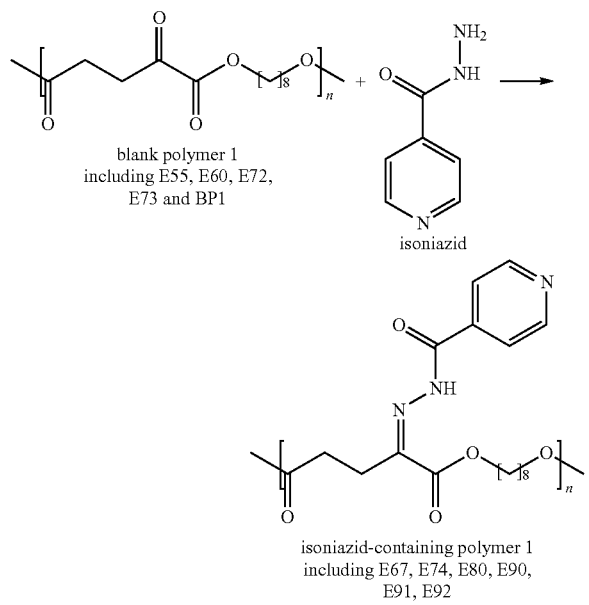

blank polymer 1
including E55, E60, E72, E73 and BP1 isoniazid isoniazid-containing polymer 1
including E67, E74, E80, E90, E91, E92

INH-containing polymers including E67 (E67 INH), E74A, E74B, E80 (E80 INH), E90 (E90 INH), E91 (E91 INH) and E92 (E92 INH) were prepared from blank polymers 1 including E55 (E55 blank), E72 (E72 blank), E73 and BP1 as shown in Table 8. Blank polymers E55, E72, E73 and BP1 were prepared as described above. INH was then covalently linked to the carbonyl groups of the blank polymers by solubilizing the polymer in DMSO. INH (1.2 eq. molar amounts of estimated carbonyl groups in the polymer) was then added and the resultant mixture was stirred at 200 rpm at room temperature (or 37° C.) for the reaction time. The solution was then added dropwise to ethanol (50 mL) and the precipitated polymers were sedimented by centrifugation and dried. The size of each of the polymers was measured by GPC analysis as described above. Table 8 gives data for the characterisation of each of the INH-containing polymers synthesized.

Characterisation of INH-Containing Polymers

TABLE 8

| Name | Name bp | time | temp. | yield (%) | $M_p$, Da | $M_n$, Da | PD | $\Delta M_n$, % |
|---|---|---|---|---|---|---|---|---|
| E67 | E55 | 30 min | room temp. | N/A | 8491 | 7121 | 1.35 | 77.4 |
| E74A | E72 | 30 min | room temp. | N/A | 27668 | 22594 | 1.93 | 37.2 |
| E74B | E73 | 30 min | room temp. | N/A | 13356 | 10178 | 1.61 | 33.0 |
| E80 | E72 | 35 min | room temp. | N/A | 17026 | 15987 | 2.40 | −2.9 |
| E90 | BP1 | 30 min | room temp. | 30-60 | N/A | 5500-15041 | 1.1-1.5 | N/A |
| E91 | BP1 | 24 h | room temp. | 47 | N/A | 2300 | 1.2 | N/A |
| E92 | BP1 | 72 h | 37° C. | 70 | N/A | 1300-2100 | 1.7-1.8 | N/A |

[bp: blank polymer; $M_p$: molecular weight at peak maximum; $M_n$: number-mean molecular weight; PD: polydispersity; $\Delta M_n$: procentual increase of $M_n$ in respect to blank polymer]. BP1 = blank polymer 1

Figure 10:
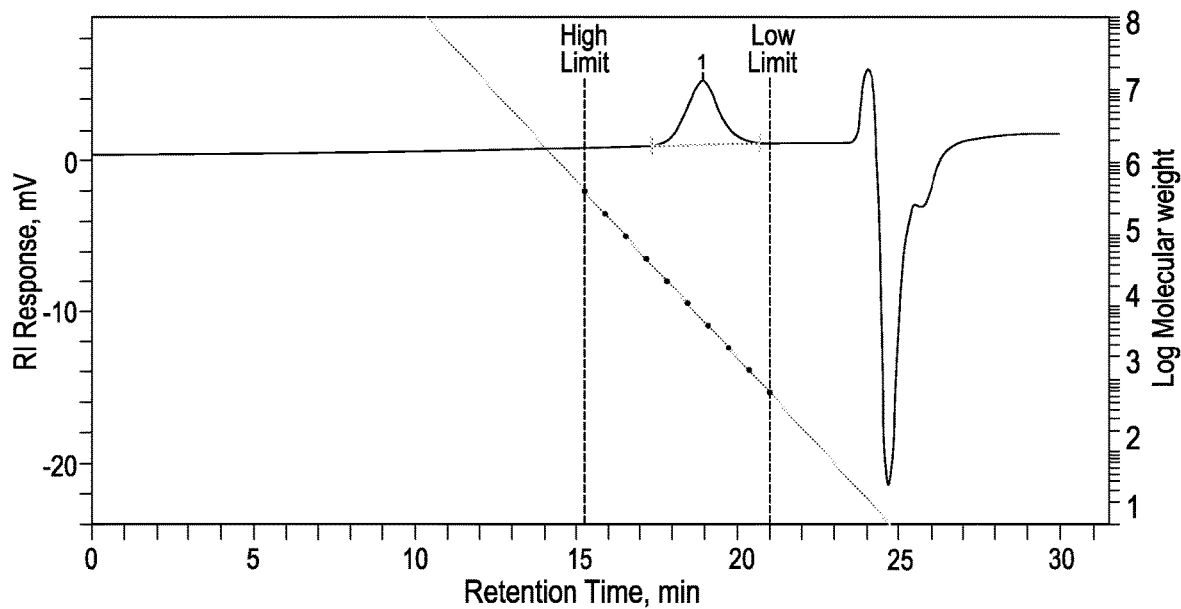
FIG. 10 is a graph showing GPC analysis of polymer E67 after a 30 min incubation time.

FIG. 10 shows the GPC analysis of polymer E67 after 30 min incubation. Dashed lines indicate the high and low limit of molecular weight calibration. The square data points represent calibration data.

Figure 11:
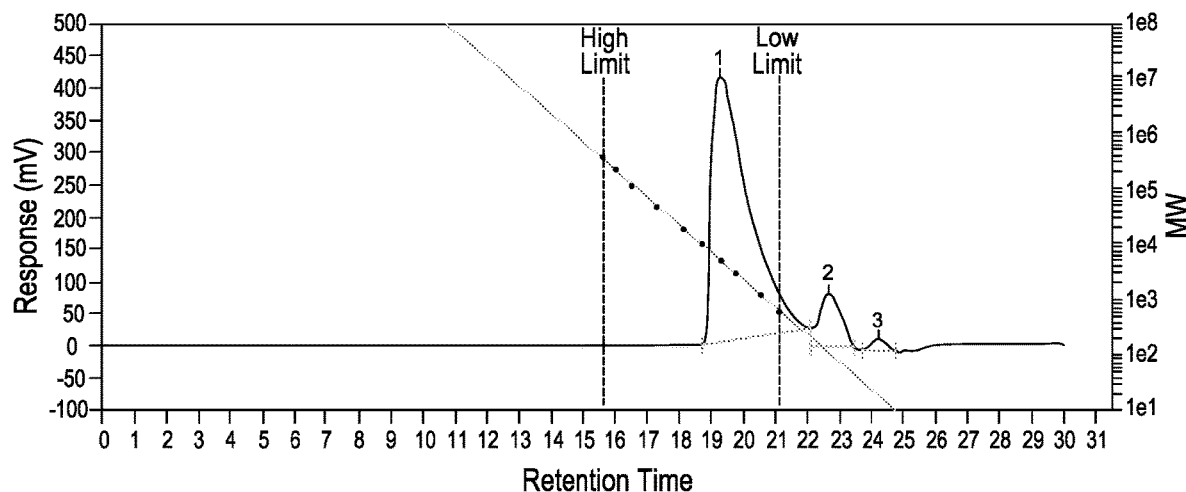
FIG. 11 is a graph showing GPC analysis of blank polymer 1 incorporating INH after a 72 h incubation time.

FIG. 11 shows the GPC analysis of blank polymer 1 after 72 h incubation with INH. Dashed lines indicate the high and low limit of molecular weight calibration. The square data points represent calibration data.

Figure 12:
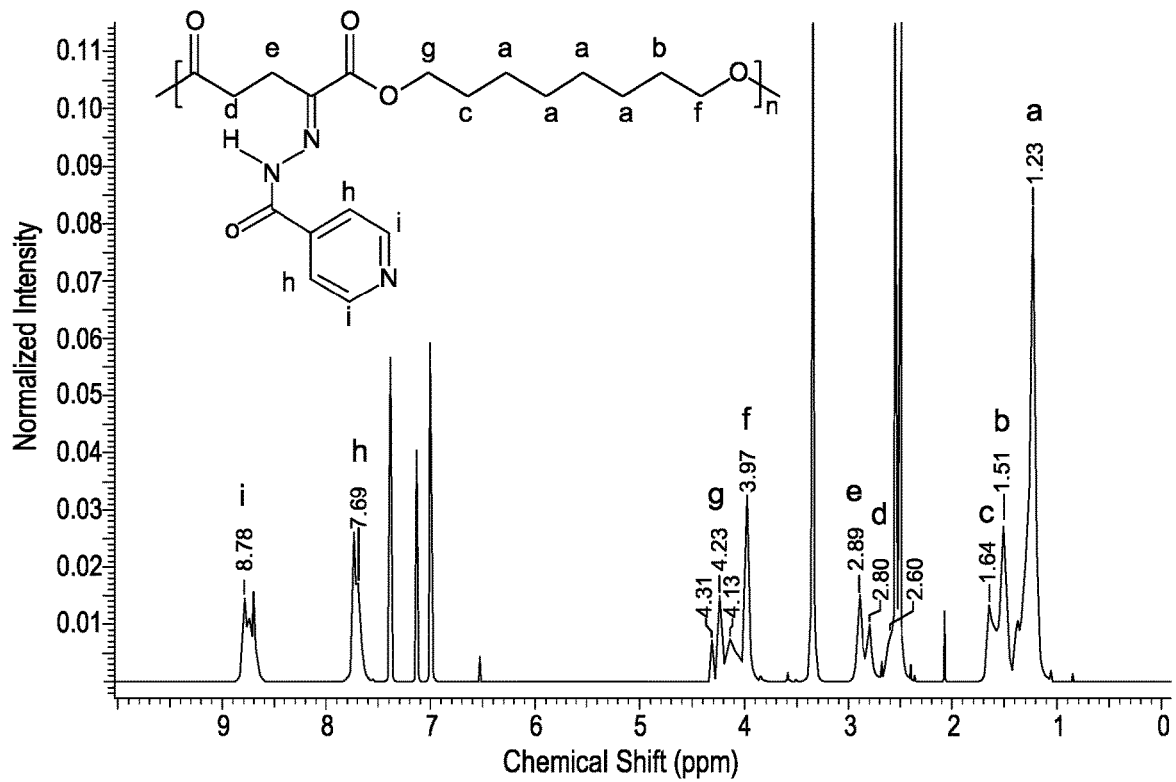
FIG. 12 is a $^1$H-NMR spectrum of blank polymer 1 incorporating INH in DMSO-d6.

FIG. 12 shows the $^1$H NMR spectrum of blank polymer 1 incorporating INH in DMSO-d6.

The polymers were formulated into nanoparticles and characterised as described above. The DLS characterisation results are detailed in Table 9.

DLS Characterization of Polymeric Nanoparticles

TABLE 9

| polymer | Z-average ± PDI width d, nm | $d_{Number}$, nm | PDI | zeta potential, mV |
|---|---|---|---|---|
| E67 INH | | | | |
| pH 5 | 158 ± 34 | 133 ± 6 | 0.05 ± 0.02 | −55 ± 2 |
| pH 7.4 | 156 ± 36 | 131 ± 7 | 0.06 ± 0.03 | −72 ± 5 |
| E80 INH | | | | |
| pH 5 | 195 ± 45 | 170 ± 6 | 0.06 ± 0.03 | −37 ± 2 |
| pH 7.4 | 190 ± 51 | 159 ± 7 | 0.07 ± 0.02 | −71 ± 4 |

Z-average: cumulants mean;; $d_{Number}$: number-mean size; values ± standard deviation of DLS measurement runs; PDI: polydispersity index.

Figure 13:
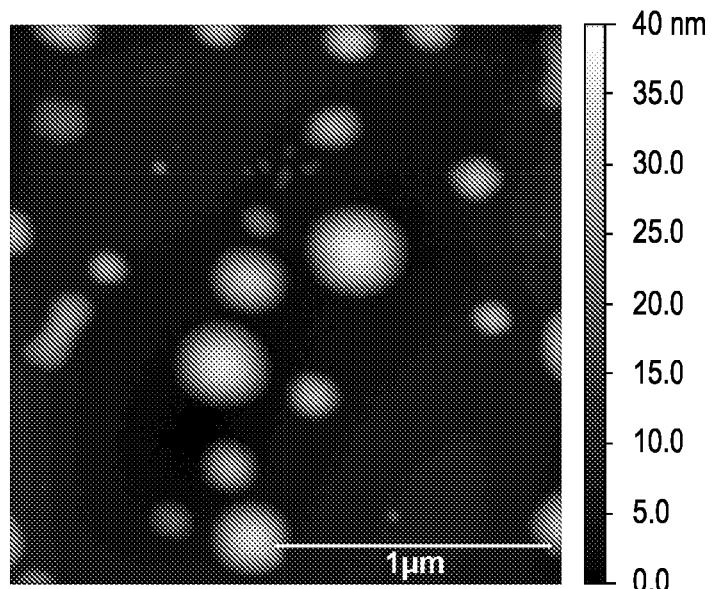
FIG. 13 is an AFM image of E67 nanoparticles.

FIG. 13 shows nanoparticles of E67 with heights ranging from 20-35 nm and widths ranging from 120-400 nm. Deformation of the nanoparticles on the mica substrate was observed, which was attributed to the drying of nanoparticles for imaging.

Figure 14:
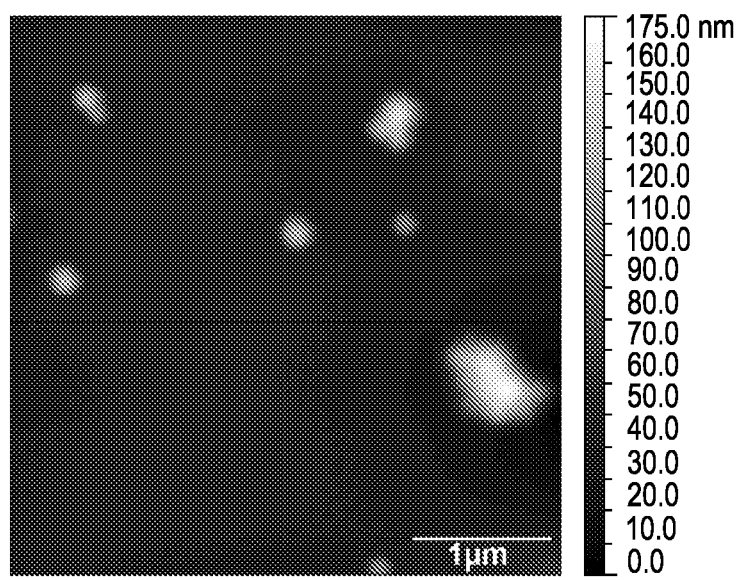
FIG. 14 is an AFM image of E80 nanoparticles.

FIG. 14 shows nanoparticles of E80 with heights ranging from 70-90 nm and widths ranging from 300-400 nm. Deformation of the nanoparticles was observed on the mica substrate, which was attributed to the drying of nanoparticles for imaging.

The INH loading of each of the polymers was then assessed. Quantification of INH was assessed via HPLC as described above in the analysis methods. Table 10 shows the results of drug release from nanoparticles E67, E80, E90, E91 and E92. INH release was measured by HPLC after incubation of the nanoparticles in 0.5 and 1 M NaOH for 24 h at 60° C. The drug content is specified in respect to the dry mass of nanoparticles.

Drug Loading

TABLE 10

| nanoparticles | $c_{drug}$, mg/mL | $c_{np}$, mg/mL | $L_{drug}$, wt % |
|---|---|---|---|
| E67 INH | 0.080 | 1.4 | 6 |
| E80 INH | 1.046 | 2.5 | 42 |
| E90 INH | 0.02-0.045 | N/A | 2-4.5 |

TABLE 10-continued

| nanoparticles | $c_{drug}$, mg/mL | $c_{np}$, mg/mL | $L_{drug}$, wt % |
|---|---|---|---|
| E91 INH | 0.47 | N/A | 47 |
| E92 INH | 0.28-0.64 | N/A | 19-26 |

[$c_{drug}$ = drug concentration; $c_{np}$ = nanoparticle concentration, $L_{drug}$, drug loading wt %].

The E67 INH nanoparticles were also degraded in 10 mM citrate buffer pH 5 at 37° C. After 24 h, a drug release of 0.4 wt. % was quantified.

Example 2: Synthesis of Rifampicin-Containing Polymer Nanoparticles from Blank Polymer 1

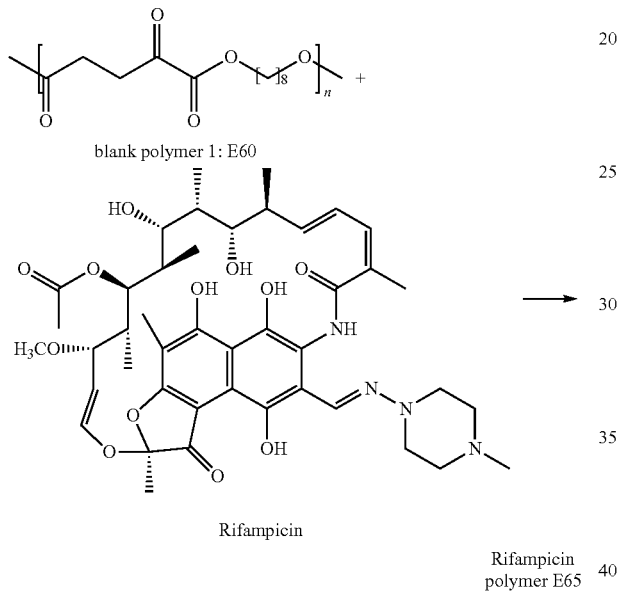

Rifampicin (RIF) polymer E65 was produced by enzymatic linkage of RIF to blank polymer 1 E60. Blank polymer E60 was synthesized as described above. The blank polymer 1 was then dissolved in diphenyl ether (3 mL) at 60° C. A molar amount of RIF was then added to the solution followed by *Candida Antarctica* Lipase B (CALB) as immobilized enzyme (Novozym™ 435, N435. N435 contains 10% w/w CALB and 90% w/w acrylic resin). The reaction mixture was stirred under vacuum for 75 min at 60° C. Molecular weight increase was confirmed by GPC analysis. The enzyme was filtered off and the fluid was washed in diethyl ether (3×45 ml). Residual diethyl ether was evaporated by flushing with nitrogen followed by incubation in a desiccator overnight.

Figure 15:
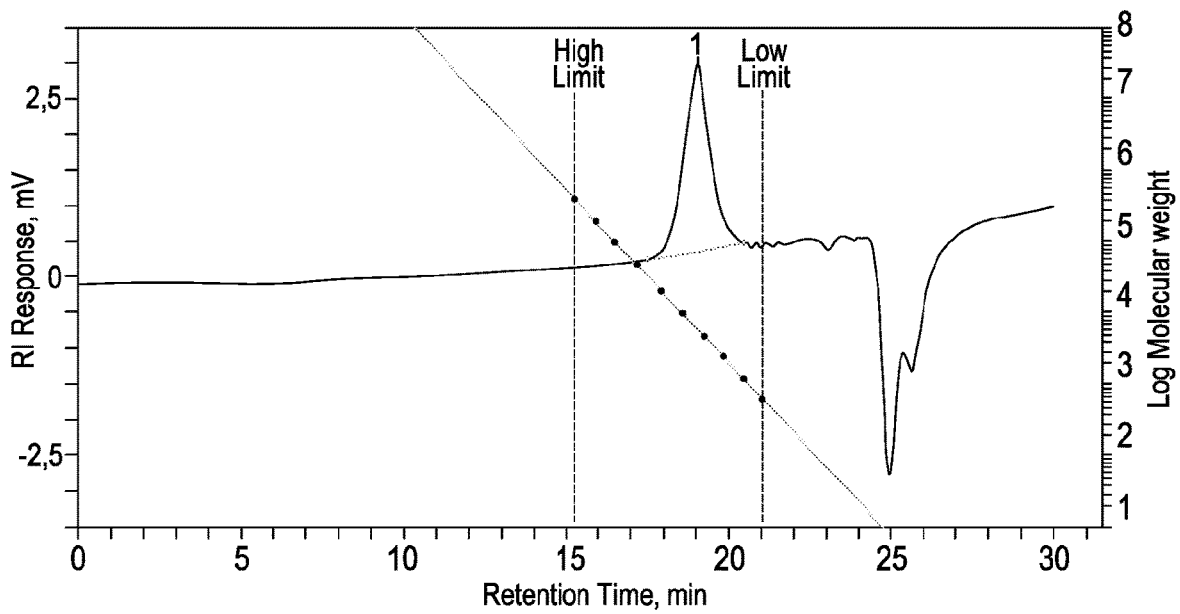
FIG. 15 is a graph showing the GPC analysis of polymer E65.

FIG. 15 shows the GPC analysis of polymer E65. The dashed lines indicate the high and low limits of molecular weight calibration. The square data points represent calibration data. After 75 mins, the reaction was terminated and a polymer with $M_p/M_n$=7188/6467 Da and PD=1.25 was obtained.

The polymers were formulated into nanoparticles and characterised as described above. The DLS characterisation results are detailed in Table 11.

DLS Characterization of Polymeric Nanoparticles

TABLE 11

| polymer | Z-average ± PDI width d, nm | $d_{Number}$, nm | PDI | zeta potential, mV |
|---|---|---|---|---|
| E65 RIF | | | | |
| pH 5 | 177 ± 57 | 143 ± 4 | 0.11 ± 0.04 | −77 ± 5 |
| pH 7.4 | 173 ± 53 | 139 ± 5 | 0.10 ± 0.02 | −61 ± 8 |

Z-average: cumulants mean;; $d_{Number}$: number-mean size; values ± standard deviation of DLS measurement runs; PDI: polydispersity index.

Example 3: Synthesis of Ciprofloxacin-Containing Polymer Nanoparticles from Blank Polymer 1

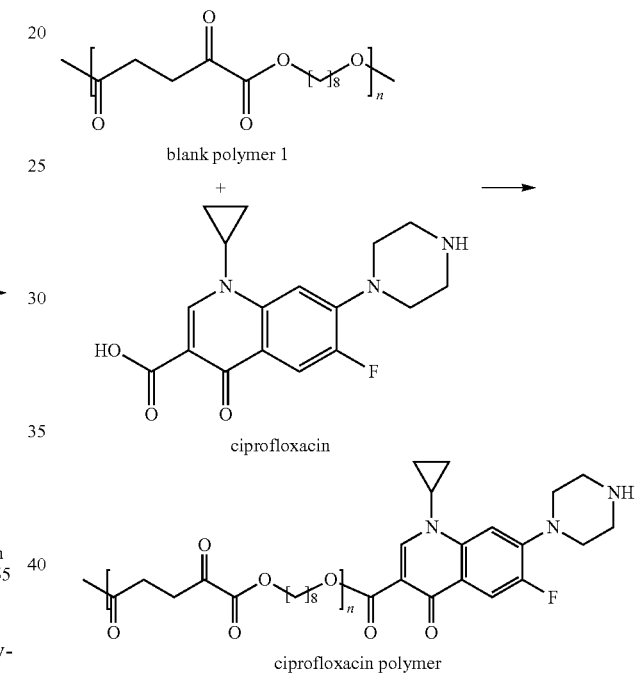

This illustrates the preparation of a biologically active molecule containing polymer of the present invention which is able to bind the biologically active molecule via the formation of an ester bond.

Ciprofloxacin-containing polymer was prepared from blank polymer 1. Blank polymer 1 was prepared as described above. Ciprofloxacin (10.7 mg, 32.4 µmol) and blank polymer 1 (100 mg, 27.0 µmol) were combined with DIPEA (282 µL, 162 µmol) and HBTU (12.3 mg, 32.4 µmol) in 1 mL of DCM. The reaction mixture was stirred at room temperature for 4 hours. The reaction mixture was diluted with DCM and poured in water in an extraction vessel. The water phase was back-extracted twice with DCM. Organic layers were combined, washed with water and brine then dried over MgSO$_4$. Solvent was evaporated and the orange solid (94 mg, 86%) was dried overnight in a dessicator.

The polymers were formulated into nanoparticles in the same manner as described in Example 1 and characterised as described above. The DLS characterisation results are detailed in Table 12.

DLS Characterization of Polymeric Nanoparticles

TABLE 12

| ciprofloxacin-containing polymer | Z-average ± PDI width d, nm | $d_{Number}$, nm | PDI | zeta potential ± zeta deviation, mV |
|---|---|---|---|---|
| water | 161 ± 40 | 134 | 0.062 | N/A |
| pH 5 | 178 ± 50 | 152 | 0.065 | −54 ± 10 |
| pH 7.4 | 176 ± 44 | 148 | 0.065 | −70 ± 10 |

Z-average: cumulants mean;; $d_{Number}$: number-mean size; PDI: polydispersity index.

The drug loading of the polymer was then assessed. 100 µL of nanoparticles were incubated at 60° C. with 100 µL NaOH 1 M. After 48 h the suspension was centrifuged for 2 min at 13000 rpm then 20 µL of the supernatant was collected and analysed by HPLC. A ten-point standard curve was made by serial dilution of the required drug in NaOH 0.5 M. Nanoparticle dry mass was determined by lyophilisation of a 200 µL sample.

Figure 16:
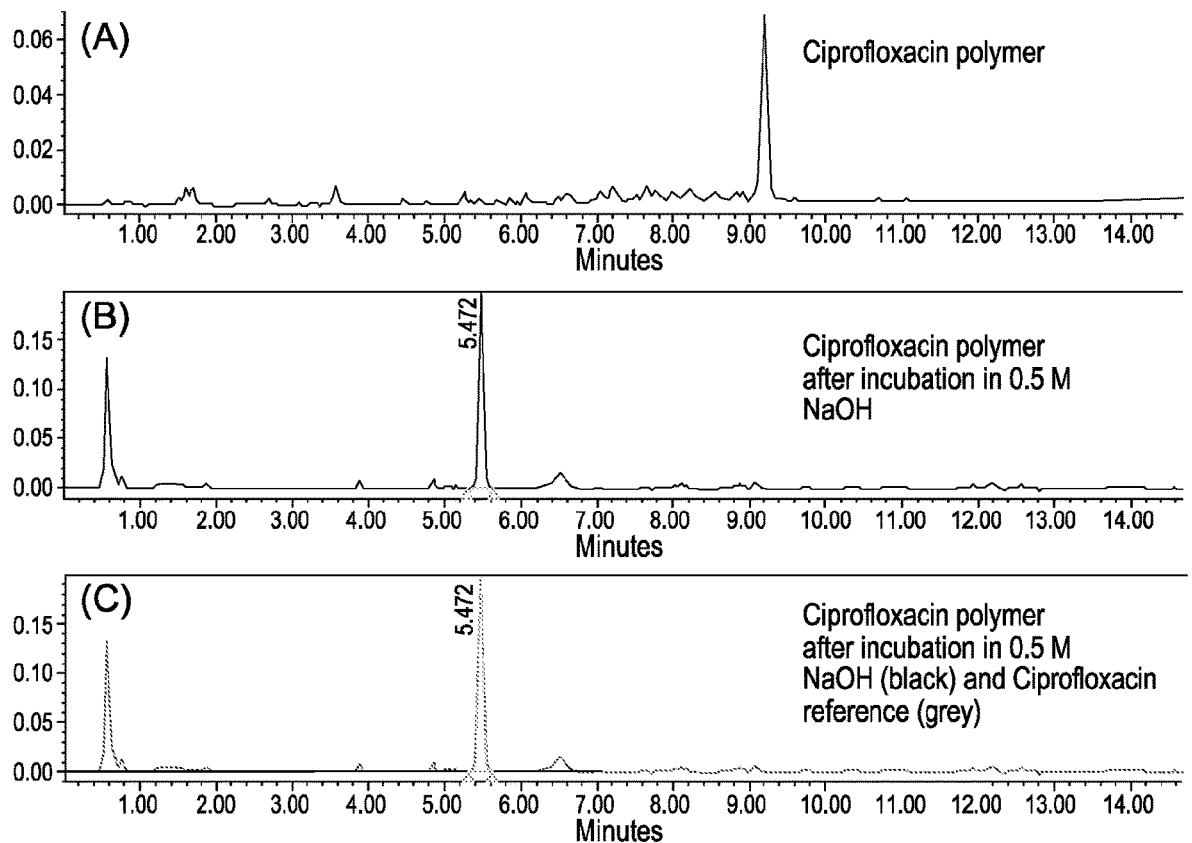
FIG. 16 is graph showing the HPLC analysis used for the characterisation of ciprofloxacin-containing polymer.

FIG. 16 is a graph showing RP-HPLC analysis of ciprofloxacin polymer (A), sample from supernatant after incubation of particles made with the polymer incorporating ciprofloxacin in 0.5 M NaOH (B); sample from supernatant after incubation of particles made with the polymer incorporating ciprofloxacin in 0.5 M NaOH with ciprofloxacin reference (C).

Table 13 shows the results of drug release from ciprofloxacin-containing polymer nanoparticles. Drug release was measured by HPLC after incubation of the nanoparticles in 0.5 M NaOH for 48 h at 60° C. The drug content is specified in respect to the dry mass of nanoparticles.

Drug Loading

TABLE 13

| nanoparticles | $c_{drug}$, mg/mL | $c_{np}$, mg/mL | $L_{drug}$, wt % |
|---|---|---|---|
| ciprofloxacin-containing polymer | 0.014 | 1.0 | 1.4 |

[$c_{drug}$ = drug concentration; $c_{np}$ = nanoparticle concentration, $L_{drug}$, drug loading wt %].

Example 4: Synthesis of Memantine-Containing Polymer from Blank Polymer 1

This illustrates the preparation of a biologically active molecule containing polymer of the present invention which is able to bind the biologically active molecule via the formation of an imine bond.

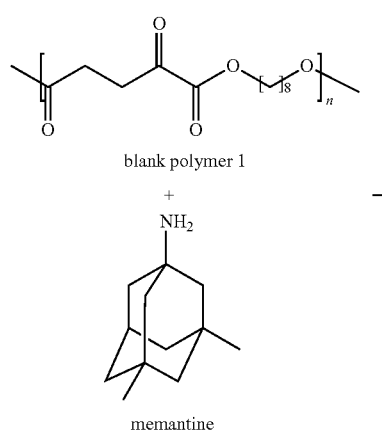

blank polymer 1
+
memantine

→

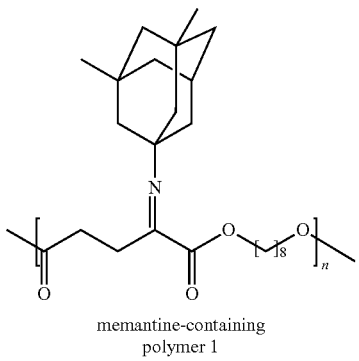

memantine-containing polymer 1

Memantine-containing polymer 1 was prepared from blank polymer 1. Blank polymer 1 was prepared as described above. Blank polymer 1 (50 mg, 8 µmol) was solubilized in anhydrous toluene. p-Toluenesulfonic acid was added in catalytic amount, and the free base of memantine (28 mg, 158 µmol) was added to the toluene mixture. A Dean-Stark set up was adapted to a round-bottom flask, and the reaction mixture was heated up to 84° C. The reaction was stirred for 30 minutes. Reaction product was retrieved by evaporation of toluene and the resulting product was dried in a desiccator.

Figure 17:
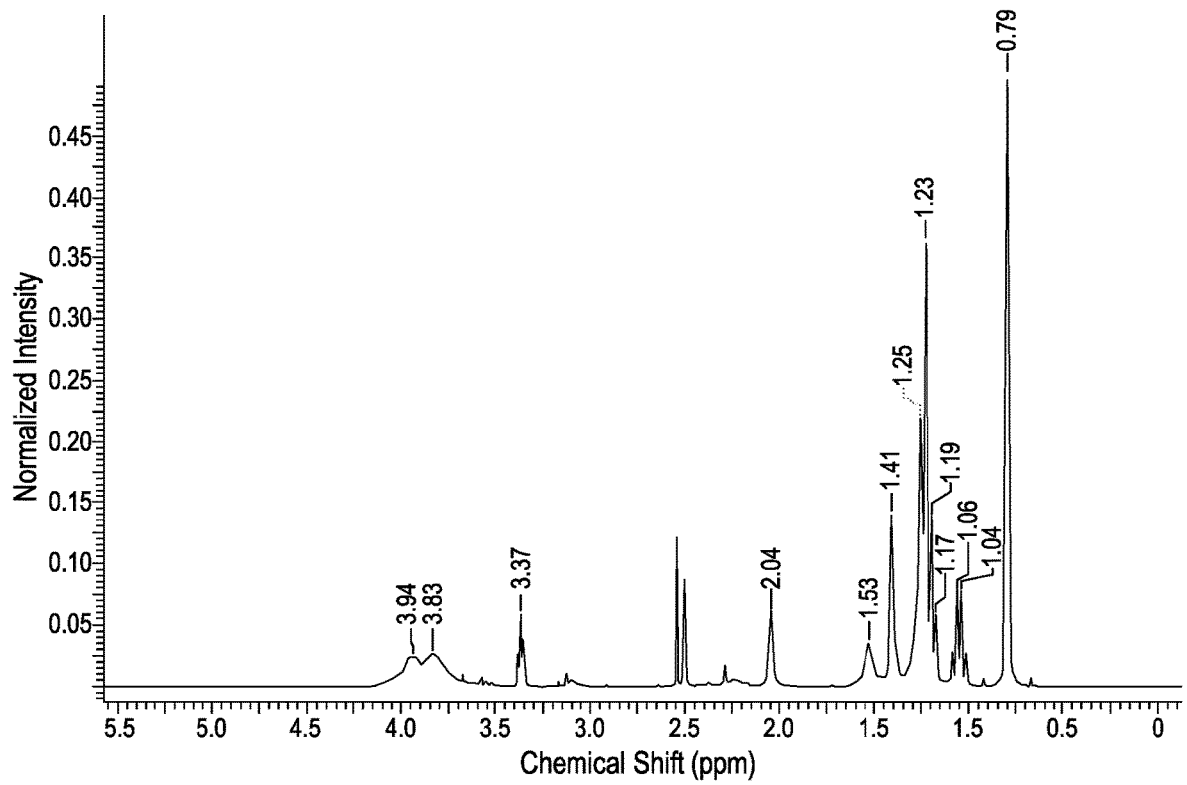
FIG. 17 is a $^1$H NMR spectrum of memantine-containing polymer 1 in DMSO-d6.

FIG. 17 shows the $^1$H NMR spectrum of the memantine-containing polymer in DMSO-d6. The $^1$H-NMR spectroscopy analysis in FIG. 17 shows a singlet at 0.79 ppm which is attributed to the two methyl groups of memantine. The other protons of memantine appear in the range of 1 to 2.1 ppm together with the protons of the backbone of the blank polymer 1 as shown in FIG. 2.

Example 5: Synthesis of o-Benzylhydroxamine-Containing Polymer from Blank Polymer 1

This illustrates the preparation of a biologically active molecule containing polymer of the present invention which is able to bind the biologically active molecule via the formation of an oxime bond.

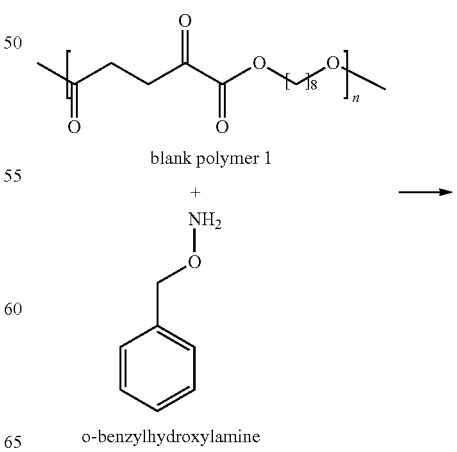

blank polymer 1
+
o-benzylhydroxylamine

→

-continued

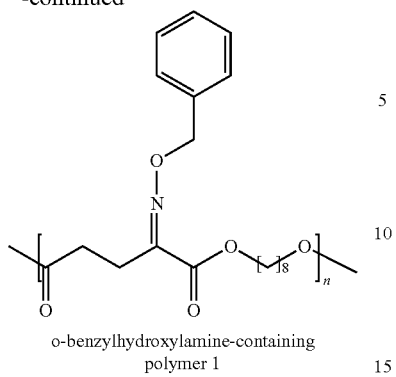

o-benzylhydroxylamine-containing polymer 1 o-Benzylhydroxylamine-containing polymer was prepared from blank polymer 1. Blank polymer 1 was prepared as described above. Blank polymer 1 (30 mg, 5 μmol) and o-benzylhydroxylamine (19 mg, 119 μmol) were solubilized separately in anhydrous DMSO. Both solutions were mixed in a round-bottom flask with mechanical stirring, p-Toluenesulfonic acid was added in catalytic amount. Vacuum was applied, and reaction was stirred during 48 h. Reaction product was retrieved by precipitation of the reaction mixture in aqueous buffer and water (pH 9).

Figure 18:
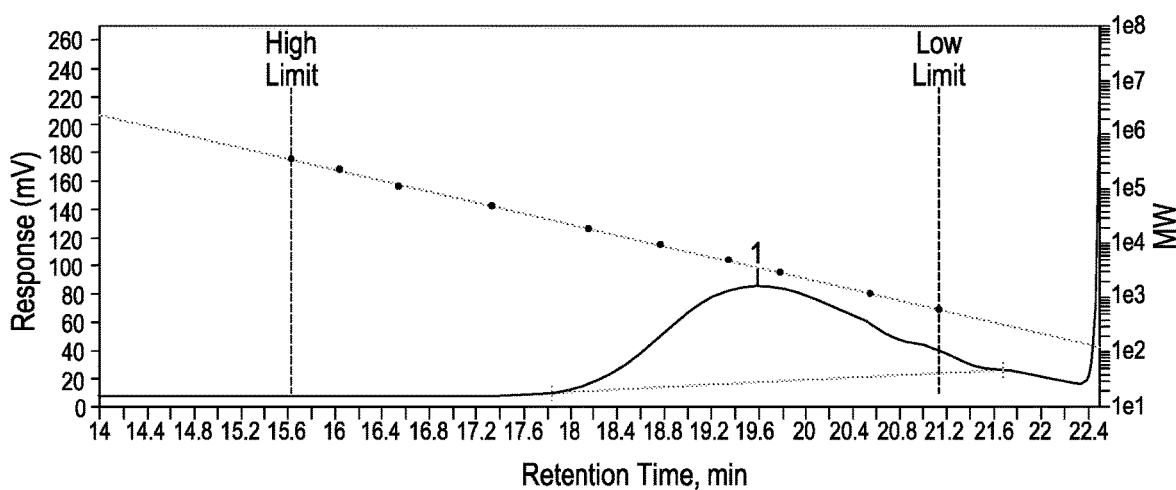
FIG. 18 is a graph showing GPC analysis of o-benzylhydroxylamine-containing polymer 1 after 48 h incubation time.

FIG. 18 shows the GPC analysis of the o-benzylhydroxylamine-containing polymer after 48 h incubation time. Dashed lines indicate the high and low limit of molecular weight calibration. The square data points represent calibration data.

Figure 19:
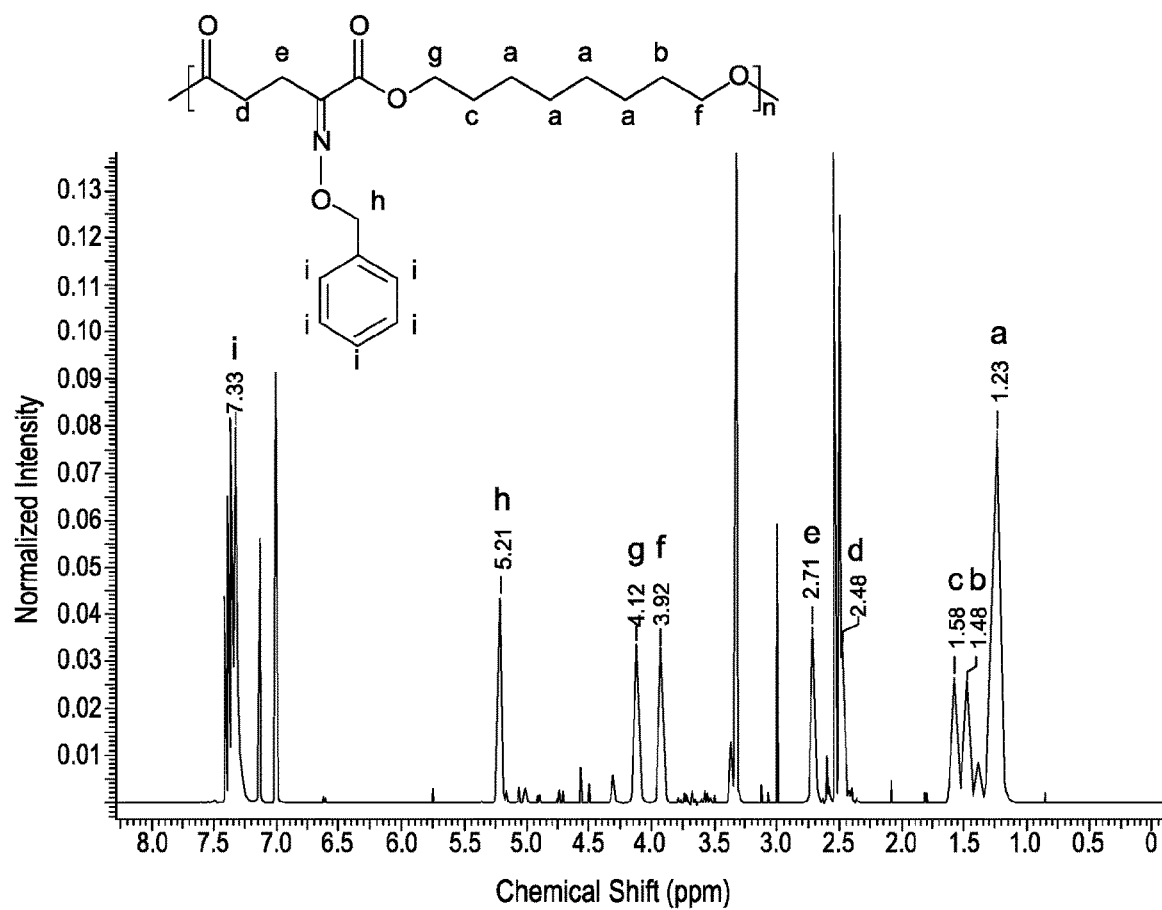
FIG. 19 is a $^1$H-NMR spectrum of o-benzylhydroxylamine-containing polymer 1 in DMSO-d6.

FIG. 19 shows the $^1$H-NMR spectrum of the o-benzylhydroxylamine-containing polymer 1 in DMSO-d6.

Example 6: Synthesis of Prednisone-Containing Polymer from Blank Polymer 1

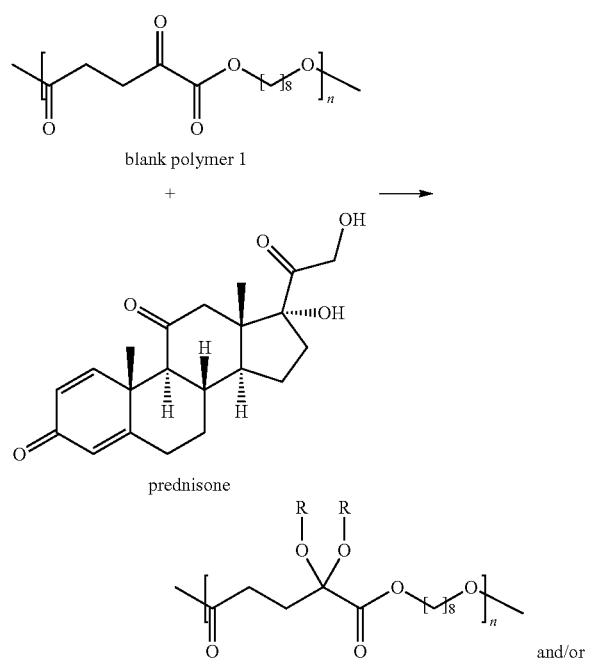

-continued

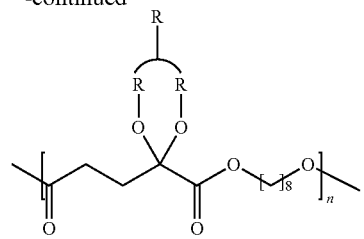

R=

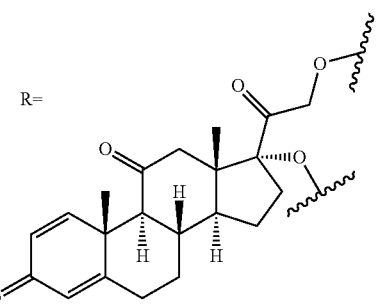

This illustrates the preparation of a biologically active molecule containing polymer of the present invention which is able to bind the biologically active molecule via the formation of a ketal bond.

Prednisone-containing polymer 1 was prepared from blank polymer 1. Blank polymer 1 was prepared as described above. Blank polymer 1 (50 mg, 8 μmol) and prednisone (56 mg, 158 μmol) were solubilized separately in anhydrous DMSO. Both solutions were mixed in a round-bottom flask with mechanical stirring. p-Toluenesulfonic acid was added in catalytic amount. Vacuum was applied, and reaction was stirred during 72 h. Reaction product was retrieved by precipitation of the reaction mixture and washes in aqueous buffer (pH 9) and water.

Figure 20:
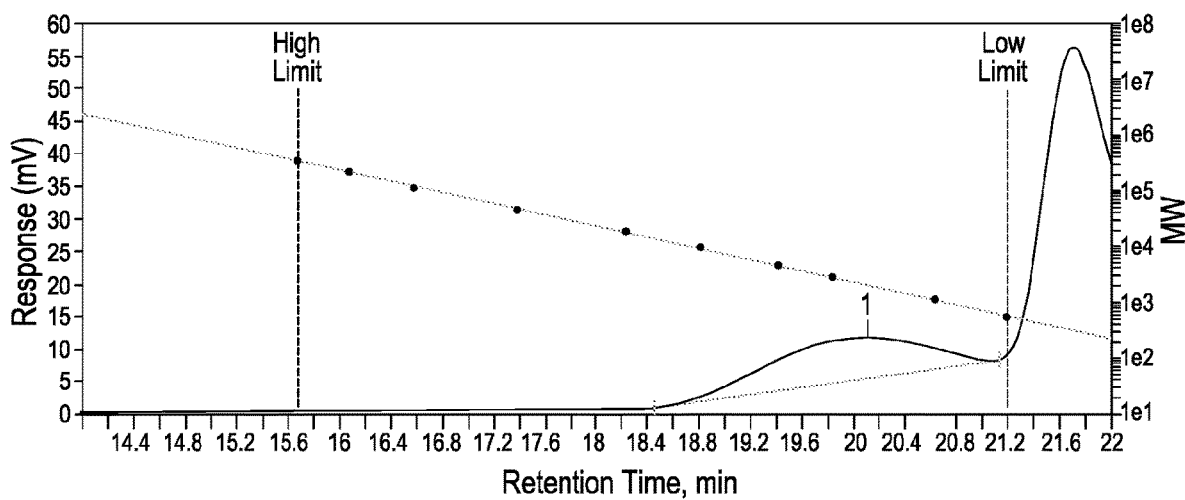
FIG. 20 is a graph showing GPC analysis of prednisone-containing polymer 1 after 48 h incubation time.

FIG. 20 shows the GPC analysis of the prednisone-containing polymer after 72 h incubation time. Dashed lines indicate the high and low limit of molecular weight calibration. The square data points represent calibration data.

Figure 21:
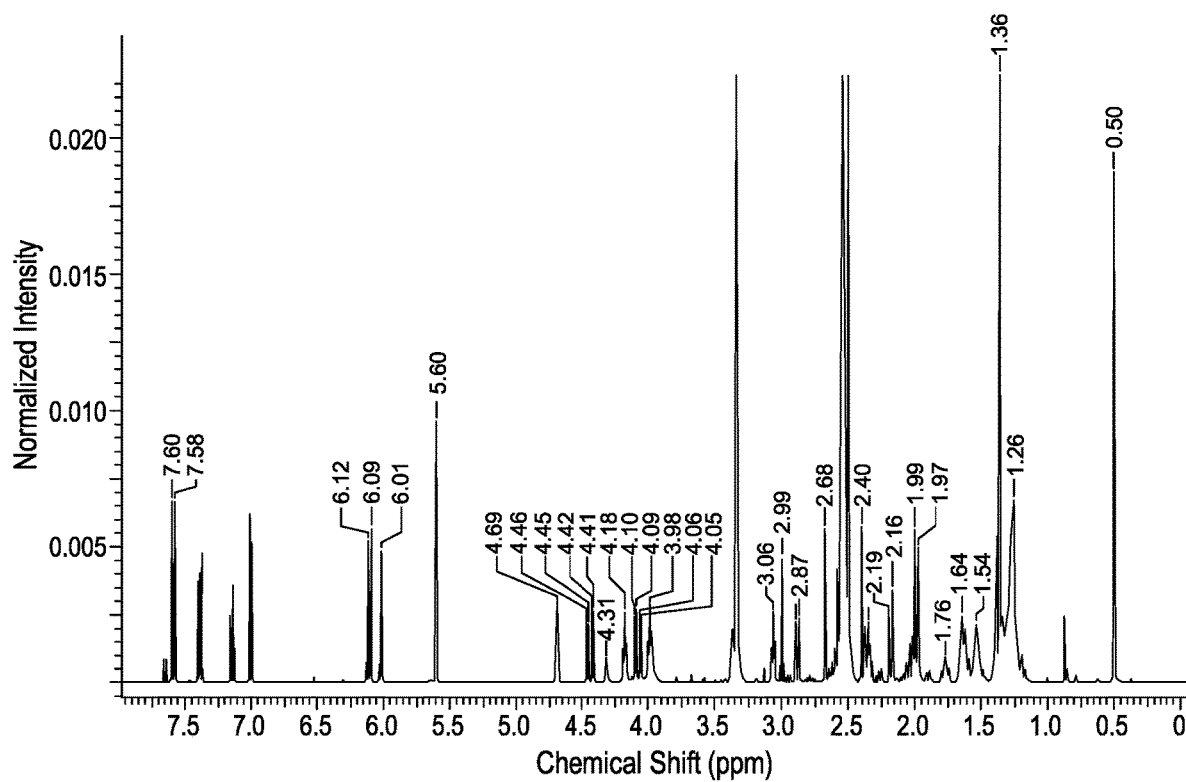
FIG. 21 is a $^1$H-NMR spectrum of prednisone-containing polymer 1 in DMSO-d6.

FIG. 21 shows the $^1$H-NMR spectrum of the prednisone-containing polymer 1 in DMSO-d6. The $^1$H-NMR spectroscopy analysis in FIG. 21 shows peaks which are attributable to the protons of prednisone and to the protons of blank polymer 1 as shown in FIG. 2.

Example 7: Synthesis of Ethambutol-Containing Polymer Nanoparticles

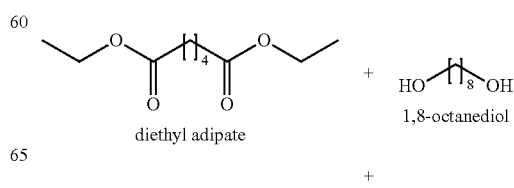

diethyl adipate    1,8-octanediol

+

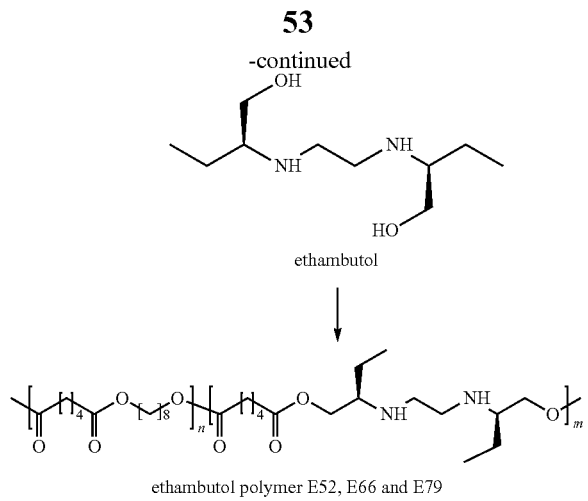

ethambutol ethambutol polymer E52, E66 and E79

Polymers containing ethambutol (EMB) were synthesized using the same procedure described above for the preparation of a blank polymer.

The EMB polymers E52 (E52 EMB), E66 (E66 EMB) and E79 (E79 EMB) contained diethyl adipate as the diester component. The diol components consisted of 77 mol % ethambutol and 23 mol % 1,8-octanediol to increase molecular weight by addition of a favorable substrate for the enzyme. EMB polymers were purified by two-fold precipitation in hexane in an analogous fashion to the purification of the blank polymers.

Figure 22:
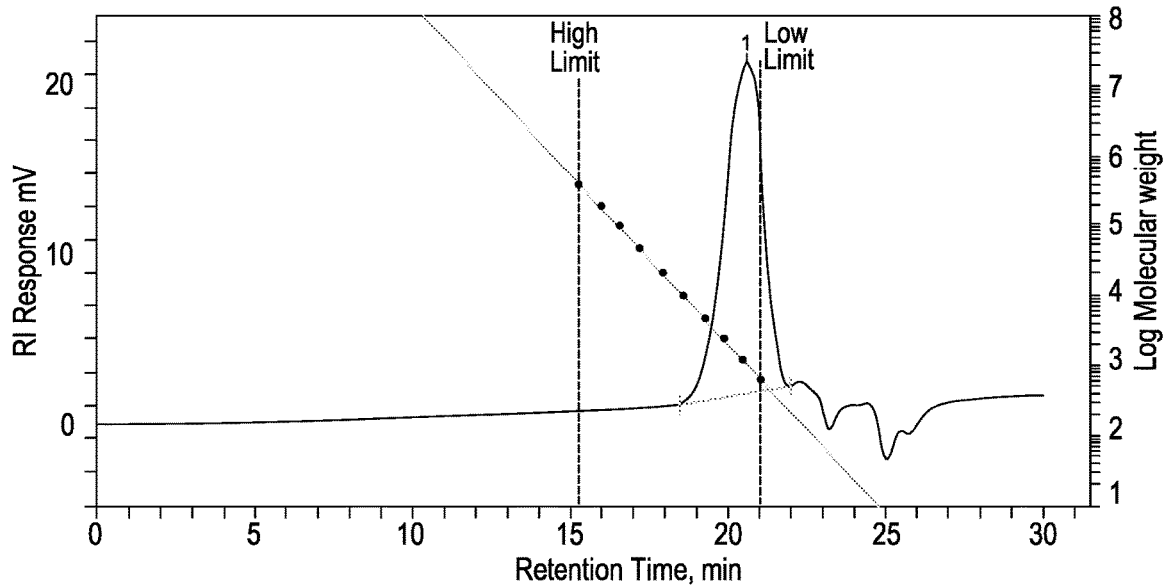
FIG. 22 is a graph showing the GPC analysis of polymer E52 after a 49 h polymerization time.

FIG. 22 shows the GPC analysis of polymer E52 after reaction for 49 h in diphenyl ether at 90° C. and purification by precipitation in hexane. The dashed lines indicate the high and low limits of molecular weight calibration. The square data points represent calibration data. After 49 h, the reaction was terminated and a polymer with $M_p/M_n$=2569/1858 Da and PD=1.60 was obtained.

The polymers were formulated into nanoparticles and characterised as described above. The DLS characterisation results are detailed in Table 14.

DLS Characterization of Polymeric Nanoparticles

TABLE 14

| polymer | Z-average ± PDI width d, nm | $d_{Number}$, nm | PDI | zeta potential, mV |
|---|---|---|---|---|
| E52 EMB | | | | |
| pH 5 | 156 ± 53 | 112 ± 12 | 0.12 ± 0.02 | +16 ± 1 |
| pH 7.4 | 167 ± 57 | 124 ± 8 | 0.12 ± 0.02 | −40 ± 4 |
| E66 EMB | | | | |
| pH 5 | 442 ± 223 | 343 ± 91 | 0.25 ± 0.06 | +14 ± 1 |
| pH 7.4 | 352 ± 179 | 249 ± 12 | 0.26 ± 0.06 | −25 ± 3 |
| E79 EMB | | | | |
| pH 5 | 286 ± 129 | 223 ± 32 | 0.20 ± 0.03 | +14 ± 1 |
| pH 7.4 | 356 ± 237 | 183 ± 20 | 0.44 ± 0.06 | +11 ± 2 |

Z-average: cumulants mean;; $d_{Number}$: number-mean size; values ± standard deviation of DLS measurement runs; PDI: polydispersity index.

The EMB loading of each of the polymers was then assessed. Quantification of EMB was initially assessed as described in the analysis methods above.

Table 15 shows the results of drug release from nanoparticles E52 and E66. EMB release was measured by HPLC after incubation of the nanoparticles in 1 M NaOH for 24 h at 60° C. The drug content is specified in respect to the dry mass of nanoparticles.

Drug Loading

TABLE 15

| nanoparticles | $c_{drug}$, mg/mL | $c_{np}$, mg/mL | $L_{drug}$, wt % |
|---|---|---|---|
| E52 EMB | 0.797 | 5.0 | 16 |
| E66 EMB | 0.519 | 3.0 | 17 |

[$c_{drug}$ = drug concentration; $c_{np}$ = nanoparticle concentration, $L_{drug}$, drug loading wt %].

Example 8: Preparation of Polymer Nanoparticles with Encapsulated Rifampicin

Nanoparticles encapsulating rifampicin (RIF) were prepared using blank polymer E72 and INH-containing polymer E80. The nanoparticles were prepared as described above for blank polymer 1 with several concentrations of RIF from 2 to 40 mg·mL$^{-1}$ in the acetonitrile/polymer phase.

RIF quantification was determined by UV spectrometry at 475 nm. A five-point standard curve was made by preparing solutions of rifampicin in acetonitrile (linear regression: Abs.=16.64*$c_{RIF}$, $R^2$=99.8%).

Table 16 shows the results of drug release from nanoparticles encapsulating RIF. Drug release was measured by UV spectroscopy after dissolution of the nanoparticles in acetonitrile. The drug content is specified in respect to the dry mass of nanoparticles.

Drug Loading

TABLE 16

| nanoparticles | $c_{drug}$, mg/mL | $c_{np}$, mg/mL | $L_{drug}$, wt % |
|---|---|---|---|
| E72 blank RIF | 0.012 | 1.0 | 1.2 |
| E80 INH RIF | 0.009 | 1.0 | 0.9 |

[$c_{drug}$ = drug concentration; $c_{np}$ = nanoparticle concentration, $L_{drug}$, drug loading wt %].

Example 9: Synthesis of INH-Containing Polymer Nanoparticles from Blank Polymer 2

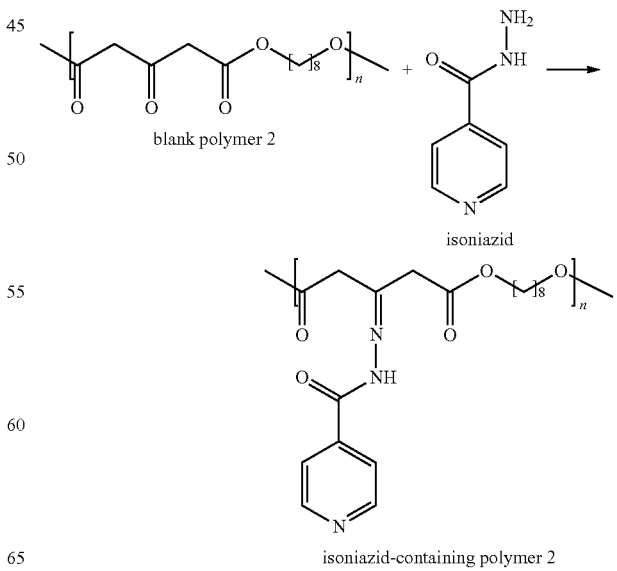

blank polymer 2 isoniazid isoniazid-containing polymer 2

INH-containing polymer 2 nanoparticles were prepared from blank polymer 2. Blank polymer 2 was prepared as described above. The INH-containing polymer 2 was prepared from blank polymer 2 and INH using the same method described above for the preparation of INH-containing polymer 1 in Example 1.

Figure 23:
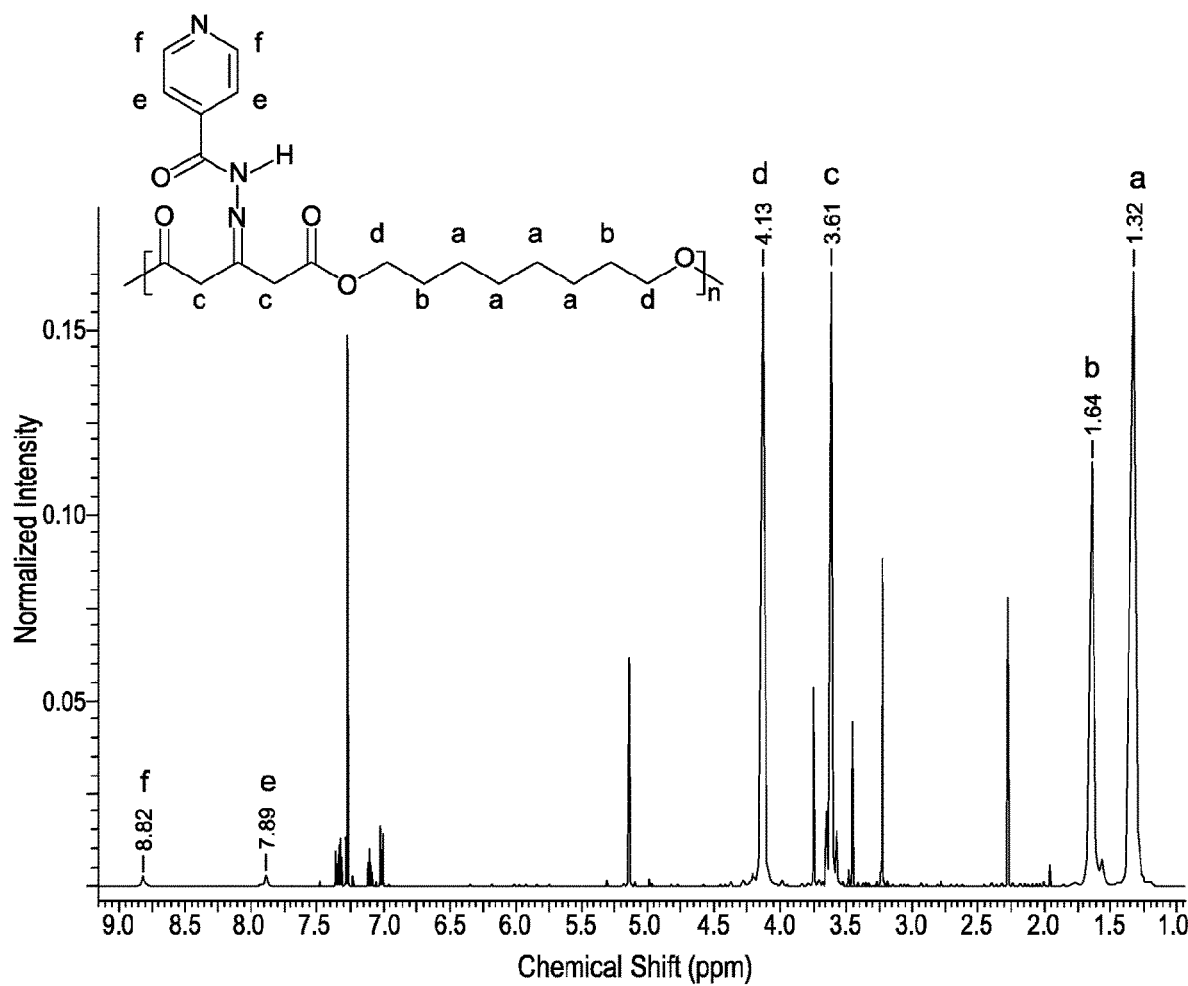
FIG. 23 is a $^1$H-NMR spectrum of blank polymer 2 incorporating INH in CDCl$_3$.

FIG. 23 shows the $^1$H NMR spectrum of blank polymer 2 incorporating INH in CDCl$_3$.

The INH-containing polymer 2 prepared from blank polymer 2 was formulated into nanoparticles and characterised as described in Example 1 above. The DLS characterisation results are detailed in Table 17.

DLS Characterization of Polymeric Nanoparticles

TABLE 17

| INH-containing polymer (from blank polymer 2) | Z-average ± PDI width d, nm | $d_{Number}$, nm | PDI | zeta potential ± zeta deviation, mV |
|---|---|---|---|---|
| water | 152 ± 58 | 114 | 0.146 | N/A |
| pH 5 | 677 ± 400 | 493 | 0.363 | −24 ± 16 |
| pH 7.4 | 154 ± 35 | 128 | 0.056 | −37 ± 31 |

Z-average: cumulants mean; $d_{Number}$: number-mean size; PDI: polydispersity index.

Table 18 shows the results of drug release from the INH-containing polymer nanoparticles. Drug release was measured by HPLC after incubation of the nanoparticles in 0.5 M NaOH for overnight at 60° C. The drug content is specified in respect to the dry mass of nanoparticles.

Drug Loading

TABLE 18

| nanoparticles | $c_{drug}$, mg/mL | $c_{np}$, mg/mL | $L_{drug}$, wt % |
|---|---|---|---|
| INH-containing polymer (from blank polymer 2) | 0.009 | 1.0 | 0.9 |

[$c_{drug}$ = drug concentration; $c_{np}$ = nanoparticle concentration, $L_{drug}$, drug loading wt %].

Example 10: Synthesis of INH-Containing Polymer Nanoparticles from Blank Polymer 3

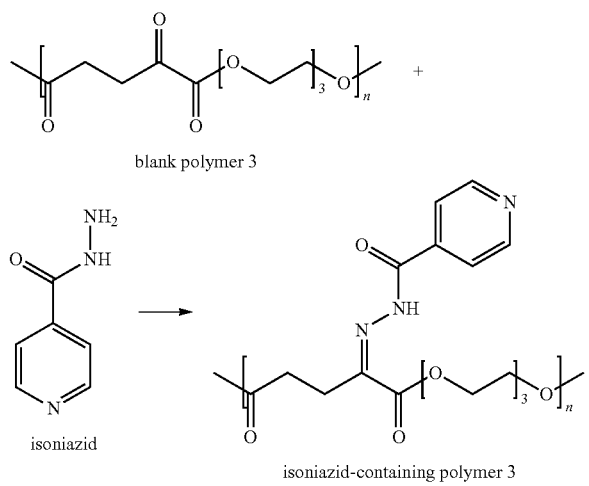

INH-containing polymer 3 nanoparticles were prepared from blank polymer 3. Blank polymer 3 was prepared as described above. The INH-containing polymer was prepared from blank polymer 3 and INH using the same method described above for the preparation of INH-containing polymer 1 in Example 1.

The polymers were formulated into nanoparticles and characterised as described above in Example 1. The DLS characterisation results are detailed in Table 19.

DLS Characterization of Polymeric Nanoparticles

TABLE 19

| INH-containing polymer (from blank polymer 3) | Z-average ± PDI width d, nm | $d_{Number}$, nm | PDI | zeta potential ± zeta deviation, mV |
|---|---|---|---|---|
| water | 532 ± 365 | 134 | 0.471 | −26 ± 10 |

Z-average: cumulants mean;; $d_{Number}$: number-mean size; PDI: polydispersity index.

Table 20 shows the results of drug release from the INH-containing polymer nanoparticles. Drug release was measured by HPLC after incubation of the nanoparticles in 0.5 M NaOH overnight at 60° C. The drug content is specified in respect to the dry mass of nanoparticles.

Drug Loading

TABLE 20

| nanoparticles | $c_{drug}$, mg/mL | $c_{np}$, mg/mL | $L_{drug}$, wt % |
|---|---|---|---|
| INH-containing polymer (from blank polymer 3) | 0.04 | N/A | 4 |

[$c_{drug}$ = drug concentration; $c_{np}$ = nanoparticle concentration, $L_{drug}$, drug loading wt %].

Example 11: In Vitro Release of INH from Nanoparticles

The in vitro release of INH from nanoparticles of INH-containing polymer 1 was assayed as follows. 200 μL of a suspension containing INH-containing polymer 1 formulated into nanoparticles was centrifuged for 2 min at 13 000 rpm. The supernatant was discarded and the pellet was resuspended in various buffers: 10 mM HCl adjusted to pH 2;

25 mM acetate buffer adjusted to pH 4;

25 mM phosphate buffer adjusted to pH 7.4;

and incubated at 37° C. under orbital shaking at 150 rpm. At regular time intervals the suspensions were centrifuged 2 min at 13 000 rpm then 200 μL of the supernatant was pipetted and replaced by 200 μL of fresh buffer. Pellets were resuspended and suspensions were further incubated while the amount of isoniazid in the supernatant was measured by HPLC as described previously.

Figure 24:
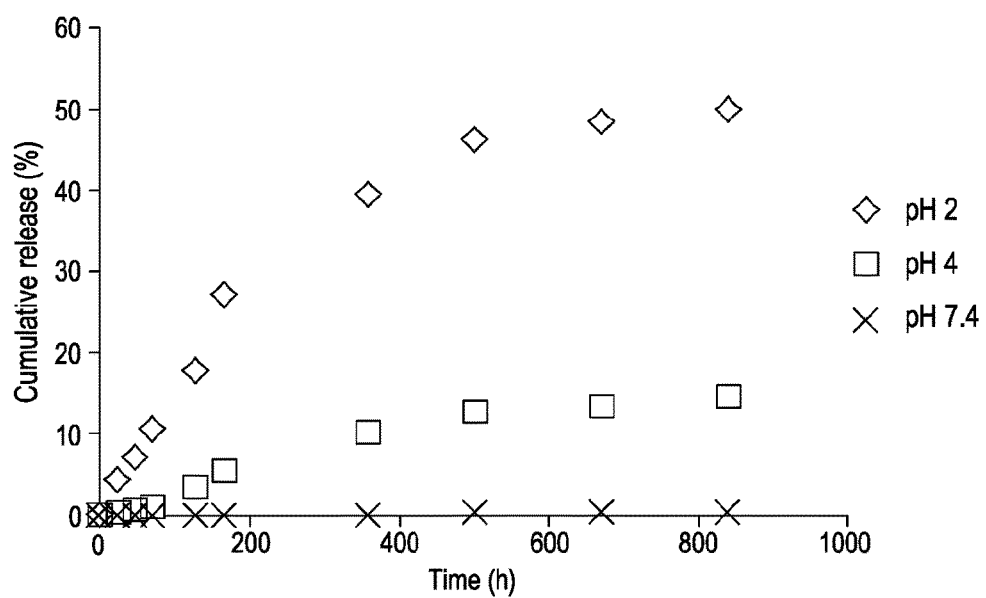
FIG. 24 is a graph showing the cumulative release of isoniazid from nanoparticles formed from blank polymer 1 incorporating INH.

FIG. 24 is a graph showing the cumulative release of isoniazid from the nanoparticles formulated with INH-containing polymer 1 incubated in various buffers at 37° C. INH is released at different rate depending on the pH. After a month more than 50% of INH is released at pH 2 and 15% at pH 4 whereas less than 1% release is observed at pH 7.4. This graph shows the effect of pH on the stability of the bond between INH and the polymer. INH formulated with the blank polymer is stable at physiological pH (pH 7.4) and is released in acidic conditions found in cell compartments such as lysosome, endosome, phagosome, phagolysosome and autophagosome found in various cells such as macrophages.

Example 12: In Vitro Evaluation of Nanoparticles on Tuberculosis-Infected Macrophages The antibiotic efficacy of the synthesized nanoparticles was next evaluated and compared to that of the free drugs against *Mycobacterium bovis* BCG-lux (Bacille Calmette Guerin) grown in human monocyte-derived macrophages. The bioluminescence of BCG-lux after lysis of macrophages was used as an indicator of BCG-lux viability and therefore as an experimental cell model of tuberculosis. Results are presented against the BCG-lux viability of corresponding untreated (control) cells.

Figure 25:
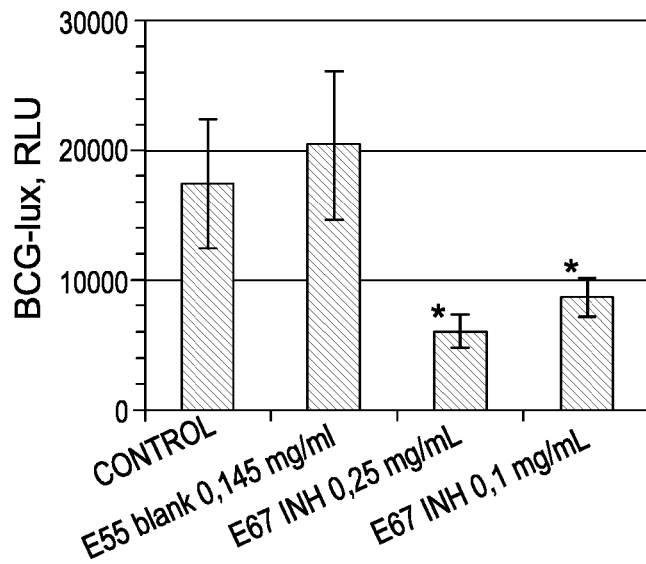
FIG. 25 is a bar graph showing the bioluminescence of *Mycobacterium bovis* BCG-lux grown in human monocyte-derived macrophages of the INH-containing nanoparticles E67 and the corresponding blank nanoparticles E55 on BCG-lux viability after 72 h incubation.
Figure 26:
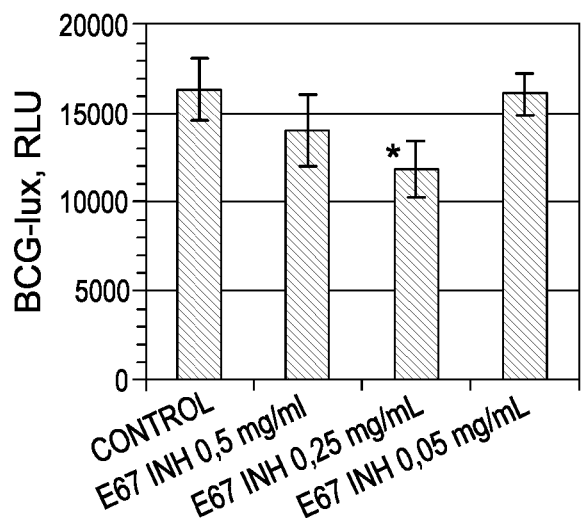
FIG. 26 is a bar graph showing the bioluminescence of *Mycobacterium bovis* BCG-lux grown in human monocyte-derived macrophages in the presence of E67 nanoparticles for 24 h.
Figure 27:
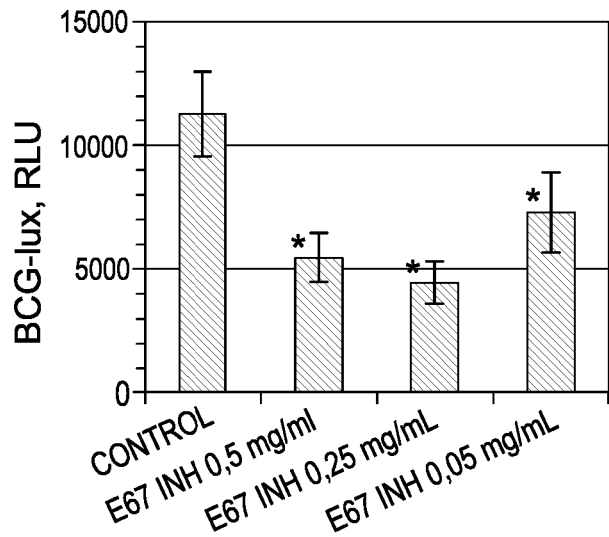
FIG. 27 is a bar graph showing the bioluminescence of *Mycobacterium bovis* BCG-lux grown in human monocyte-derived macrophages in the presence of E67 nanoparticles for 72 h.
Figure 28:
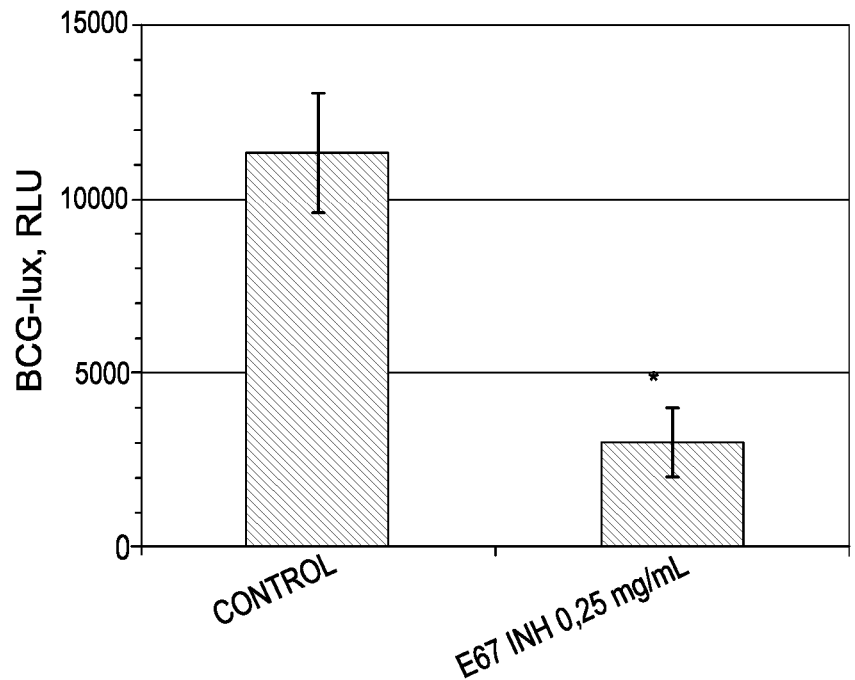
FIG. 28 is a bar graph showing the bioluminescence of *Mycobacterium bovis* BCG-lux grown in human monocyte-derived macrophages in the presence of E67 nanoparticles for 120 h.
Figure 29:
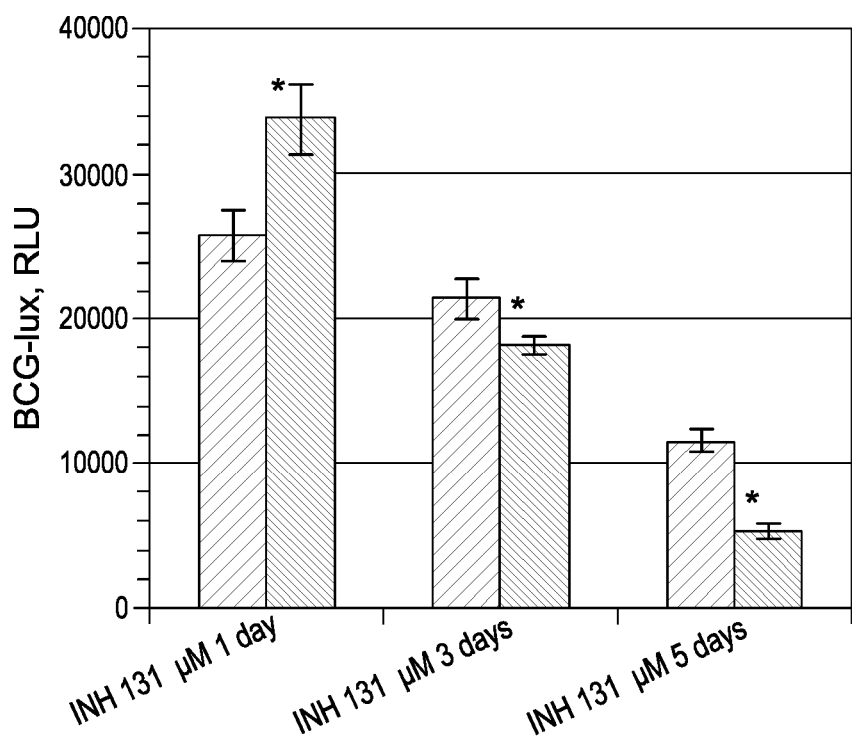
FIG. 29 is a bar graph showing the bioluminescence of *Mycobacterium bovis* BCG-lux grown in human monocyte-derived macrophages in the presence of free INH (grey bars) compared to the respective control groups (striped bars)

FIG. 25 shows the effect of the INH-containing nanoparticles E67 and the corresponding blank nanoparticles E55 on BCG-lux viability. The mass concentration of blank nanoparticles E55 corresponds to equimolar polymer concentrations of a 0.25 mg mL$^{-1}$ suspension of E67 nanoparticles. In this test, the bioluminescence of *Mycobacterium bovis* BCG-lux grown in human monocyte-derived macrophages was investigated for 72 h. Cells were grown in 24 well cell culture plates at 37 C and 5% $CO_2$ in 200 μL DMEM containing 10% FCS, 60 mg mL$^{-1}$ PEN and containing nanoparticles. Error bars indicate ±standard deviation (n=6). The asterisks indicates a significant difference to the control group, determined by unpaired Student t-test at $\alpha=0.05$.

The results show that the bioluminescence of BCG-lux was not significantly affected when co-incubated with E55 blank nanoparticles. INH nanoparticles E67 containing the same backbone polymer reduced the viability of BCG-lux by 70% and 74% at nanoparticle concentrations of 0.1 and 0.25 mg mL$^{-1}$, respectively.

The effect of concentration and time of incubation of the INH-containing nanoparticles E67 and free INH on BCG-lux viability was also investigated and the results are shown in FIGS. 26-29. Macrophages were cultivated in 24 well cell culture plates at 37° C. and 5% $CO_2$ in 300 μL DMEM containing 10% FCS, 60 mg mL$^{-1}$ PEN and the nanoparticles and free drug. Free INH was used as a positive control. The INH concentration corresponded to the experimental release from a 0.25 mg mL$^{-1}$ E67 nanoparticle suspension. The error bars indicate ±standard deviation (n=6). The asterisks indicate a significant difference to the control group, determined by unpaired Student t-test at $\alpha=0.05$.

The results show that co-incubation of intracellular BCG-lux with E67 INH nanoparticles for 24 h resulted in an optimum antimycobacterial efficacy at a nanoparticle concentration of 0.25 mg mL$^{-1}$. The BCG-lux viability decreased significantly between 24 h and 72 h in all of the tests in the presence of E67 nanoparticles.

120 h efficacy was only determined at a nanoparticle concentration of 0.25 mg mL$^{-1}$. The results show that the antibiotic efficacy compared to untreated cells increased from 61% after 72 h to 74% after 120 h.

The results also show an initial 32% increase in presence of free INH of BCG-lux bioluminescence after 24 h when compared to untreated cells. After 72 h, the viability of cells incubated with INH was 15% lower than that for control cells. After 120 h, the 53% reduction of BCG-lux bioluminescence was observed. Thus, the efficacy of free INH was lower than the efficacy of the corresponding nanoparticle dispersion at all times.

Figure 30:
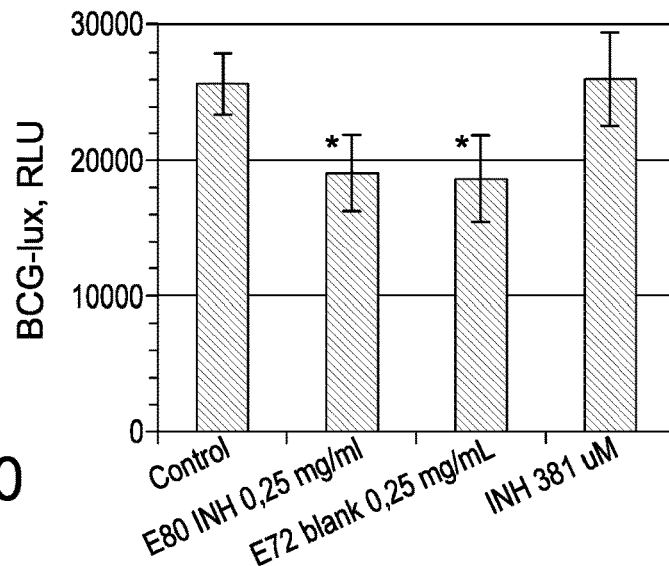
FIG. 30 is a bar graph showing the bioluminescence of *Mycobacterium bovis* BCG-lux grown in human monocyte-derived macrophages in the presence of E72 or E80 nanoparticles for 24 h.
Figure 31:
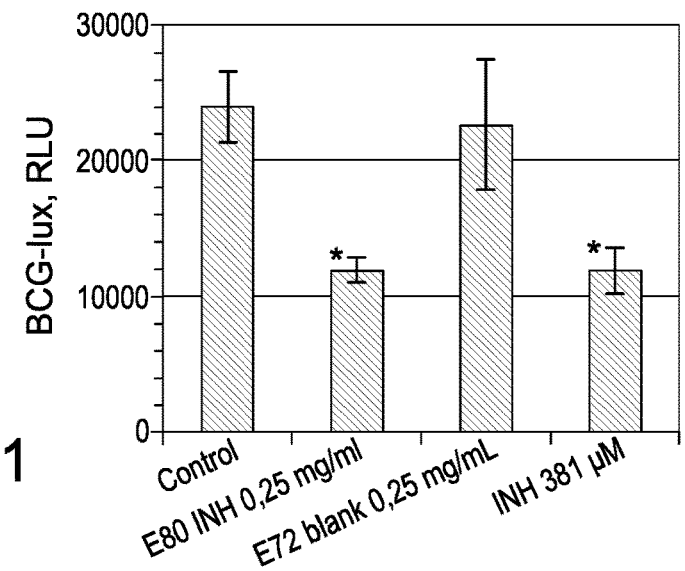
FIG. 31 is a bar graph showing the bioluminescence of *Mycobacterium bovis* BCG-lux grown in human monocyte-derived macrophages in the presence of E72 or E80 nanoparticles for 72 h.

The effect of polymer chain length on the antimycobacterial efficacy was also investigated and the results are shown in FIGS. 30 and 31. Nanoparticles of the 16.5 kDa blank polymer E72 and the 16 kDa INH polymer E80 were investigated in the experimental tuberculosis model. Nanoparticle concentrations were kept at the E67 optimum concentration of 0.25 mg mL$^{-1}$. Macrophages were cultivated in 24 well cell culture plates at 37° C. and 5% $CO_2$ in 300 μL DMEM containing 10% FCS, 60 mg mL$^{-1}$ PEN and the nanoparticles and free drug. Free INH was used as a positive control. The error bars indicate ±standard deviation (n=6). The asterisks indicate a significant difference to control group, determined by unpaired Student t-test at $\alpha=0.05$.

The results show that after 24 h, the BCG-lux viability was statistically identical for blank and INH nanoparticles. The antibiotic efficacies of the INH nanoparticles compared to the control group increased from 25% to 41% after 72 h. These effects were significantly lower than those noticed for the shorter polymer length E67 nanoparticles and it was also noted that the blank polymer E72 had no significant efficacy after 72 h. The standard deviation was comparably high.

Free INH was used as a positive control in a concentration corresponding to the experimental release of a 0.25 mg mL$^{-1}$ E80 INH nanoparticle suspension. After 24 h, no antimycobacterial activity of free INH was measured, as was also noted in earlier experiments described above. After 72 h, the antibiotic efficacy was equivalent to the antibiotic efficacy of E80 nanoparticles.

Figure 32:
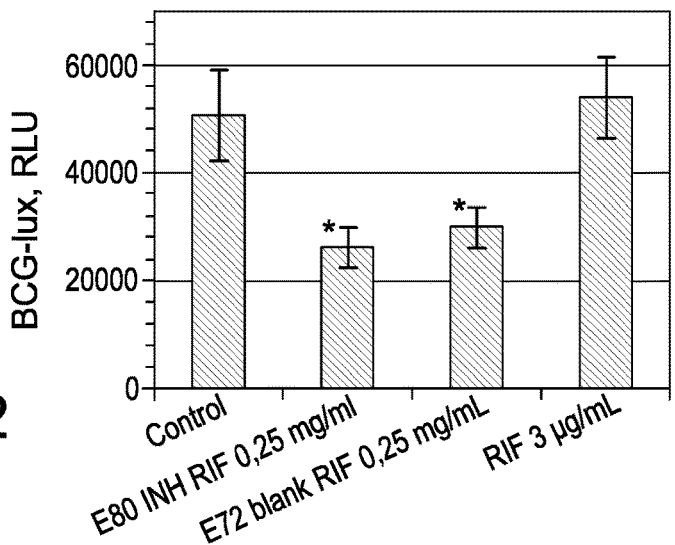
FIG. 32 is a bar graph showing the bioluminescence of *Mycobacterium bovis* BCG-lux grown in human monocyte-derived macrophages in the presence of E72 or E80 INH RIF nanoparticles for 72 h.

The antibiotic efficacy of E72 and E80 polymers encapsulating RIF were also investigated. FIG. 32 shows the bioluminescence of *Mycobacterium bovis* BCG-lux grown in human monocyte-derived macrophages in the presence of E72 or E80 INH RIF nanoparticles for 72 h. Free RIF was used as a positive control in a concentration corresponding to the experimental release of a 0.25 mg mL$^{-1}$ E80 INH RIF nanoparticle suspension.

The results show that after 72 h, efficacies of the INH nanoparticles E80, E80 INH RIF were not distinguishable. In contrast to the E72 blank nanoparticles, RIF encapsulating E72 nanoparticles induced a 41% reduction of BCG-lux viability. Free RIF did not induce a significant antimycobacterial effect in this experiment.

Figure 33:
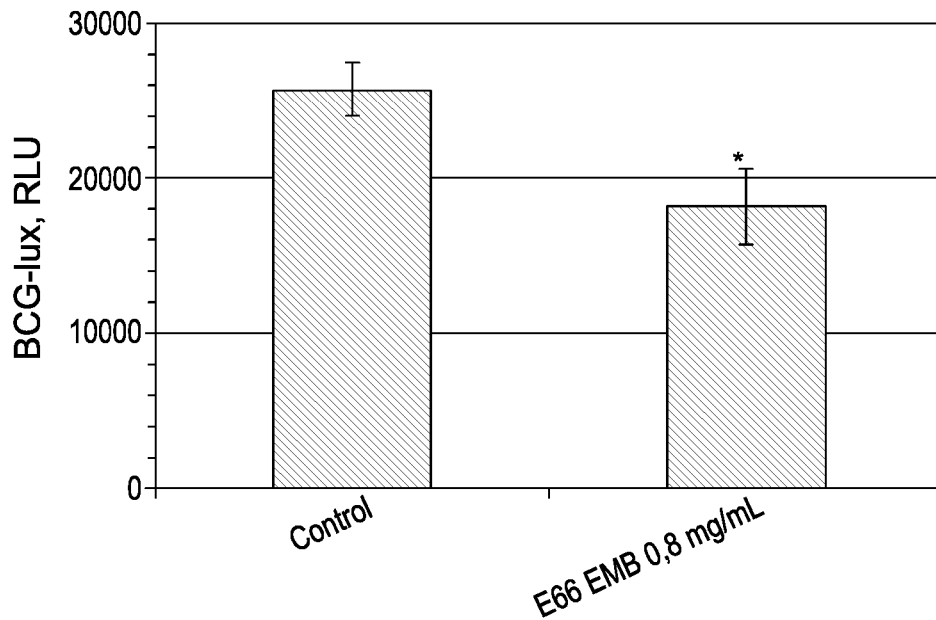
FIG. 33 is a bar graph showing the bioluminescence of *Mycobacterium bovis* BCG-lux grown in human monocyte-derived macrophages in the presence of E66 nanoparticles for 24 h.
Figure 34:
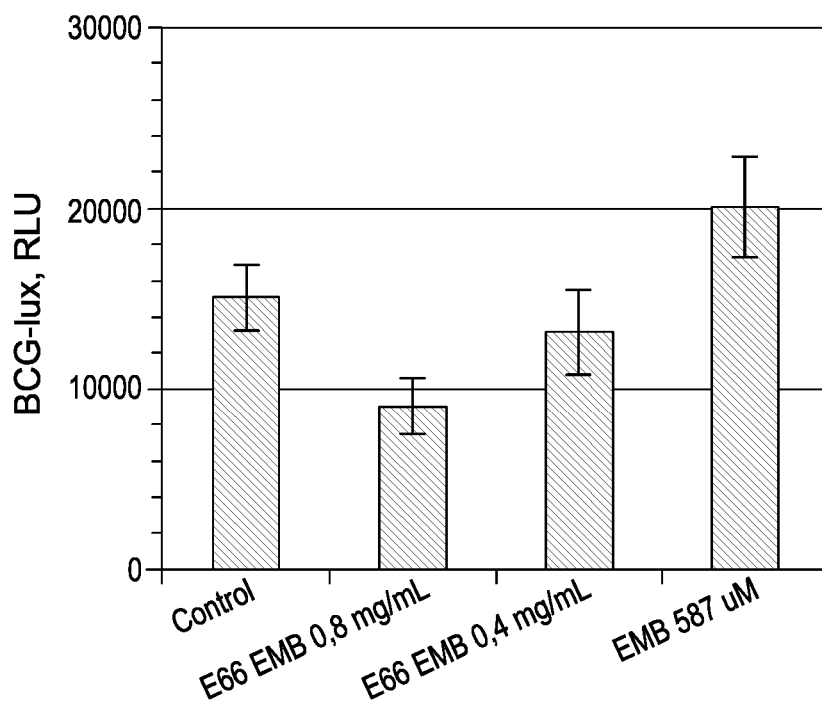
FIG. 34 is a bar graph showing the bioluminescence of *Mycobacterium bovis* BCG-lux grown in human monocyte-derived macrophages in the presence of E66 nanoparticles for 72 h.

The efficacy of ethambutol-containing polymer nanoparticles E66 was analyzed as described above and the results are shown in FIGS. 33 and 34. EMB was used as a positive control. Macrophages were cultivated in 24 well cell culture plates at 37 C and 5% $CO_2$ in 300 μL DMEM containing 10% FCS, 60 mg mL$^{-1}$ PEN and the drug formulation. The error bars indicate ±standard deviation (n=6). The asterisks indicate a significant difference to the control group, determined by unpaired Student t-test at $\alpha=0.05$.

The results show that a 0.8 mg mL$^{-1}$ suspension of EMB nanoparticles E66 induced a 28% reduction of BCG-lux luminescence after 24 h and a 40% reduction after 72 h. E66 efficacy was also tested at a concentration of 0.4 mg mL$^{-1}$. EMB nanoparticles E66 at a concentration of 0.4 mg mL$^{-1}$ did not induce a significant effect on BCG-lux viability after 72 h.

Free EMB was used as a positive control in a concentration corresponding to a 15 wt % release of a 0.8 mg mL$^{-1}$ E66 nanoparticle suspension. The free drug did not reduce BCG-lux viability.

Example 13: Cytotoxicity of Nanoparticles

Figure 35:
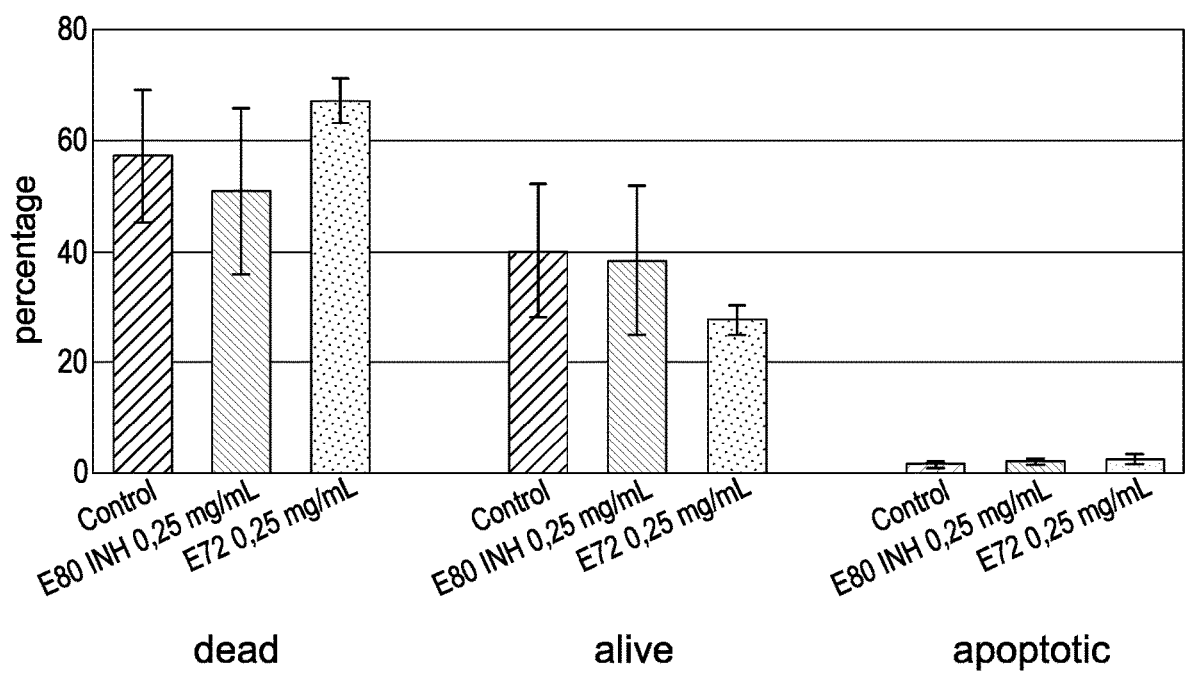
FIG. 35 is a bar graph showing the cytotoxicity of E80 INH and E72 nanoparticles.

The cytotoxicity of the nanoparticle formulations E72 blank and E80 was tested using an Dead cell apoptosis kit with Annexin V FITC and PI, for flow cytometry (MolecularProbes®, UK) and the results are shown in FIG. 35. $2*10^5$ cells per well were seeded in 24 well cell culture plates, differentiated for 5 days, and incubated with nanoparticles as described previously. The kit was used according to manufacturer's instructions. Live cells do not bind the human anticoagulant protein Annexin V and are therefore not stained by the conjugated fluorescent dyes Fluorescein thiocyanate (FITC) and Propidium iodide (PI). Apoptotic cells bind Annexin V, but only show FITC fluorescence because the intact membranes are impermeable for PI. Dead cells are permeable for PI and show both FITC and PI fluorescence in a Fortessa 4 laserflow cytometer (Becton, Dickinson and Company, UK).

For the purposes of this experiment, dead cells are FITC/PI+, live cells are FITC/PI−, and apoptotic cells are FITC+, PI−. In FIG. 35, the striped bars represent a control group without treatment, the grey bars represent the INH nanoparticles and the dotted bars represent the blank nanoparticles. The error bars indicate ±standard deviation.

The results show that macrophages treated with E72 and E80 nanoparticles did not contain significantly increased percentages of dead or apoptotic cells.

Example 14: Synthesis of Insulin-Containing Polymer

Blank polymer 1 (30 mg, 5 µmol) and insulin (15 mg, 2.6 µmol) were solubilized separately in anhydrous DMSO. Both solutions were mixed in a round-bottom flask with mechanical stirring, p-Toluenesulfonic acid was added in catalytic amount. Vacuum was applied, and the reaction was left for 48 h. The reaction product was retrieved by precipitation of the reaction mixture in aqueous buffer (pH 9). The precipitate was spun down, washed with buffer and water, and then retrieved in DCM which was then evaporated. The reaction product was left to dry overnight in a desiccator before RP-HPLC analysis.

Figure 36:
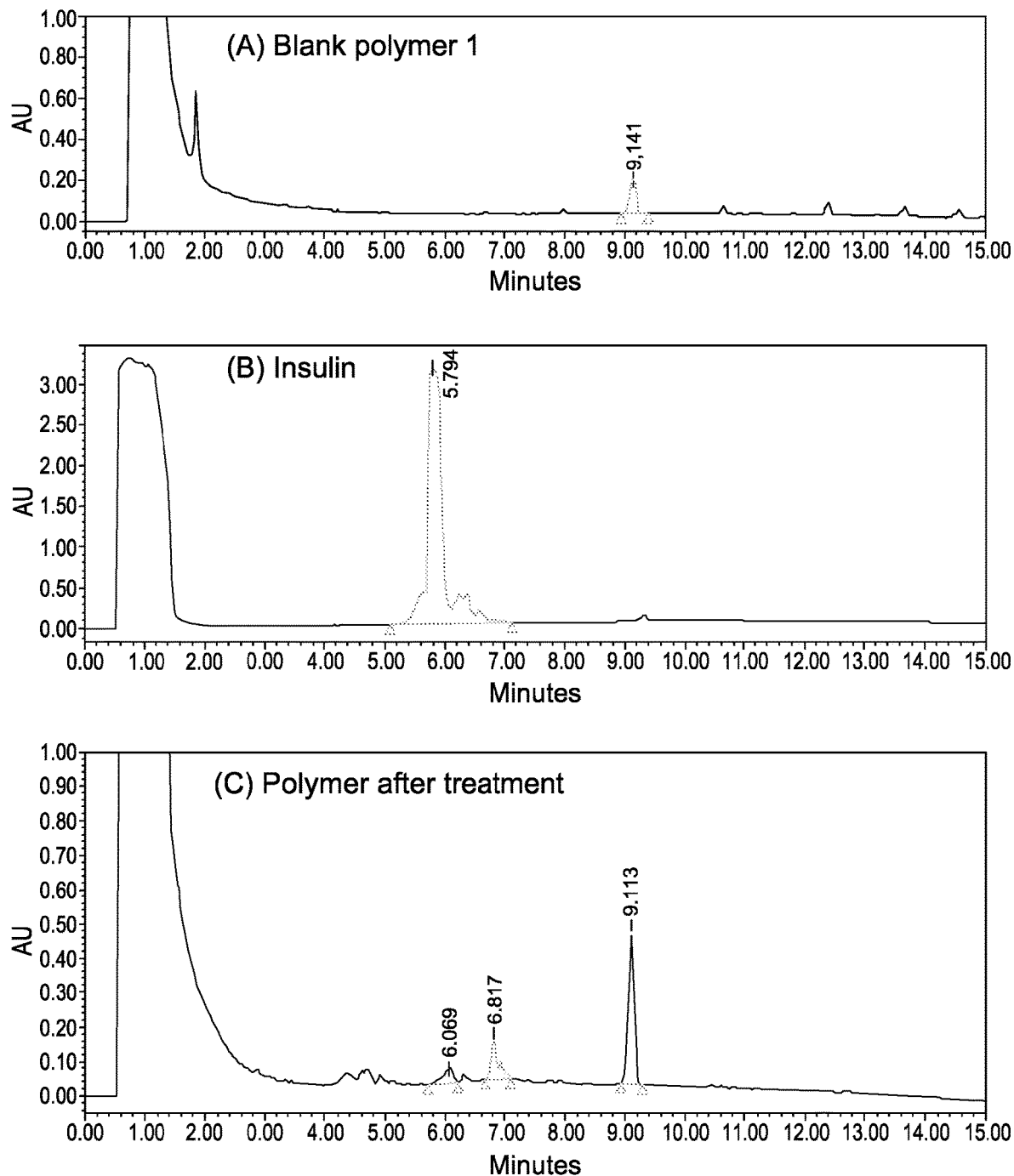
FIG. 36 is a graph showing RP-HPLC analysis of blank polymer 1 (A), Insulin (B), and the polymer after reaction with insulin and after treatment (precipitation and washes) (C).

FIG. 36 is a graph showing RP-HPLC analysis of blank polymer 1 (A), Insulin (B), and the polymer 1 after reaction with insulin and after treatment (precipitation and washes) (C).

FIG. 36 shows that after the treatment of the reaction mixture another product is formed as seen by the peak at $t_R=6.82$ min. The blank polymer 1 ($t_R=9.11$ min) and some residual Insulin ($t_R=6.01$) are also observed.

The invention claimed is:

1. A particle which is a microparticle or a nanoparticle having an average diameter of 1 nm to 10 microns and comprising a linear polymer, wherein said linear polymer comprises a repeat unit of formula MTV

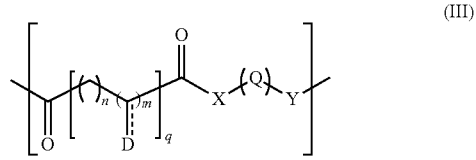

(III)

wherein:
each n is independently 0 or an integer from 1 to 6;
each m is independently 0 or an integer from 1 to 4, and at least one m is 1;
---- is a bond which is absent or present;
each D is a moiety which is a biologically active molecule, or a derivative thereof, when the C to D bond(s) is broken;
each q is an integer from 1 to 8;
X is selected from O, S, NH and NR';
Y is selected from O, S, NH and NR';
R' is $C_{1-20}$ hydrocarbyl;
Q is selected from $-(CH_2)_p-$, $-(CH_2CH_2O)_sCH_2CH_2-$, $-(CH_2)_rNR'-(CH_2)_r-$ and $-(CH_2CH_2CH_2O)_sCH_2CH_2CH_2-$; and each of p, r and s is independently an integer from 1 to 16;

wherein release of said biologically active molecule, or a derivative thereof, from the linear polymer is pH sensitive and is dependent upon the nature of the bond between said biologically active molecule and the repeat unit of the linear polymer to which it is covalently bound; and wherein the particle enables the delivery in vivo of said linear polymer comprising a biologically active molecule or derivative thereof inside a target cell, in which the biologically active molecule or derivative thereof is cleaved from the linear polymer by an acidic and/or hydrolytic environment.

2. A particle as claimed in claim 1, wherein in said repeat unit of formula (III), q is 1.

3. A particle as claimed in claim 1, wherein in said repeat unit of formula (III), m is 1 or 2.

4. A particle as claimed in claim 1, wherein in said repeat unit of formula (III), n is 1, 2 or 3.

5. A particle as claimed in claim 1, wherein said repeat unit of formula (III) is derived from dimethyl-2-oxo-glutarate or dimethyl-3-oxo-glutarate.

6. A particle as claimed in claim 1, wherein the subunit within the repeat unit (III) that is represented by formula (II)

(II)

is derived from 1,8-octanediol, triethylene glycol or N-methyldiethanolamine.

7. A particle according to claim 1, wherein said biologically active molecule is selected from the group consisting of drug molecules having a molecular weight less than or equal to about 5 kDa, peptides, proteins, peptide mimetics, antibodies, antigens, deoxyribonucleic acid (DNA), messenger ribonucleic acid (mRNA), small interfering RNA, small hairpin RNA, microRNA, peptide nucleic acid (PNA), foldamers, carbohydrates, carbohydrate derivatives, non-Lipinski molecules, synthetic peptides and synthetic oligonucleotides.

8. A particle as claimed in claim 1, wherein said biologically active molecule comprises a functional group that is able to form a covalent bond with a ketone group.

9. A particle as claimed in claim 8, wherein said biologically active molecule comprises at least one hydrazine group, at least one hydrazide group, at least one amine group, at least one aminooxy group, at least one hydroxyl group or at least one thiol group.

10. A particle as claimed in claim 1, wherein the linear polymer comprises a repeat unit of formula (Ma):

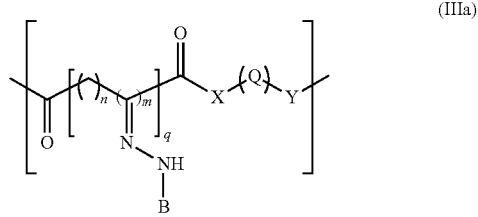

(IIIa)

wherein:
each n is independently 0 or an integer from 1 to 6;
each m is independently 0 or an integer from 1 to 4, and at least one m is 1;
each B is the remainder of D;
each q is an integer from 1 to 8;
X is selected from O, S, NH and NR';
Y is selected from O, S, NH and NR';
R' is $C_{1-20}$ hydrocarbyl;
Q is selected from —$(CH_2)_p$—, —$(CH_2CH_2O)_s$ $CH_2CH_2$—, —$(CH_2)_rNR'$—$(CH_2)_r$— and —$(CH_2CH_2CH_2O)_sCH_2CH_2CH_2$—; and each of p, r and s is independently an integer from 1 to 16.

11. A particle as claimed in claim 1, wherein the linear polymer comprises a repeat unit of formula (IIIb):

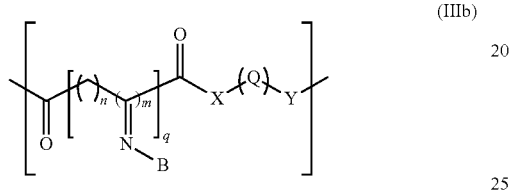

wherein:
each n is independently 0 or an integer from 1 to 6;
each m is independently 0 or an integer from 1 to 4, and at least one m is 1;
each B is the remainder of D;
each q is an integer from 1 to 8;
X is selected from O, S, NH and NR';
Y is selected from O, S, NH and NR';
R' is $C_{1-20}$ hydrocarbyl;
Q is selected from —$(CH_2)_p$—, —$(CH_2CH_2O)_s$ $CH_2CH_2$—, —$(CH_2)_rNR'$—$(CH_2)_r$— and —$(CH_2CH_2CH_2O)_sCH_2CH_2CH_2$—; and each of p, r and s is independently an integer from 1 to 16.

12. A particle as claimed in claim 1, wherein the linear polymer comprises a repeat unit of formula (IIIci) or (IIIcii):

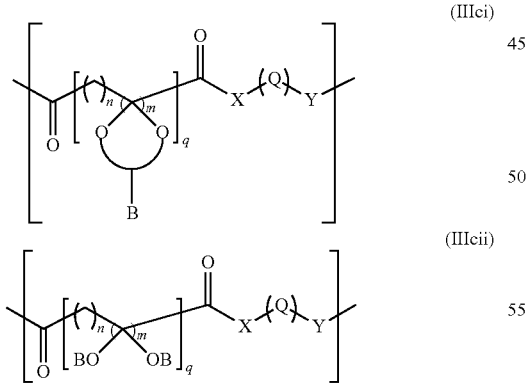

wherein:
each n is independently 0 or an integer from 1 to 6;
each m is independently 0 or an integer from 1 to 4, and at least one m is 1;
each B is the remainder of D;
each q is an integer from 1 to 8;
X is selected from O, S, NH and NR';
Y is selected from O, S, NH and NR';
R' is $C_{1-20}$ hydrocarbyl;
Q is selected from —$(CH_2)_p$—, —$(CH_2CH_2O)_s$ $CH_2CH_2$—, —$(CH_2)_rNR'$—$(CH_2)_r$— and —$(CH_2CH_2CH_2O)_sCH_2CH_2CH_2$—; and each of p, r and s is independently an integer from 1 to 16.

13. A particle as claimed in claim 1, wherein the linear polymer comprises a repeat unit of formula (IIIdi) or (IIIdii):

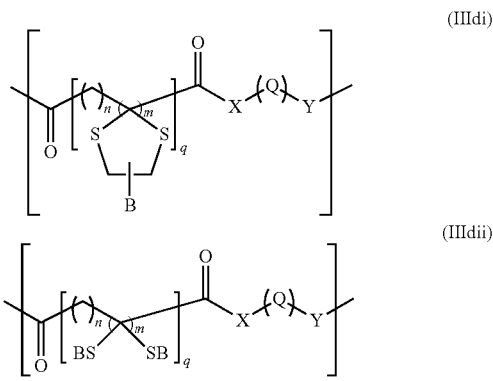

wherein:
each n is independently 0 or an integer from 1 to 6;
each m is independently 0 or an integer from 1 to 4, and at least one m is 1;
each B is the remainder of D;
each q is an integer from 1 to 8;
X is selected from O, S, NH and NR';
Y is selected from O, S, NH and NR';
R' is $C_{1-20}$ hydrocarbyl;
Q is selected from —$(CH_2)_p$—, —$(CH_2CH_2O)_s$ $CH_2CH_2$—, —$(CH_2)_rNR'$—$(CH_2)_r$— and —$(CH_2CH_2CH_2O)_sCH_2CH_2CH_2$—; and each of p, r and s is independently an integer from 1 to 16.

14. A particle as claimed in claim 1, wherein the linear polymer comprises a repeat unit of formula (IIIe):

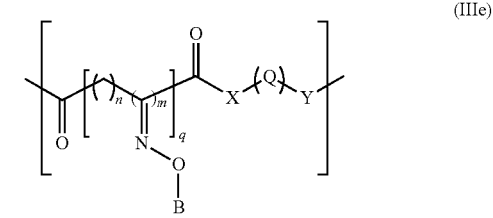

wherein:
each n is independently 0 or an integer from 1 to 6;
each m is independently 0 or an integer from 1 to 4, and at least one m is 1;
each B is the remainder of D;
each q is an integer from 1 to 8;
X is selected from O, S, NH and NR';
Y is selected from O, S, NH and NR';
R' is $C_{1-20}$ hydrocarbyl;
Q is selected from —$(CH_2)_p$—, —$(CH_2CH_2O)_s$ $CH_2CH_2$—, —$(CH_2)_rNR'$—$(CH_2)_r$— and —$(CH_2CH_2CH_2O)_sCH_2CH_2CH_2$—; and each of p, r and s is independently an integer from 1 to 16.

15. A particle as claimed in claim 1, wherein the linear polymer comprises a unit of formula (Va) or (Vb):

Va

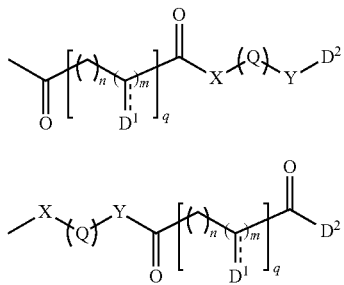

Vb wherein:
each n is independently 0 or an integer from 1 to 6;
each m is independently 0 or an integer from 1 to 4, and at least one m is 1;
each $D^1$ is a moiety which is a biologically active molecule, or a derivative thereof, when the C to $D^1$ bond is broken;
$D^2$ is a moiety which is a biologically active molecule, a derivative of a biologically active molecule, or a targeting agent, when the Y to $D^2$ bond is broken;
each q is an integer from 1 to 8;
X is selected from O, S, NH and NR';
Y is selected from O, S, NH and NR';
R' is $C_{1-20}$ hydrocarbyl;
Q is selected from $—(CH_2)_p—$, $—(CH_2CH_2O)_s CH_2CH_2—$, $—(CH_2)_rNR'—(CH_2)_r—$ and $—(CH_2CH_2CH_2O)_sCH_2CH_2CH_2—$; and each of p, r and s is independently an integer from 1 to 16.

16. A particle as claimed in claim 15, wherein said biologically active molecule from which D1 derives comprises at least one hydrazine group, at least one hydrazide group, at least one amine group, at least one aminooxy group, at least one hydroxyl or at least one thiol group.

17. A particle as claimed in claim 15, wherein the biologically active molecule from which $D^2$ derives comprises a functional group selected from the group consisting of a carboxylic acid group, a carboxylic ester group, a carboxylate group, a carboxyl thioester group, an acyl phosphate group, a carboxylic acid anhydride group, a hydroxyl group, an acyl halide group, an amine group and a thiol group.

18. A particle as claimed in claim 1, wherein the linear polymer further comprises a repeat unit derived from a biologically active molecule.

19. A method for making a particle as claimed in claim 1, comprising:
reacting a compound of formula (I)

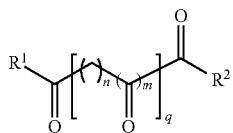

wherein:
$R^1$ and $R^2$ are each independently selected from OH, OR', SH, SR', $NH_2$, NHR' and $NR'_2$;
R' is $C_{1-20}$ hydrocarbyl;
each n is independently 0 or an integer from 1 to 6;
each m is independently 0 or an integer from 1 to 4, and at least one m is 1; and
q is an integer from 1 to 8;

with a compound of formula (II)

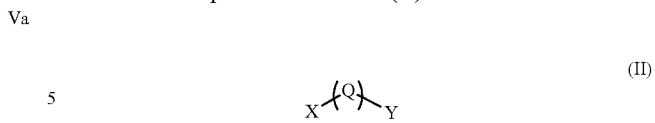

wherein:
X is selected from OH, OR', SH, SR', $NH_2$, NHR' and $NR'_2$;
Y is selected from OH, OR', SH, SR', $NH_2$, NHR' and $NR'_2$;
R' is $C_{1-20}$ hydrocarbyl;
Q is selected from $—(CH_2)_p—$, $—(CH_2CH_2O)_s CH_2CH_2—$, $—(CH_2)_rNR'—(CH_2)_r—$ and $—(CH_2CH_2CH_2O)_sCH_2CH_2CH_2—$; and each of p, r and s is independently an integer from 1 to 16;
and with a biologically active molecule to form a linear polymer, and forming the particle from the linear polymer.

20. A method as claimed in claim 19, wherein the reacting step occurs enzymatically.

21. A particle as claimed in claim 1 having an average diameter of 50 to 800 nm.

22. A particle as claimed in claim 1, further comprising an agent selected from the group consisting of a biologically active molecule, a molecular probe and a diagnostic agent which is non-covalently bound to said linear polymer.

23. A particle as claimed in claim 22, wherein said non-covalently bound agent is encapsulated in a structure formed by said linear polymer.

24. A particle as claimed in claim 22, wherein said non-covalently bound agent is a biologically active molecule, which is the same as or different from the biologically active molecule covalently bound to said linear polymer.

25. A method of claim 19, wherein the step of forming the particle is selected from nanoprecipitation, emulsion-diffusion, double emulsification, emulsion-coacervation, polymer-coating and layer-by-layer method.

26. A method of claim 25, wherein the step of forming the particle is nanoprecipitation and comprises dissolving the linear polymer and a biologically active molecule in a solvent to form a solution, and adding an anti-solvent to the solution thereby forming the particle.

27. A pharmaceutical composition comprising a particle as claimed in claim 1.

28. A dosage form comprising a particle as claimed in claim 1.

29. A method of treating a patient in need thereof, comprising administering to said patient a therapeutically effective amount of a particle as claimed in claim 1.

30. A method of treating a disease selected from inflammatory diseases, inflammatory bowel disease, rheumatoid arthritis, artherosclerosis, metabolic disorders, metabolic disorders (e.g., diabetes, insulin resistance, obesity, cancer, bacterial infections, tuberculosis, pneumonia, endocarditis, septicaemia, salmonellosis, typhoid fever, cystic fibrosis, chronic obstructive pulmonary diseases, viral infections, cardiovascular diseases, neurodegenerative diseases, neurological disorders, behavioral disorders, mental disorders, blood diseases, chromosome disorders, congenital diseases, genetic diseases, connective tissue diseases, digestive diseases, ear diseases, nose diseases, throat diseases, endocrine diseases, environmental diseases, eye diseases, female reproductive diseases, fungal infections, heart diseases, hereditary cancer syndromes, immune system diseases, kidney disease, urinary diseases, lung diseases, male reproductive diseases, mouth diseases, musculoskeletal diseases, myelodysplastic syndromes, nervous system diseases, nutritional diseases, parasitic diseases, and skin diseases;
  wherein said method comprises administering to a patient in need thereof a therapeutically effective amount of a particle as claimed in claim 1.

31. A particle as claimed in claim 7, wherein said biologically active molecule is a drug molecule having a molecular weight less than or equal to about 5 kDa.

\* \* \* \* \*

UNITED STATES PATENT AND TRADEMARK OFFICE
CERTIFICATE OF CORRECTION

PATENT NO.         : 10,709,717 B2  
APPLICATION NO.    : 15/518737  
DATED              : July 14, 2020  
INVENTOR(S)        : M. Ouberai et al.

Page 1 of 1

It is certified that error appears in the above-identified patent and that said Letters Patent is hereby corrected as shown below:

In the Claims

| Column | Line |  |
|---|---|---|
| 59 | 46 | Please change "MTV" to --(III)-- |
| 60 | 55 | Please change "(Ma)" to --(IIIa)-- |
| 64 | 54-55 | Please delete "metabolic disorders (e.g.," |

Signed and Sealed this  
Thirteenth Day of July, 2021

Drew Hirshfeld  
*Performing the Functions and Duties of the*  
*Under Secretary of Commerce for Intellectual Property and*  
*Director of the United States Patent and Trademark Office*